(12) United States Patent  
Rother et al.

(10) Patent No.: US 8,637,014 B2  
(45) Date of Patent: Jan. 28, 2014

(54) ANTIBODIES TO OX-2/CD200 AND USES THEREOF IN INHIBITING IMMUNE RESPONSES

(75) Inventors: Russell P. Rother, Oklahoma City, OK (US); Susan Faas McKnight, Old Lyme, CT (US)

(73) Assignee: Alexion Pharmaceuticals, Inc., Cheshire, CT (US)

( * ) Notice: Subject to any disclaimer, the term of this patent is extended or adjusted under 35 U.S.C. 154(b) by 0 days.

(21) Appl. No.: 13/533,546

(22) Filed: Jun. 26, 2012

(65) Prior Publication Data

US 2012/0321625 A1    Dec. 20, 2012

Related U.S. Application Data

(63) Continuation of application No. 12/670,379, filed as application No. PCT/US2008/009037 on Jul. 25, 2008, now Pat. No. 8,252,285.

(60) Provisional application No. 60/962,022, filed on Jul. 25, 2007.

(51) Int. Cl.  
*A61K 39/395* (2006.01)

(52) U.S. Cl.  
USPC ........................................ 424/130.1

(58) Field of Classification Search  
None  
See application file for complete search history.

(56) References Cited

U.S. PATENT DOCUMENTS

| 6,338,851 B1 | 1/2002 | Gorczynski |
| 2005/0048069 A1 | 3/2005 | Gorczynski et al. |
| 2010/0285030 A1 | 11/2010 | Bowdish et al. |

FOREIGN PATENT DOCUMENTS

WO    WO 2007/084321 A2    7/2007

OTHER PUBLICATIONS

Gorczynski et al., "Increased Expression of the Novel Molecule OX-2 is Involved in Prolongation of Murine Renal Allograft Survival," Transplantation, vol. 65(8), pp. 1106-1114 (1998).

Gorczynski et al., "A CD200Fc Immunoadhesin Prolongs Rat Islet Xenograft Survival in Mice," Transplantation, vol. 73(12), pp. 1948-1953 (2002).

Gorczynski et al., "CD200 Immunoadhesin Suppresses Collagen-Induced Arthritis in Mice," Clinical Immunology, vol. 101(3), pp. 328-334 (2001).

Minas et al., "Is the CD200/CD200 receptor interaction more than just a myeloid cell inhibitory signal," Critical Reviews in Immunology, vol. 26(3), pp. 213-230 (2006).

Gorczynski, Reginald M., "Transplant tolerance modifying antibody to CD200 receptor, but not CD200, alters cytokine production profile from stimulated macrophages," European Journal of Immunology, vol. 31(8); pp. 2331-2337 (2001).

*Primary Examiner* — Ilia Ouspenski  
(74) *Attorney, Agent, or Firm* — Ropes & Gray LLP

(57) ABSTRACT

This disclosure provides methods and compositions for inhibiting immune responses. The disclosure also provides methods and compositions for inhibiting graft rejection and promoting or prolonging graft survival.

29 Claims, 30 Drawing Sheets

FIGURE 1A Note: Figs. 1-4, leader sequences (AA) are underlined and constant regions are in bold.

chC2aB7-hG1
Heavy chain (introns in hG1) (SEQ ID NO. 1)
<u>MGWSCIILFLVATATGVHS</u>LEVQLQQSGPELVKPGASLKMSCKASGYSFT
DYIILWVKQNHGKSLEWIGHIDPYYGSSNYNLKFKGKATLTVDKSSSTAY
MQLNSLTSEDSAVYYCGRSKRDYFDYWGQGTTLTVSS**ASTKGPSVFPLA
PSSKSTSGGTAALGCLVKDYFPEPVTVSWNSGALTSGVHTFPAVLQSS
GLYSLSSVVTVPSSSLGTQTYICNVNHKPSNTKVDKRVEPKSCDKTHT
CPPCPAPELLGGPSVFLFPPKPKDTLMISRTPEVTCVVVDVSHEDPEV
KFNWYVDGVEVHNAKTKPREEQYNSTYRVVSVLTVLHQDWLNGKE
YKCKVSNKALPAPIEKTISKAKGQPREPQVYTLPPSREEMTKNQVSLT
CLVKGFYPSDIAVEWESNGQPENNYKTTPPVLDSDGSFFLYSKLTVDK
WQQGNVFSCSVMHEALHNHYTQKSLSLSPGK**

FIGURE 1B (SEQ ID NO. 2) (genomic sequence hG1)

ATGGGATGGAGCTGTATCATCCTCTTCTTGGTAGCAACAGCTACAGGTGTCCACTCCCTCGAG
GTCCAGCTGCAACAGTCTGGACCTGAGCTGGTGAAGCCTGGGGCTTCACTGAAGATGTCCTGC
AAGGCTTCTGGTTATTCATTCACTGACTACATCATACTCTGGGTGAAGCAGAACCATGGAAAG
AGCCTTGAGTGGATTGGACATATTGATCCTTACTATGGTAGTTCTAACTACAATCTGAAATTCA
AGGGCAAGGCCACATTGACTGTAGACAAATCTTCCAGCACAGCCTACATGCAGCTCAACAGT
CTGACATCTGAGGACTCTGCAGTCTATTACTGTGGAAGATCTAAGAGGGACTACTTTGACTAC
TGGGGCCAAGGCACCACTCTCACAGTTTCCTCAGCCTCCACCAAGGGCCCATCGGTCTTCCCC
CTGGCACCCTCCTCCAAGAGCACCTCTGGCGGCACAGCGGCCCTGGGCTGCCTGGTCAAGGAC
TACTTCCCCGAACCGGTGACGGTGTCGTGGAACTCAGGCGCCCTGACCAGCGGCGTGCACACC
TTCCCGGCTGTCCTACAGTCCTCAGGACTCTACTCCCTCAGCAGCGTGGTGACCGTGCCCTCCA
GCAGCTTGGGCACCCAGACCTACATCTGCAACGTGAATCACAAGCCCAGCAACACCAAGGTG
GACAAGAGAGTTGGTGAGAGGCCAGCACAGGGAGGGAGGGTGTCTGCTGGAAGCCAGGCTC
AGCGCTCCTGCCTGGACGCATCCCGGCTATGCAGTCCCAGTCCAGGGCAGCAAGGCAGGCCC
CGTCTGCCTCTTCACCCGGAGGCCTCTGCCCGCCCCACTCATGCTCAGGGAGAGGGTCTTCTG
GCTTTTTCCCCAGGCTCTGGGCAGGCACAGGCTAGGTGCCCCTAACCCAGGCCCTGCACACAA
AGGGGCAGGTGCTGGGCTCAGACCTGCCAAGAGCCATATCCGGGAGGACCCTGCCCCTGACC
TAAGCCCACCCCAAAGGCCAAACTCTCCACTCCCTCAGCTCGGACACCTTCTCTCCTCCCAGA
TTCCAGTAACTCCCAATCTTCTCTCTGCAGAGCCCAAATCTTGTGACAAAACTCACACATGCCC
ACCGTGCCCAGGTAAGCCAGCCCAGGCCTCGCCCTCCAGCTCAAGGCGGGACAGGTGCCCTA
GAGTAGCCTGCATCCAGGGACAGGCCCCAGCCGGGTGCTGACACGTCCACCTCCATCTCTTCC
TCAGCACCTGAACTCCTGGGGGGACCGTCAGTCTTCCTCTTCCCCCCAAAACCCAAGGACACC
CTCATGATCTCCCGGACCCCTGAGGTCACATGCGTGGTGGTGGACGTGAGCCACGAAGACCCT
GAGGTCAAGTTCAACTGGTACGTGGACGGCGTGGAGGTGCATAATGCCAAGACAAAGCCGCG
GGAGGAGCAGTACAACAGCACGTACCGTGTGGTCAGCGTCCTCACCGTCCTGCACCAGGACT
GGCTGAATGGCAAGGAGTACAAGTGCAAGGTCTCCAACAAAGCCCTCCCAGCCCCCATCGAG
AAAACCATCTCCAAAGCCAAAGGTGGGACCCGTGGGGTGCGAGGGCCACATGGACAGAGGCC
GGCTCGGCCCACCCTCTGCCCTGAGAGTGACCGCTGTACCAACCTCTGTCCCTACAGGGCAGC
CCCGAGAACCACAGGTGTACACCCTGCCCCCATCCCGGGAGGAGATGACCAAGAACCAGGTC
AGCCTGACCTGCCTGGTCAAAGGCTTCTATCCCAGCGACATCGCCGTGGAGTGGGAGAGCAAT
GGGCAGCCGGAGAACAACTACAAGACCACGCCTCCCGTGCTGGACTCCGACGGCTCCTTCTTC
CTCTATAGCAAGCTCACCGTGGACAAGAGCAGGTGGCAGCAGGGGAACGTCTTCTCATGCTCC
GTGATGCATGAGGCTCTGCACAACCACTACACGCAGAAGAGCCTCTCCCTGTCCCCGGGTAAA
TGA

FIGURE 1C: A schematic representation of the heavy chain of antibody chC2aB7-hG1.

FIGURE 1D
Light Chain (human Ck) (SEQ ID NO. 4)
MGWSCIILFLVATATGVHSRDIQMTQSPSSMYASLGERVTITCKASQDINSYL
SWFQQKPGKSPKTLIYRANRLVDGVPSRFSGSGSGQDYSLTISSLEYEDMGIY
YCLQYDEFPYTFGGGTKLEIKRTVAAPSVFIFPPSDEQLKSGTASVVCLLNN
FYPREAKVQWKVDNALQSGNSQESVTEQDSKDSTYSLSSTLTLSKADYE
KHKVYACEVTHQGLSSPVTKSFNRGEC

FIGURE 1E
(SEQ ID NO. 5)
ATGGGATGGAGCTGTATCATCCTCTTCTTGGTAGCAACAGCTACAGGTGT
CCACTCTAGAGACATCCAGATGACACAGTCTCCATCTTCCATGTATGCATC
TCTAGGAGAGAGAGTCACTATCACTTGCAAGGCGAGTCAGGACATTAATA
GCTATTTAAGCTGGTTCCAGCAGAAACCAGGGAAATCTCCTAAGACCCTG
ATCTATCGTGCAAACAGATTGGTAGATGGGGTTCCATCAAGGTTCAGTGG
CAGTGGATCTGGGCAAGATTATTCTCTCACCATCAGCAGCCTGGAGTATG
AAGATATGGGAATTTATTATTGTCTACAGTATGATGAGTTTCCGTACACGT
TCGGAGGGGGGACCAAGCTGGAAATAAAACGGACTGTGGCTGCACCATC
TGTCTTCATCTTCCCGCCATCTGATGAGCAGTTGAAATCTGGAACTGCCTC
TGTTGTGTGCCTGCTGAATAACTTCTATCCAGAGAGGCCAAAGTACAGT
GGAAGGTGGATAACGCCCTCCAATCGGGTAACTCCCAGGAGAGTGTCAC
AGAGCAGGACAGCAAGGACAGCACCTACAGCCTCAGCAGCACCCTGACG
CTGAGCAAAGCAGACTACGAGAAACACAAAGTCTACGCCTGCGAAGTCA
CCCATCAGGGCCTGAGCTCGCCCGTCACAAAGAGCTTCAACAGGGGAGA
GTGTTAA

FIGURE 1F: A schematic representation of the light chain of antibody chC2aB7-hG1.

```
—HindIII                                                    Xbal
|                                                            |
AAGCTTGCCGCCACCATGGGATGGAGCTGTATCATCCTCTTCTTGGTAGCAACAGCTACAGGTGTCCACTCTAGAGACATCCAGATGACACAGTCTCCATCTTCCATGTATGCATCTCTA 120
         M  G  W  S  C  I  I  L  F  L  V  A  T  A  T  G  V  H  S  R  D  I  Q  M  T  Q  S  P  S  S  M  Y  A  S  L
                                            ——————————————— c2aB7Vk ———————————————
                                                                                                                    Pstl
                                                                                                                     |
GGAGAGAGAGTCACTATCACTTGCAAGGCGAGTCAGGACATTAATAGCTATTTAAGCTGGTTCCAGCAGAAACCAGGGAAATCTCCTAAGACCCTGATCTATCGTGCAAACAGATTGGTA 240
  G  E  R  V  T  I  T  C  K  A  S  Q  D  I  N  S  Y  L  S  W  F  Q  Q  K  P  G  K  S  P  K  T  L  I  Y  R  A  N  R  L  V
                                            ——————————————— c2aB7Vk ———————————————
       Pstl
        |
GATGGGGTTCCATCAAGGTTCAGTGGCAGTGGATCTGGGCAAGATTATTCTCTCACCATCAGCAGCCTGGAGTATGAAGATATGGGAATTTATTATTGTCTACAGTATGATGAGTTTCCG 360
  D  G  V  P  S  R  F  S  G  S  G  S  G  Q  D  Y  S  L  T  I  S  S  L  E  Y  E  D  M  G  I  Y  Y  C  L  Q  Y  D  E  F  P
                                            ——————————————— c2aB7Vk ———————————————
TACACGTTCGGAGGGGGGACCAAGCTGGAAATAAAACGGACTGTGGCTGCACCATCTGTCTTCATCTTCCCGCCATCTGATGAGCAGTTGAAATCTGGAACTGCCTCTGTTGTGTGCCTG 480
  Y  T  F  G  G  G  T  K  L  E  I  K  R  T  V  A  A  P  S  V  F  I  F  P  P  S  D  E  Q  L  K  S  G  T  A  S  V  V  C  L
———————— c2aB7Vk ————————                                  ——————————————— hCk ———————————————
CTGAATAACTTCTATCCCAGAGAGGCCAAAGTACAGTGGAAGGTGGATAACGCCCTCCAATCGGGTAACTCCCAGGAGAGTGTCACAGAGCAGGACAGCAAGGACAGCACCTACAGCCTC 600
  L  N  N  F  Y  P  R  E  A  K  V  Q  W  K  V  D  N  A  L  Q  S  G  N  S  Q  E  S  V  T  E  Q  D  S  K  D  S  T  Y  S  L
                                            ——————————————— hCk ———————————————
AGCAGCACCCTGACGCTGAGCAAAGCAGACTACGAGAAACACAAAGTCTACGCCTGCGAAGTCACCCATCAGGGCCTGAGCTCGCCCGTCACAAAGAGCTTCAACAGGGGAGAGTGTTAA 720
  S  S  T  L  T  L  S  K  A  D  Y  E  K  H  K  V  Y  A  C  E  V  T  H  Q  G  L  S  S  P  V  T  K  S  F  N  R  G  E  C
                                            ——————————————— hCk ———————————————
```

FIGURE 2A chC2aB7-hG2G4
Heavy chain (SEQ ID NO. 7)

MGWSCIILFLVATATGVHS*L*EVQLQQSGPELVKPGASLKMSCKASGYSFT
DYIILWVKQNHGKSLEWIGHIDPYYGSSNYNLKFKGKATLTVDKSSSTAY
MQLNSLTSEDSAVYYCGRSKRDYFDYWGQGTTLTVSSASTKGPSVFPLA
PCSRSTSESTAALGCLVKDYFPEPVTVSWNSGALTSGVHTFPAVLQSS
GLYSLSSVVTVPSSNFGTQTYTCNVDHKPSNTKVDKTVERKCCVECP
PCPAPPVAGPSVFLFPPKPKDTLMISRTPEVTCVVVDVSQEDPEVQFN
WYVDGVEVHNAKTKPREEQFNSTYRVVSVLTVLHQDWLNGKEYKC
KVSNKGLPSSIEKTISKAKGQPREPQVYTLPPSQEEMTKNQVSLTCLV
KGFYPSDIAVEWESNGQPENNYKTTPPVLDSDGSFFLYSRLTVDKSR
WQEGNVFSCSVMHEALHNHYTQKSLSLSLGK

FIGURE 2B

(SEQ ID NO. 8) (genomic sequence hG2G4)

ATGGGATGGAGCTGTATCATCCTCTTCTTGGTAGCAACAGCTACAGGTGTCCACTCCCTCGAG
GTCCAGCTGCAACAGTCTGGACCTGAGCTGGTGAAGCCTGGGGCTTCACTGAAGATGTCCTGC
AAGGCTTCTGGTTATTCATTCACTGACTACATCATACTCTGGGTGAAGCAGAACCATGGAAAG
AGCCTTGAGTGGATTGGACATATTGATCCTTACTATGGTAGTTCTAACTACAATCTGAAATTCA
AGGGCAAGGCCACATTGACTGTAGACAAATCTTCCAGCACAGCCTACATGCAGCTCAACAGT
CTGACATCTGAGGACTCTGCAGTCTATTACTGTGGAAGATCTAAGAGGGACTACTTTGACTAC
TGGGGCCAAGGCACCACTCTCACAGTTTCCTCAGCCTCCACCAAGGGCCCATCCGTCTTCCCC
CTGGCGCCCTGCTCCAGGAGCACCTCCGAGAGCACAGCCGCCCTGGGCTGCCTGGTCAAGGA
CTACTTCCCCGAACCGGTGACGGTGTCGTGGAACTCAGGCGCCCTGACCAGCGGCGTGCACAC
CTTCCCGGCTGTCCTACAGTCCTCAGGACTCTACTCCCTCAGCAGCGTGGTGACCGTGCCCTCC
AGCAACTTCGGCACCCAGACCTACACCTGCAACGTAGATCACAAGCCCAGCAACACCAAGGT
GGACAAGACAGTTGGTGAGAGGCCAGCTCAGGGAGGGAGGGTGTCTGCTGGAAGCCAGGCTC
AGCCCTCCTGCCTGGACGCACCCCGGCTGTGCAGCCCCAGCCCAGGGCAGCAAGGCAGGCCC
CATCTGTCTCCTCACCCGGAGGCCTCTGCCCGCCCCACTCATGCTCAGGGAGAGGGTCTTCTG
GCTTTTTCCACCAGGCTCCAGGCAGGCACAGGCTGGGTGCCCCTACCCCAGGCCCTTCACACA
CAGGGGCAGGTGCTTGGCTCAGACCTGCCAAAAGCCATATCCGGGAGGACCCTGCCCCTGAC
CTAAGCCGACCCCAAAGGCCAAACTGTCCACTCCCTCAGCTCGGACACCTTCTCTCCTCCCAG
ATCCGAGTAACTCCCAATCTTCTCTCTGCAGAGCGCAAATGTTGTGTCGAGTGCCCACCGTGC
CCAGGTAAGCCAGCCCAGGCCTCGCCCTCCAGCTCAAGGCGGGACAGGTGCCCTAGAGTAGC
CTGCATCCAGGGACAGGCCCCAGCTGGGTGCTGACACGTCCACCTCCATCTCTTCCTCAGCAC
CACCTGTGGCAGGACCGTCAGTCTTCCTCTTCCCCCCAAAACCCAAGGACACCCTCATGATCT
CCCGGACCCCTGAGGTCACGTGCGTGGTGGTGGACGTGAGCCAGGAAGACCCCGAGGTCCAG
TTCAACTGGTACGTGGATGGCGTGGAGGTGCATAATGCCAAGACAAAGCCGCGGGAGGAGCA
GTTCAACAGCACGTACCGTGTGGTCAGCGTCCTCACCGTCCTGCACCAGGACTGGCTGAACGG
CAAGGAGTACAAGTGCAAGGTCTCCAACAAAGGCCTCCCGTCCTCCATCGAGAAAACCATCT
CCAAAGCCAAAGGTGGGACCCACGGGGTGCGAGGGCCACATGGACAGAGGTCAGCTCGGCCC
ACCCTCTGCCCTGGGAGTGACCGCTGTGCCAACCTCTGTCCCTACAGGGCAGCCCCGAGAGCC
ACAGGTGTACACCCTGCCCCCATCCCAGGAGGAGATGACCAAGAACCAGGTCAGCCTGACCT
GCCTGGTCAAAGGCTTCTACCCCAGCGACATCGCCGTGGAGTGGGAGAGCAATGGGCAGCCG
GAGAACAACTACAAGACCACGCCTCCCGTGCTGGACTCCGACGGCTCCTTCTTCCTCTACAGC
AGGCTAACCGTGGACAAGAGCAGGTGGCAGGAGGGGAATGTCTTCTCATGCTCCGTGATGCA
TGAGGCTCTGCACAACCACTACACACAGAAGAGCCTCTCCCTGTCTCTGGGTAAATGA

FIGURE 2C: A schematic representation of the heavy chain of antibody chC2aB7-hG2G4 (amino acids 1-337).

FIGURE 2D
Light Chain (human Cκ) (SEQ ID NO. 11)
MGWSCIILFLVATATGVHSRDIQMTQSPSSMYASLGERVTITCKASQDINS
YLSWFQQKPGKSPKTLIYRANRLVDGVPSRFSGSGSGQDYSLTISSLEYED
MGIYYCLQYDEFPYTFGGGTKLEIKRTVAAPSVFIFPPSDEQLKSGTASV
VCLLNNFYPREAKVQWKVDNALQSGNSQESVTEQDSKDSTYSLSSTL
TLSKADYEKHKVYACEVTHQGLSSPVTKSFNRGEC

FIGURE 2E
(SEQ ID NO. 12)
ATGGGATGGAGCTGTATCATCCTCTTCTTGGTAGCAACAGCTACAGGT
GTCCACTCTAGAGACATCCAGATGACACAGTCTCCATCTTCCATGTAT
GCATCTCTAGGAGAGAGTCACTATCACTTGCAAGGCGAGTCAGGA
CATTAATAGCTATTTAAGCTGGTTCCAGCAGAAACCAGGGAAATCTCC
TAAGACCCTGATCTATCGTGCAAACAGATTGGTAGATGGGGTTCCATC
AAGGTTCAGTGGCAGTGGATCTGGGCAAGATTATTCTCTCACCATCAG
CAGCCTGGAGTATGAAGATATGGGAATTTATTATTGTCTACAGTATGA
TGAGTTTCCGTACACGTTCGGAGGGGGGACCAAGCTGGAAATAAAAC
GGACTGTGGCTGCACCATCTGTCTTCATCTTCCCGCCATCTGATGAGCA
GTTGAAATCTGGAACTGCCTCTGTTGTGTGCCTGCTGAATAACTTCTAT
CCCAGAGAGGCCAAAGTACAGTGGAAGGTGGATAACGCCCTCCAATC
GGGTAACTCCCAGGAGAGTGTCACAGAGCAGGACAGCAAGGACAGCA
CCTACAGCCTCAGCAGCACCCTGACGCTGAGCAAAGCAGACTACGAG
AAACACAAAGTCTACGCCTGCGAAGTCACCCATCAGGGCCTGAGCTC
GCCCGTCACAAAGAGCTTCAACAGGGGAGAGTGTTAA

FIGURE 2F: A schematic representation of the light chain of antibody chC2aB7-hG2G4.

FIGURE 3A
hB7V3V2-hG1
Heavy chain (SEQ ID NO. 15)

MGWSRIFLFLLSIIAGVHCQVQLQQSGSELKKPGASVKISCKASGYSFTDY
IILWVRQNPGKGLEWIGHIDPYYGSSNYNLKFKGRVTITADQSTTTAYME
LSSLRSEDTAVYYCGRSKRDYFDYWGQGTTLTVSSASTKGPSVFPLAPSS
KSTSGGTAALGCLVKDYFPEPVTVSWNSGALTSGVHTFPAVLQSSGL
YSLSSVVTVPSSSLGTQTYICNVNHKPSNTKVDKRVEPKSCDKTHTCP
PCPAPELLGGPSVFLFPPKPKDTLMISRTPEVTCVVVDVSHEDPEVKF
NWYVDGVEVHNAKTKPREEQYNSTYRVVSVLTVLHQDWLNGKEYK
CKVSNKALPAPIEKTISKAKGQPREPQVYTLPPSREEMTKNQVSLTCL
VKGFYPSDIAVEWESNGQPENNYKTTPPVLDSDGSFFLYSKLTVDKSR
WQQGNVFSCSVMHEALHNHYTQKSLSLSPGK

FIGURE 3B (SEQ ID NO. 16) (cDNA hG1)

ATGGGATGGAGCCGGATCTTTCTCTTCCTCCTGTCAATAATTGCAGGTG
TCCATTGCCAGGTCCAGCTGCAACAGTCTGGATCTGAGCTGAAGAAGC
CTGGGGCTTCAGTGAAGATCTCCTGCAAGGCTTCTGGTTATTCATTCAC
TGACTACATCATACTCTGGGTGAGGCAGAACCCTGGAAAGGGCCTTGA
GTGGATTGGACATATTGATCCTTACTATGGTAGTTCTAACTACAATCTG
AAATTCAAGGGCAGAGTGACAATCACCGCCGACCAGTCTACCACCAC
AGCCTACATGGAGCTCTCCAGTCTGAGATCTGAGGACACTGCAGTCTA
TTACTGTGGAAGATCTAAGAGGGACTACTTTGACTACTGGGGCCAAGG
CACCACTCTCACAGTTTCCTCAGCCTCCACCAAGGGCCCATCGGTCTTC
CCGCTAGCACCCTCCTCCAAGAGCACCTCTGGGGGCACAGCGGCCCTG
GGCTGCCTGGTCAAGGACTACTTCCCCGAACCGGTGACGGTGTCGTGG
AACTCAGGCGCCCTGACCAGCGGCGTGCACACCTTCCCGGCTGTCCTA
CAGTCCTCAGGACTCTACTCCCTCAGCAGCGTGGTGACCGTGCCCTCC
AGCAGCTTGGGCACCCAGACCTACATCTGCAACGTGAATCACAAGCCC
AGCAACACCAAGGTGGACAAGAGAGTTGAGCCCAAATCTTGTGACAA
AACTCACACATGCCCACCGTGCCCAGCACCTGAACTCCTGGGGGGACC
GTCAGTCTTCCTCTTCCCCCCAAAACCCAAGGACACCCTCATGATCTCC
CGGACCCCTGAGGTCACATGCGTGGTGGTGGACGTGAGCCACGAAGA
CCCTGAGGTCAAGTTCAACTGGTACGTGGACGGCGTGGAGGTGCATAA
TGCCAAGACAAAGCCGCGGGAGGAGCAGTACAACAGCACGTACCGTG
TGGTCAGCGTCCTCACCGTCCTGCACCAGGACTGGCTGAATGGCAAGG
AGTACAAGTGCAAGGTCTCCAACAAAGCCCTCCCAGCCCCCATCGAG
AAAACCATCTCCAAAGCCAAAGGGCAGCCCCGAGAACCACAGGTGTA
CACCCTGCCCCCATCCCGGGAGGAGATGACCAAGAACCAGGTCAGCC
TGACCTGCCTGGTCAAAGGCTTCTATCCCAGCGACATCGCCGTGGAGT
GGGAGAGCAATGGGCAGCCGGAGAACAACTACAAGACCACGCCTCCC
GTGCTGGACTCCGACGGCTCCTTCTTCCTCTACAGCAAGCTCACCGTG
GACAAGAGCAGGTGGCAGCAGGGGAACGTCTTCTCATGCTCCGTGAT
GCATGAGGCTCTGCACAACCACTACACGCAGAAGAGCCTCTCCCTGTC
TCCGGGTAAATGA

FIGURE 3C: A schematic representation of the heavy chain of antibody hB7V3V2-hG1.

```
CATGGGATGGAGCCGGATCTTTCTCTTCCTCCTGTCAATAATTGCAGGTGTCCATTGCCAGGTCCAGCTGCAACAGTCTGGATCTGAGCTGAAGAAGCCTGGGGCTTCAGTGAAGATCTC 5160
 M  G  W  S  R  I  F  L  F  L  L  S  I  I  A  G  V  H  C  Q  V  Q  L  Q  Q  S  G  S  E  L  K  K  P  G  A  S  V  K  I  S
|-------------------- leader --------------------|            |------------------------ hB7V3 Vh ------------------------
CTGCAAGGCTTCTGGTTATTCATTCACTGACTACATCATACTCTGGGTGAGGCAGAACCCTGGAAAGGGCCTTGAGTGGATTGGACATATTGATCCTTACTATGGTAGTTCTAACTACAA 5280
 C  K  A  S  G  Y  S  F  T  D  Y  I  I  L  W  V  R  Q  N  P  G  K  G  L  E  W  I  G  H  I  D  P  Y  Y  G  S  S  N  Y  N
------------------------------------------------- hB7V3 Vh ---
TCTGAAATTCAAGGGCAGAGTGACAATCACCGCCGACCAGTCTACCACCACAGCCTACATGGAGCTCTCCAGTCTGAGATCTGAGGACACTGCAGTCTATTACTGTGGAAGATCTAAGAG 5400
 L  K  F  K  G  R  V  T  I  T  A  D  Q  S  T  T  T  A  Y  M  E  L  S  S  L  R  S  E  D  T  A  V  Y  Y  C  G  R  S  K  R
---------------------------- hB7V3 Vh ----------------------------
GGACTACTTTGACTACTGGGGCCAAGGCACCACTCTCACAGTTTCCTCAGCCTCCACCAAGGGCCCATCGGTCTTCCCGCTAGCACCCTCCTCCAAGAGCACCTCTGGGGGCACAGCGGC 5520
 D  Y  F  D  Y  W  G  Q  G  T  T  L  T  V  S  S  A  S  T  K  G  P  S  V  F  P  L  A  P  S  S  K  S  T  S  G  G  T  A  A
-------------------- hB7V3 Vh --------------------|            |------------------------- hG1 -------------------------
CCTGGGCTGCCTGGTCAAGGACTACTTCCCCGAACCGGTGACGGTGTCGTGGAACTCAGGCGCCCTGACCAGCGGCGTGCACACCTTCCCGGCTGTCCTACAGTCCTCAGGACTCTACTC 5640
 L  G  C  L  V  K  D  Y  F  P  E  P  V  T  V  S  W  N  S  G  A  L  T  S  G  V  H  T  F  P  A  V  L  Q  S  S  G  L  Y  S
--------------------------------------------------- hG1 ---
CCTCAGCAGCGTGGTGACCGTGCCCTCCAGCAGCTTGGGCACCCAGACCTACATCTGCAACGTGAATCACAAGCCCAGCAACACCAAGGTGGACAAGAGAGTTGAGCCCAAATCTTGTGA 5760
 L  S  S  V  V  T  V  P  S  S  S  L  G  T  Q  T  Y  I  C  N  V  N  H  K  P  S  N  T  K  V  D  K  R  V  E  P  K  S  C  D
--------------------------------------------------- hG1 ---
CAAAACTCACACATGCCCACCGTGCCCAGCACCTGAACTCCTGGGGGGACCGGTCAGTCTTCCTCTTCCCCCCAAAACCCAAGGACACCCTCATGATCTCCCGGACCCCTGAGGTCACATG 5880
 K  T  H  T  C  P  P  C  P  A  P  E  L  L  G  G  P  S  V  F  L  F  P  P  K  P  K  D  T  L  M  I  S  R  T  P  E  V  T  C
--------------------------------------------------- hG1 ---
CGTGGTGGTGGACGTGAGCCACGAAGACCCTGAGGTCAAGTTCAACTGGTACGTGGACGGCGTGGAGGTGCATAATGCCAAGACAAAGCCGCGGGAGGAGCAGTACAACAGCACGTACCG 6000
 V  V  V  D  V  S  H  E  D  P  E  V  K  F  N  W  Y  V  D  G  V  E  V  H  N  A  K  T  K  P  R  E  E  Q  Y  N  S  T  Y  R
--------------------------------------------------- hG1 ---
TGTGGTCAGCGTCCTCACCGTCCTGCACCAGGACTGGCTGAATGGCAAGGAGTACAAGTGCAAGGTCTCCAACAAAGCCCTCCCAGCCCCCATCGAGAAAACCATCTCCAAAGCCAAAGG 6120
 V  V  S  V  L  T  V  L  H  Q  D  W  L  N  G  K  E  Y  K  C  K  V  S  N  K  A  L  P  A  P  I  E  K  T  I  S  K  A  K  G
--------------------------------------------------- hG1 ---
GCAGCCCCGAGAACCACAGGTGTACACCCTGCCCCCATCCCGGGAGGAGATGACCAAGAACCAGGTCAGCCTGACCTGCCTGGTCAAAGGCTTCTATCCCAGCGACATCGCCGTGGAGTG 6240
 Q  P  R  E  P  Q  V  Y  T  L  P  P  S  R  E  E  M  T  K  N  Q  V  S  L  T  C  L  V  K  G  F  Y  P  S  D  I  A  V  E  W
--------------------------------------------------- hG1 ---
GGAGAGCAATGGGCAGCCGGAGAACAACTACAAGACCACGCCTCCCGTGCTGGACTCCGACGGCTCCTTCTTCCTCTACAGCAAGCTCACCGTGGACAAGAGCAGGTGGCAGCAGGGGAA 6360
 E  S  N  G  Q  P  E  N  N  Y  K  T  T  P  P  V  L  D  S  D  G  S  F  F  L  Y  S  K  L  T  V  D  K  S  R  W  Q  Q  G  N
--------------------------------------------------- hG1 ---
CGTCTTCTCATGCTCCGTGATGCATGAGGCTCTGCACAACCACTACACGCAGAAGAGCCTCTCCCTGTCTCCGGGTAAATGA 6442
 V  F  S  C  S  V  M  H  E  A  L  H  N  H  Y  T  Q  K  S  L  S  L  S  P  G  K  .
--------------------------------------------------- hG1 ---
```

FIGURE 3D
Light Chain (human Ck) (SEQ ID NO. 18)
MDMRVSAQLLGLLLLWLSGARCDIQMTQSPSSLSASIGDRVTITCKASQD
INSYLSWFQQKPGKAPKLLIYRANRLVDGVPSRFSGSGSGTDYTLTISSLQ
PEDFAVYYCLQYDEFPYTFGGGTKLEIKRTVAAPSVFIFPPSDEQLKSGT
ASVVCLLNNFYPREAKVQWKVDNALQSGNSQESVTEQDSKDSTYSLS
STLTLSKADYEKHKVYACEVTHQGLSSPVTKSFNRGEC FIGURE 3E
(SEQ ID NO. 19)
ATGGACATGAGGGTCTCTGCTCAGCTCCTGGGGCTCCTGCTGCTCTGG
CTCTCAGGGGCCAGGTGTGACATCCAGATGACACAGTCTCCATCTTCC
CTGTCTGCATCTATAGGAGACAGAGTCACTATCACTTGCAAGGCGAGT
CAGGACATTAATAGCTATTTAAGCTGGTTCCAGCAGAAACCAGGGAA
AGCTCCTAAGCTGCTGATCTATCGTGCAAACAGATTGGTAGATGGGGT
TCCATCAAGGTTCAGTGGCAGTGGATCTGGGACAGATTATACTCTCAC
CATCAGCAGCCTGCAGCCTGAAGATTTCGCAGTTTATTATTGTCTACA
GTATGATGAGTTTCCGTACACGTTCGGAGGGGGGACCAAGCTGGAAAT
AAAACGTACGGTGGCTGCACCATCTGTCTTCATCTTCCCGCCATCTGAT
GAGCAGTTGAAATCTGGAACTGCCTCTGTTGTGTGCCTGCTGAATAAC
TTCTATCCCAGAGAGGCCAAAGTACAGTGGAAGGTGGATAACGCCCTC
CAATCGGGTAACTCCCAGGAGAGTGTCACAGAGCAGGACAGCAAGGA
CAGCACCTACAGCCTCAGCAGCACCCTGACGCTGAGCAAAGCAGACT
ACGAGAAACACAAAGTCTACGCCTGCGAAGTCACCCATCAGGGCCTG
AGCTCGCCCGTCACAAAGAGCTTCAACAGGGGAGAGTGTTAG

FIGURE 3F: A schematic representation of the light chain of antibody hB7V3V2-hG1.

```
TTTCCATGGGTCTTTTCTGCAGTCACCGTCCTTGACACGAAGCTTGCCGCCACCATGGACATGAGGGTCTCTGCTCAGCTCCTGGGGCTCCTGCTGCTCTGGCTCTCAGGGGCCAGGTGT 11400
                                              M  D  M  R  V  S  A  Q  L  L  G  L  L  L  L  W  L  S  G  A  R  C
                                              |─────────────────────────────── leader ───────────────────────────|

GACATCCAGATGACACAGTCTCCATCTTCCCTGTCTGCATCTATAGGAGACAGAGTCACTATCACTTGCAAGGCGAGTCAGGACATTAATAGCTATTTAAGCTGGTTCCAGCAGAAACCA 11520
 D  I  Q  M  T  Q  S  P  S  S  L  S  A  S  I  G  D  R  V  T  I  T  C  K  A  S  Q  D  I  N  S  Y  L  S  W  F  Q  Q  K  P
|──────────────────────────────────────────────────── V2Vk ─────────────────────────────────────────────────────────────
                                              PstI                                  PstI

GGGAAAGCTCCTAAGCTGCTGATCTATCGTGCAAACAGATTGGTAGATGGGGTTCCATCAAGGTTCAGTGGCAGTGGATCTGGGACAGATTATACTCTCACCATCAGCAGCCTGCAGCCT 11640
 G  K  A  P  K  L  L  I  Y  R  A  N  R  L  V  D  G  V  P  S  R  F  S  G  S  G  S  G  T  D  Y  T  L  T  I  S  S  L  Q  P
─────────────────────────────────────────────────── V2V ──────────────────────────────────────────────────────────────
                                                                              BsiWI

GAAGATTTCGCAGTTTATTATTGTCTACAGTATGATGAGTTTCCGTACACGTTCGGAGGGGGGACCAAGCTGGAAATAAAACGTACGGTGGCTGCACCATCTGTCTTCATCTTCCCGCCA 11760
 E  D  F  A  V  Y  Y  C  L  Q  Y  D  E  F  P  Y  T  F  G  G  G  T  K  L  E  I  K  R  T  V  A  A  P  S  V  F  I  F  P  P
───────────────────────────── V2V ─────────────────────────────────── |──────────────────── hCk ─────────────────────

TCTGATGAGCAGTTGAAATCTGGAACTGCCTCTGTTGTGTGCCTGCTGAATAACTTCTATCCCAGAGAGGCCAAAGTACAGTGGAAGGTGGATAACGCCCTCCAATCGGGTAACTCCCAG 11880
 S  D  E  Q  L  K  S  G  T  A  S  V  V  C  L  L  N  N  F  Y  P  R  E  A  K  V  Q  W  K  V  D  N  A  L  Q  S  G  N  S  Q
───────────────────────────────────────────────────── hCk ──────────────────────────────────────────────────────────

GAGAGTGTCACAGAGCAGGACAGCAAGGACAGCACCTACAGCCTCAGCAGCACCCTGACGCTGAGCAAAGCAGACTACGAGAAACACAAAGTCTACGCCTGCGAAGTCACCCATCAGGGC 12000
 E  S  V  T  E  Q  D  S  K  D  S  T  Y  S  L  S  S  T  L  T  L  S  K  A  D  Y  E  K  H  K  V  Y  A  C  E  V  T  H  Q  G
──────────────────────────────────────────────────── hCk ───────────────────────────────────────────────────────────

CTGAGCTCGCCCGTCACAAAGAGCTTCAACAGGGGAGAGTGTTAG 12045
 L  S  S  P  V  T  K  S  F  N  R  G  E  C  .
─────────────────── hCk ──────────────────|
```

FIGURE 4A hB7V3V2-hG2G4
Heavy chain (SEQ ID NO. 21)

<u>MGWSRIFLFLLSIIAGVHC</u>QVQLQQSGSELKKPGASVKISCKASGYSFTDY
IILWVRQNPGKGLEWIGHIDPYYGSSNYNLKFKGRVTITADQSTTTAYME
LSSLRSEDTAVYYCGRSKRDYFDYWGQGTTLTVSS**ASTKGPSVFPLAPC
SRSTSESTAALGCLVKDYFPEPVTVSWNSGALTSGVHTFPAVLQSSGL
YSLSSVVTVPSSNFGTQTYTCNVDHKPSNTKVDKTVERKCCVECPPCP
APPVAGPSVFLFPPKPKDTLMISRTPEVTCVVVDVSQEDPEVQFNWYV
DGVEVHNAKTKPREEQFNSTYRVVSVLTVLHQDWLNGKEYKCKVSN
KGLPSSIEKTISKAKGQPREPQVYTLPPSQEEMTKNQVSLTCLVKGFY
PSDIAVEWESNGQPENNYKTTPPVLDSDGSFFLYSRLTVDKSRWQEG
NVFSCSVMHEALHNHYTQKSLSLSLGK**

FIGURE 4B

(SEQ ID NO. 22) (genomic sequence hG2G4)

ATGGGATGGAGCTGTATCATCCTCTTCTTGGTAGCAACAGCTACAGGTGTCCACTCCCTCGAG
GTCCAGCTGCAACAGTCTGGACCTGAGCTGGTGAAGCCTGGGGCTTCACTGAAGATGTCCTGC
AAGGCTTCTGGTTATTCATTCACTGACTACATCATACTCTGGGTGAAGCAGAACCATGGAAAG
AGCCTTGAGTGGATTGGACATATTGATCCTTACTATGGTAGTTCTAACTACAATCTGAAATTCA
AGGGCAAGGCCACATTGACTGTAGACAAATCTTCCAGCACAGCCTACATGCAGCTCAACAGT
CTGACATCTGAGGACTCTGCAGTCTATTACTGTGGAAGATCTAAGAGGGACTACTTTGACTAC
TGGGGCCAAGGCACCACTCTCACAGTTTCCTCAGCCTCCACCAAGGGCCCATCCGTCTTCCCC
CTGGCGCCCTGCTCCAGGAGCACCTCCGAGAGCACAGCCGCCCTGGGCTGCCTGGTCAAGGA
CTACTTCCCCGAACCGGTGACGGTGTCGTGGAACTCAGGCGCCCTGACCAGCGGCGTGCACAC
CTTCCCGGCTGTCCTACAGTCCTCAGGACTCTACTCCCTCAGCAGCGTGGTGACCGTGCCCTCC
AGCAACTTCGGCACCCAGACCTACACCTGCAACGTAGATCACAAGCCCAGCAACACCAAGGT
GGACAAGACAGTTGGTGAGAGGCCAGCTCAGGGAGGGAGGGTGTCTGCTGGAAGCCAGGCTC
AGCCCTCCTGCCTGGACGCACCCCGGCTGTGCAGCCCAGCCCAGGGCAGCAAGGCAGGCCC
CATCTGTCTCCTCACCCGGAGGCCTCTGCCCGCCCCACTCATGCTCAGGGAGAGGGTCTTCTG
GCTTTTTCCACCAGGCTCCAGGCAGGCACAGGCTGGGTGCCCCTACCCCAGGCCCTTCACACA
CAGGGGCAGGTGCTTGGCTCAGACCTGCCAAAAGCCATATCCGGGAGGACCCTGCCCCTGAC
CTAAGCCGACCCCAAAGGCCAAACTGTCCACTCCCTCAGCTCGGACACCTTCTCTCCTCCCAG
ATCCGAGTAACTCCCAATCTTCTCTCTGCAGAGCGCAAATGTTGTGTCGAGTGCCCACCGTGC
CCAGGTAAGCCAGCCCAGGCCTCGCCCTCCAGCTCAAGGCGGGACAGGTGCCCTAGAGTAGC
CTGCATCCAGGGACAGGCCCCAGCTGGGTGCTGACACGTCCACCTCCATCTCTTCCTCAGCAC
CACCTGTGGCAGGACCGTCAGTCTTCCTCTTCCCCCCAAAACCCAAGGACACCCTCATGATCT
CCCGGACCCCTGAGGTCACGTGCGTGGTGGTGGACGTGAGCCAGGAAGACCCCGAGGTCCAG
TTCAACTGGTACGTGGATGGCGTGGAGGTGCATAATGCCAAGACAAAGCCGCGGGAGGAGCA
GTTCAACAGCACGTACCGTGTGGTCAGCGTCCTCACCGTCCTGCACCAGGACTGGCTGAACGG
CAAGGAGTACAAGTGCAAGGTCTCCAACAAAGGCCTCCCGTCCTCCATCGAGAAAACCATCT
CCAAAGCCAAAGGTGGGACCCACGGGGTGCGAGGGCCACATGGACAGAGGTCAGCTCGGCCC
ACCCTCTGCCCTGGGAGTGACCGCTGTGCCAACCTCTGTCCCTACAGGGCAGCCCCGAGAGCC
ACAGGTGTACACCCTGCCCCCATCCCAGGAGGAGATGACCAAGAACCAGGTCAGCCTGACCT
GCCTGGTCAAAGGCTTCTACCCCAGCGACATCGCCGTGGAGTGGGAGAGCAATGGGCAGCCG
GAGAACAACTACAAGACCACGCCTCCCGTGCTGGACTCCGACGGCTCCTTCTTCCTCTACAGC
AGGCTAACCGTGGACAAGAGCAGGTGGCAGGAGGGGAATGTCTTCTCATGCTCCGTGATGCA
TGAGGCTCTGCACAACCACTACACACAGAAGAGCCTCTCCCTGTCTCTGGGTAAATGATGA

FIGURE 4C: A schematic representation of the heavy chain of antibody hB7V3V2-hG2G4.

FIGURE 4D
Light Chain (human Cκ) (SEQ ID NO. 24)
MDMRVSAQLLGLLLLWLSGARCDIQMTQSPSSLSASIGDRVTITCKASQD
INSYLSWFQQKPGKAPKLLIYRANRLVDGVPSRFSGSGSGTDYTLTISSLQ
PEDFAVYYCLQYDEFPYTFGGGTKLEIKRTVAAPSVFIFPPSDEQLKSGT
ASVVCLLNNFYPREAKVQWKVDNALQSGNSQESVTEQDSKDSTYSLS
STLTLSKADYEKHKVYACEVTHQGLSSPVTKSFNRGEC

FIGURE 4E
(SEQ ID NO. 25)
ATGGACATGAGGGTCTCTGCTCAGCTCCTGGGGCTCCTGCTGCTCTGG
CTCTCAGGGGCCAGGTGTGACATCCAGATGACACAGTCTCCATCTTCC
CTGTCTGCATCTATAGGAGACAGAGTCACTATCACTTGCAAGGCGAGT
CAGGACATTAATAGCTATTTAAGCTGGTTCCAGCAGAAACCAGGGAA
AGCTCCTAAGCTGCTGATCTATCGTGCAAACAGATTGGTAGATGGGGT
TCCATCAAGGTTCAGTGGCAGTGGATCTGGGACAGATTATACTCTCAC
CATCAGCAGCCTGCAGCCTGAAGATTTCGCAGTTTATTATTGTCTACA
GTATGATGAGTTTCCGTACACGTTCGGAGGGGGGACCAAGCTGGAAAT
AAAACGTACGGTGGCTGCACCATCTGTCTTCATCTTCCCGCCATCTGAT
GAGCAGTTGAAATCTGGAACTGCCTCTGTTGTGTGCCTGCTGAATAAC
TTCTATCCCAGAGAGGCCAAAGTACAGTGGAAGGTGGATAACGCCCTC
CAATCGGGTAACTCCCAGGAGAGTGTCACAGAGCAGGACAGCAAGGA
CAGCACCTACAGCCTCAGCAGCACCCTGACGCTGAGCAAAGCAGACT
ACGAGAAACACAAAGTCTACGCCTGCGAAGTCACCCATCAGGGCCTG
AGCTCGCCCGTCACAAAGAGCTTCAACAGGGGAGAGTGTTAG

FIGURE 4F: A schematic representation of the light chain of antibody hB7V3V2-hG2G4.

```
TTTCCATGGGTCTTTTCTGCAGTCACCGTCCTTGACACGAAGCTTGCCGCCACCATGGACATGAGGGTCTCTGCTCAGCTCCTGGGGCTCCTGCTGCTCTGGCTCTCAGGGGCCAGGTGT  11400
                                         M  D  M  R  V  S  A  Q  L  L  G  L  L  L  L  W  L  S  G  A  R  C
                                         └─────────────────── leader ───────────────────┘
GACATCCAGATGACACAGTCTCCATCTTCCCTGTCTGCATCTATAGGAGACAGAGTCACTATCACTTGCAAGGCGAGTCAGGACATTAATAGCTATTTAAGCTGGTTCCAGCAGAAACCA  11520
 D  I  Q  M  T  Q  S  P  S  S  L  S  A  S  I  G  D  R  V  T  I  T  C  K  A  S  Q  D  I  N  S  Y  L  S  W  F  Q  Q  K  P
 └──────────────────────────────────────── V2Vk ────────────────────────────────────────┘
                                                  Psrl                      Psrl
GGGAAAGCTCCTAAGCTGCTGATCTATCGTGCAAACAGATTGGTAGATGGGGTTCCATCAAGGTTCAGTGGCAGTGGATCTGGGACAGATTATACTCTCACCATCAGCAGCCTGCAGCCT  11640
 G  K  A  P  K  L  L  I  Y  R  A  N  R  L  V  D  G  V  P  S  R  F  S  G  S  G  S  G  T  D  Y  T  L  T  I  S  S  L  Q  P
 └──────────────────────────────────────── V2V ────────────────────────────────────────┘
                                                                         BsiWI
GAAGATTTCGCAGTTTATTATTGTCTACAGTATGATGAGTTTCCGTACACGTTCGGAGGGGGGACCAAGCTGGAAATAAAACGTACGGTGGCTGCACCATCTGTCTTCATCTTCCCGCCA  11760
 E  D  F  A  V  Y  Y  C  L  Q  Y  D  E  F  P  Y  T  F  G  G  G  T  K  L  E  I  K  R  T  V  A  A  P  S  V  F  I  F  P  P
 └─────────────────── V2V ───────────────────┘                              └─────────── hCk ───────────
TCTGATGAGCAGTTGAAATCTGGAACTGCCTCTGTTGTGTGCCTGCTGAATAACTTCTATCCCAGAGAGGCCAAAGTACAGTGGAAGGTGGATAACGCCCTCCAATCGGGTAACTCCCAG  11880
 S  D  E  Q  L  K  S  G  T  A  S  V  V  C  L  L  N  N  F  Y  P  R  E  A  K  V  Q  W  K  V  D  N  A  L  Q  S  G  N  S  Q
 ────────────────────────────────────────── hCk ──────────────────────────────────────────
GAGAGTGTCACAGAGCAGGACAGCAAGGACAGCACCTACAGCCTCAGCAGCACCCTGACGCTGAGCAAAGCAGACTACGAGAAACACAAAGTCTACGCCTGCGAAGTCACCCATCAGGGC  12000
 E  S  V  T  E  Q  D  S  K  D  S  T  Y  S  L  S  S  T  L  T  L  S  K  A  D  Y  E  K  H  K  V  Y  A  C  E  V  T  H  Q  G
 ────────────────────────────────────────── hCk ──────────────────────────────────────────
CTGAGCTCGCCCGTCACAAAGAGCTTCAACAGGGGAGAGTGTTAG  12045
 L  S  S  P  V  T  K  S  F  N  R  G  E  C  .
 ─────────────── hCk ───────────────┘
```

Cell surface expression of CD200 on human CD3+ cells following activation with mOKT3

FIGURE 6
Human T cells activated through T cell receptor signaling serve as sensitive targets for anti-CD200 mediated ADCC
A.
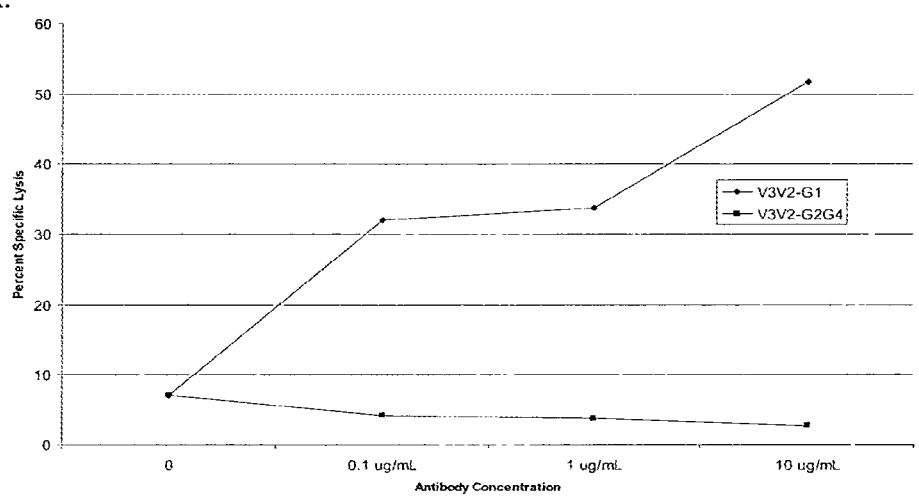
B.
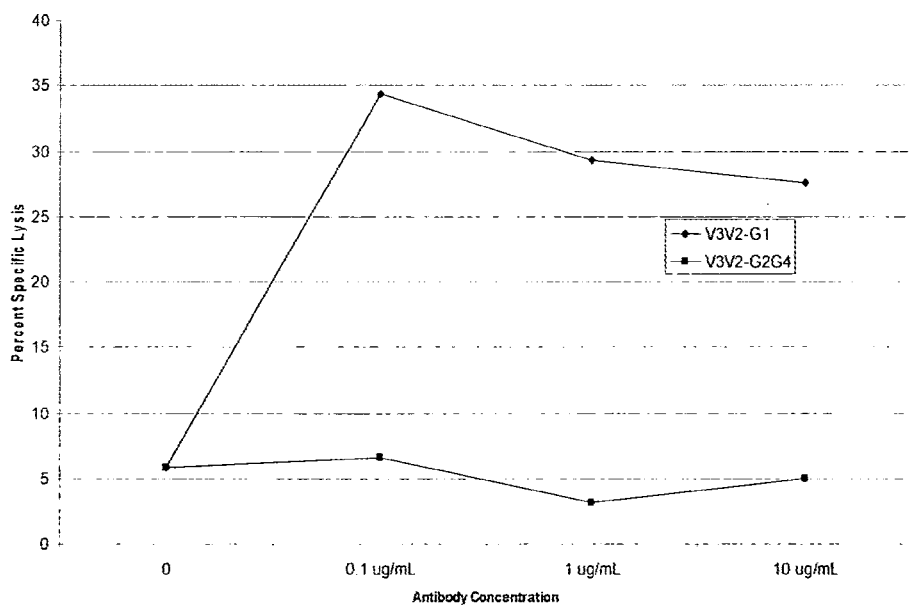

HD=high dose, LD=low dose, LT=long-term, ST=short-term
*Animals were sacrificed at the endpoint of rejection.

HD=high dose, LD=low dose, LT=long-term, ST=short-term
*Animals were sacrificed at the endpoint of rejection.

FIGURE 10

| | | |
|---|---|---|
| 1 | EVQLVESGGGLVKPGRSLKLSCAASGFTFSDYYMAWVRQAPKKGL | OX90NE |
| 1 | EVQLVESGGGLVKPGRSLKLSCAASGFTFSDYYMAWVRQAPKKGL | OX90mG2a |
| 46 | EWVASIGYEGTSTYYGDSVKGRFTISRDNAKSTLYLQMNSLRSED | OX90NE |
| 46 | EWVASIGYEGTSTYYGDSVKGRFTISRDNAKSTLYLQMNSLRSED | OX90mG2a |
| 91 | TATYYCTRLELAGVMDAWGQGASVTVSSAKTTAPSVYPLAPVCGD | OX90NE |
| 91 | TATYYCTRLELAGVMDAWGQGASVTVSSAKTTAPSVYPLAPVCGD | OX90mG2a |
| 136 | TTGSSVTLGCLVKGYFPEPVTLTWNSGSLSSGVHTFPAVLQSDLY | OX90NE |
| 136 | TTGSSVTLGCLVKGYFPEPVTLTWNSGSLSSGVHTFPAVLQSDLY | OX90mG2a |
| 181 | TLSSSVTVTSSTWPSQSITCNVAHPASSTKVDKKIEPRGPTIKPC | OX90NE |
| 181 | TLSSSVTVTSSTWPSQSITCNVAHPASSTKVDKKIEPRGPTIKPC | OX90mG2a |
| 226 | PPCKCPAPNLEGGPSVFIFPPKIKDVLMISLSPIVTCVVVDVSED | OX90NE |
| 226 | PPCKCPAPNLLGGPSVFIFPPKIKDVLMISLSPIVTCVVVDVSED | OX90mg2a |
| 271 | DPDVQISWFVNNVEVHTAQTQTHREDYNSTLRVVSALPIQHQDWM | OX90NE |
| 271 | DPDVQISWFVNNVEVHTAQTQTHREDYNSTLRVVSALPIQHQDWM | OX90mG2a |
| 316 | SGKAFACAVNNKDLPAPIERTISKPKGSVRAPQVYVLPPPEEEMT | OX90NE |
| 316 | SGKEFKCKVNNKDLPAPIERTISKPKGSVRAPQVYVLPPPEEEMT | OX90mG2a |
| 361 | KKQVTLTCMVTDFMPEDIYVEWTNNGKTELNYKNTEPVLDSDGSY | OX90NE |
| 361 | KKQVTLTCMVTDFMPEDIYVEWTNNGKTELNYKNTEPVLDSDGSY | OX90mG2a |
| 406 | FMYSKLRVEKKNWVERNSYSCSVVHEGLHNHHTTKSFSRTPGK | OX90NE |
| 406 | FMYSKLRVEKKNWVERNSYSCSVVHEGLHNHHTTKSFSRTPGK | OX90mG2a |

SEQUENCE LISTING

```
<160> NUMBER OF SEQ ID NOS: 28

<210> SEQ ID NO 1
<211> LENGTH: 465
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 1

Met Gly Trp Ser Cys Ile Ile Leu Phe Leu Val Ala Thr Ala Thr Gly
1               5                   10                  15

Val His Ser Leu Glu Val Gln Leu Gln Gln Ser Gly Pro Glu Leu Val
            20                  25                  30

Lys Pro Gly Ala Ser Leu Lys Met Ser Cys Lys Ala Ser Gly Tyr Ser
        35                  40                  45

Phe Thr Asp Tyr Ile Ile Leu Trp Val Lys Gln Asn His Gly Lys Ser
```

-continued

```
              50                  55                  60
Leu Glu Trp Ile Gly His Ile Asp Pro Tyr Tyr Gly Ser Ser Asn Tyr
 65                  70                  75                  80

Asn Leu Lys Phe Lys Gly Lys Ala Thr Leu Thr Val Asp Lys Ser Ser
                 85                  90                  95

Ser Thr Ala Tyr Met Gln Leu Asn Ser Leu Thr Ser Glu Asp Ser Ala
                100                 105                 110

Val Tyr Tyr Cys Gly Arg Ser Lys Arg Asp Tyr Phe Asp Tyr Trp Gly
                115                 120                 125

Gln Gly Thr Thr Leu Thr Val Ser Ser Ala Ser Thr Lys Gly Pro Ser
130                 135                 140

Val Phe Pro Leu Ala Pro Ser Ser Lys Ser Thr Ser Gly Gly Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
                180                 185                 190

Val Leu Gln Ser Ser Gly Leu Tyr Ser Leu Ser Ser Val Val Thr Val
                195                 200                 205

Pro Ser Ser Leu Gly Thr Gln Thr Tyr Ile Cys Asn Val Asn His
210                 215                 220

Lys Pro Ser Asn Thr Lys Val Asp Lys Arg Val Glu Pro Lys Ser Cys
225                 230                 235                 240

Asp Lys Thr His Thr Cys Pro Pro Cys Pro Ala Pro Glu Leu Leu Gly
                245                 250                 255

Gly Pro Ser Val Phe Leu Phe Pro Pro Lys Pro Lys Asp Thr Leu Met
                260                 265                 270

Ile Ser Arg Thr Pro Glu Val Thr Cys Val Val Val Asp Val Ser His
                275                 280                 285

Glu Asp Pro Glu Val Lys Phe Asn Trp Tyr Val Asp Gly Val Glu Val
290                 295                 300

His Asn Ala Lys Thr Lys Pro Arg Glu Glu Gln Tyr Asn Ser Thr Tyr
305                 310                 315                 320

Arg Val Val Ser Val Leu Thr Val Leu His Gln Asp Trp Leu Asn Gly
                325                 330                 335

Lys Glu Tyr Lys Cys Lys Val Ser Asn Lys Ala Leu Pro Ala Pro Ile
                340                 345                 350

Glu Lys Thr Ile Ser Lys Ala Lys Gly Gln Pro Arg Glu Pro Gln Val
                355                 360                 365

Tyr Thr Leu Pro Pro Ser Arg Glu Glu Met Thr Lys Asn Gln Val Ser
370                 375                 380

Leu Thr Cys Leu Val Lys Gly Phe Tyr Pro Ser Asp Ile Ala Val Glu
385                 390                 395                 400

Trp Glu Ser Asn Gly Gln Pro Glu Asn Asn Tyr Lys Thr Thr Pro Pro
                405                 410                 415

Val Leu Asp Ser Asp Gly Ser Phe Phe Leu Tyr Ser Lys Leu Thr Val
                420                 425                 430

Asp Lys Trp Gln Gln Gly Asn Val Phe Ser Cys Ser Val Met His Glu
                435                 440                 445

Ala Leu His Asn His Tyr Thr Gln Lys Ser Leu Ser Leu Ser Pro Gly
                450                 455                 460

Lys
465
```

```
<210> SEQ ID NO 2
<211> LENGTH: 2010
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2
atgggatgga gctgtatcat cctcttcttg gtagcaacag ctacaggtgt ccactccctc      60
gaggtccagc tgcaacagtc tggacctgag ctggtgaagc ctggggcttc actgaagatg     120
tcctgcaagg cttctggtta ttcattcact gactacatca tactctgggt gaagcagaac     180
catgaaaaga gccttgagtg gattggacat attgatcctt actatggtag ttctaactac     240
aatctgaaat tcaagggcaa ggccacattg actgtagaca atcttccag cacagcctac      300 atgcagctca acagtctgac atctgaggac tctgcagtct attactgtgg aagatctaag     360
agggactact ttgactactg gggccaaggc accactctca cagtttcctc agcctccacc     420
aagggcccat cggtcttccc cctggcaccc tcctccaaga gcacctctgg cggcacagcg     480
gccctgggct gcctggtcaa ggactacttc cccgaaccgg tgacggtgtc gtggaactca     540
ggcgccctga ccagcggcgt gcacaccttc ccggctgtcc tacagtcctc aggactctac     600
tccctcagca gcgtggtgac cgtgccctcc agcagcttgg gcacccagac ctacatctgc     660
aacgtgaatc acaagcccag caacaccaag gtggacaaga gagttggtga gaggccagca     720
caggagggga gggtgtctgc tggaagccag gctcagcgct cctgcctgga cgcatcccgg     780
ctatgcagtc ccagtccagg gcagcaaggc aggccccgtc tgcctcttca cccggaggcc     840
tctgcccgcc ccactcatgc tcaggagag gtcttctgg cttttcccc aggctctggg       900 caggcacagg ctaggtgccc ctaacccagg ccctgcacac aaaggggcag gtgctgggct     960
cagacctgcc aagagccata tccgggagga ccctgccct gacctaagcc cacccccaaag    1020 gccaaactct ccactccctc agctcggaca ccttctctcc tcccagattc cagtaactcc    1080
caatcttctc tctgcagagc ccaaatcttg tgacaaaact cacacatgcc caccgtgccc    1140
aggtaagcca gcccaggcct cgccctccag ctcaaggcgg gacaggtgcc ctagagtagc    1200
ctgcatccag ggacaggccc cagccgggtg ctgacacgtc cacctccatc tcttcctcag    1260
cacctgaact cctgggggga ccgtcagtct tcctcttccc cccaaaaccc aaggacaccc    1320
tcatgatctc ccggacccct gaggtcacat gcgtggtggt ggacgtgagc cacgaagacc    1380
ctgaggtcaa gttcaactgg tacgtggacg gcgtggaggt gcataatgcc aagacaaagc    1440
cgcgggagga gcagtacaac agcacgtacc gtgtggtcag cgtcctcacc gtcctgcacc    1500
aggactggct gaatggcaag gagtacaagt gcaaggtctc caacaaagcc ctcccagccc    1560
ccatcgagaa aaccatctcc aaagccaaag gtgggacccg tggggtgcga gggccacatg    1620
gacagaggcc ggctcggccc accctctgcc ctgagagtga ccgctgtacc aacctctgtc    1680
cctacagggc agccccgaga accacaggtg tacaccctgc ccccatcccg ggaggagatg    1740
accaagaacc aggtcagcct gacctgcctg gtcaaaggct tctatcccag cgacatcgcc    1800
gtggagtggg agagcaatgg gcagccggag aacaactaca agaccacgcc tcccgtgctg    1860
gactccgacg gctccttctt cctctatagc aagctcaccg tggacaagag caggtggcag    1920
caggggaacg tcttctcatg ctccgtgatg catgaggctc tgcacaacca ctacacgcag    1980
aagagcctct ccctgtcccc gggtaaatga                                     2010
```

<210> SEQ ID NO 3
<211> LENGTH: 2160
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (99)..(803)
<220> FEATURE:
<221> NAME/KEY: CDS
<222> LOCATION: (1195)..(1239)
<220> FEATURE:
<221> NAME/KEY: CDS
<222> LOCATION: (1358)..(1687)
<220> FEATURE:
<221> NAME/KEY: CDS
<222> LOCATION: (1785)..(2105)

<400> SEQUENCE: 3

```
gcgcgccacc agacataata gctgacagac taacagactg ttcctttcca tgggtctttt       60
ctgcagtcac cgtccttgac acgaggcgcg ccgccacc atg gga tgg agc tgt atc      116
                                          Met Gly Trp Ser Cys Ile
                                          1               5 atc ctc ttc ttg gta gca aca gct aca ggt gtc cac tcc ctc gag gtc        164
Ile Leu Phe Leu Val Ala Thr Ala Thr Gly Val His Ser Leu Glu Val
            10                  15                  20 cag ctg caa cag tct gga cct gag ctg gtg aag cct ggg gct tca ctg        212
Gln Leu Gln Gln Ser Gly Pro Glu Leu Val Lys Pro Gly Ala Ser Leu
        25                  30                  35 aag atg tcc tgc aag gct tct ggt tat tca ttc act gac tac atc ata        260
Lys Met Ser Cys Lys Ala Ser Gly Tyr Ser Phe Thr Asp Tyr Ile Ile
    40                  45                  50 ctc tgg gtg aag cag aac cat gga aag agc ctt gag tgg att gga cat        308
Leu Trp Val Lys Gln Asn His Gly Lys Ser Leu Glu Trp Ile Gly His
55                  60                  65                  70 att gat cct tac tat ggt agt tct aac tac aat ctg aaa ttc aag ggc        356
Ile Asp Pro Tyr Tyr Gly Ser Ser Asn Tyr Asn Leu Lys Phe Lys Gly
                75                  80                  85 aag gcc aca ttg act gta gac aaa tct tcc agc aca gcc tac atg cag        404
Lys Ala Thr Leu Thr Val Asp Lys Ser Ser Ser Thr Ala Tyr Met Gln
            90                  95                 100 ctc aac agt ctg aca tct gag gac tct gca gtc tat tac tgt gga aga        452
Leu Asn Ser Leu Thr Ser Glu Asp Ser Ala Val Tyr Tyr Cys Gly Arg
        105                 110                 115 tct aag agg gac tac ttt gac tac tgg ggc caa ggc acc act ctc aca        500
Ser Lys Arg Asp Tyr Phe Asp Tyr Trp Gly Gln Gly Thr Thr Leu Thr
    120                 125                 130 gtt tcc tca gcc tcc acc aag ggc cca tcg gtc ttc ccc ctg gca ccc        548
Val Ser Ser Ala Ser Thr Lys Gly Pro Ser Val Phe Pro Leu Ala Pro
135                 140                 145                 150 tcc tcc aag agc acc tct ggg ggc aca gcg gcc ctg ggc tgc ctg gtc        596
Ser Ser Lys Ser Thr Ser Gly Gly Thr Ala Ala Leu Gly Cys Leu Val
                155                 160                 165 aag gac tac ttc ccc gaa ccg gtg acg gtg tcg tgg aac tca ggc gcc        644
Lys Asp Tyr Phe Pro Glu Pro Val Thr Val Ser Trp Asn Ser Gly Ala
            170                 175                 180 ctg acc agc ggc gtg cac acc ttc ccg gct gtc cta cag tcc tca gga        692
Leu Thr Ser Gly Val His Thr Phe Pro Ala Val Leu Gln Ser Ser Gly
        185                 190                 195 ctc tac tcc ctc agc agc gtg gtg acc gtg ccc tcc agc agc ttg ggc        740
Leu Tyr Ser Leu Ser Ser Val Val Thr Val Pro Ser Ser Ser Leu Gly
    200                 205                 210
```

```
                                     -continued
acc cag acc tac atc tgc aac gtg aat cac aag ccc agc aac acc aag    788
Thr Gln Thr Tyr Ile Cys Asn Val Asn His Lys Pro Ser Asn Thr Lys
215                 220                 225                 230 gtg gac aag aga gtt ggtgagaggc cagcacaggg agggagggtg tctgctggaa    843
Val Asp Lys Arg Val
                235 gccaggctca gcgctcctgc ctggacgcat cccggctatg cagtcccagt ccagggcagc    903 aaggcaggcc ccgtctgcct cttcacccgg aggcctctgc ccgccccact catgctcagg    963 gagagggtct tctggctttt tccccaggct ctgggcaggc acaggctagg tgcccctaac    1023 ccaggccctg cacacaaagg gcaggtgct gggctcagac ctgccaagag ccatatccgg    1083 gaggaccctg cccctgacct aagcccaccc caaaggccaa actctccact ccctcagctc    1143 ggacaccttc tctcctccca gattccagta actcccaatc ttctctctgc a gag ccc    1200
                                                         Glu Pro aaa tct tgt gac aaa act cac aca tgc cca ccg tgc cca ggtaagccag    1249
Lys Ser Cys Asp Lys Thr His Thr Cys Pro Pro Cys Pro
    240                 245                 250 cccaggcctc gccctccagc tcaaggcggg acaggtgccc tagagtagcc tgcatccagg    1309
gacaggcccc agccgggtgc tgacacgtcc acctccatct cttcctca gca cct gaa    1366
                                                    Ala Pro Glu ctc ctg ggg gga ccg tca gtc ttc ctc ttc ccc cca aaa ccc aag gac    1414
Leu Leu Gly Gly Pro Ser Val Phe Leu Phe Pro Pro Lys Pro Lys Asp
            255                 260                 265 acc ctc atg atc tcc cgg acc cct gag gtc aca tgc gtg gtg gtg gac    1462
Thr Leu Met Ile Ser Arg Thr Pro Glu Val Thr Cys Val Val Val Asp
270                 275                 280                 285 gtg agc cac gaa gac cct gag gtc aag ttc aac tgg tac gtg gac ggc    1510
Val Ser His Glu Asp Pro Glu Val Lys Phe Asn Trp Tyr Val Asp Gly
                290                 295                 300 gtg gag gtg cat aat gcc aag aca aag ccg cgg gag gag cag tac aac    1558
Val Glu Val His Asn Ala Lys Thr Lys Pro Arg Glu Glu Gln Tyr Asn
            305                 310                 315 agc acg tac cgt gtg gtc agc gtc ctc acc gtc ctg cac cag gac tgg    1606
Ser Thr Tyr Arg Val Val Ser Val Leu Thr Val Leu His Gln Asp Trp
                320                 325                 330 ctg aat ggc aag gag tac aag tgc aag gtc tcc aac aaa gcc ctc cca    1654
Leu Asn Gly Lys Glu Tyr Lys Cys Lys Val Ser Asn Lys Ala Leu Pro
335                 340                 345 gcc ccc atc gag aaa acc atc tcc aaa gcc aaa ggtgggaccc gtggggtgcg    1707
Ala Pro Ile Glu Lys Thr Ile Ser Lys Ala Lys
350                 355                 360 agggccacat ggacagaggc cggctcggcc caccctctgc cctgagagtg accgctgtac    1767
caacctctgt ccctaca ggg cag ccc cga gaa cca cag gtg tac acc ctg    1817
                Gly Gln Pro Arg Glu Pro Gln Val Tyr Thr Leu
                                365                 370 ccc cca tcc cgg gag gag atg acc aag aac cag gtc agc ctg acc tgc    1865
Pro Pro Ser Arg Glu Glu Met Thr Lys Asn Gln Val Ser Leu Thr Cys
            375                 380                 385 ctg gtc aaa ggc ttc tat ccc agc gac atc gcc gtg gag tgg gag agc    1913
Leu Val Lys Gly Phe Tyr Pro Ser Asp Ile Ala Val Glu Trp Glu Ser
        390                 395                 400 aat ggg cag ccg gag aac aac tac aag acc acg cct ccc gtg ctg gac    1961
Asn Gly Gln Pro Glu Asn Asn Tyr Lys Thr Thr Pro Pro Val Leu Asp
        405                 410                 415 tcc gac ggc tcc ttc ttc ctc tat agc aag ctc acc gtg gac aag agc    2009
Ser Asp Gly Ser Phe Phe Leu Tyr Ser Lys Leu Thr Val Asp Lys Ser
420                 425                 430                 435
```

| | | | | | | | | | | | | | | | |
|---|---|---|---|---|---|---|---|---|---|---|---|---|---|---|---|
| agg | tgg | cag | cag | ggg | aac | gtc | ttc | tca | tgc | tcc | gtg | atg | cat | gag | gct | 2057 |
| Arg | Trp | Gln | Gln | Gly | Asn | Val | Phe | Ser | Cys | Ser | Val | Met | His | Glu | Ala |
| | | | 440 | | | | | 445 | | | | | 450 | | |

| | | | | | | | | | | | | | | | |
|---|---|---|---|---|---|---|---|---|---|---|---|---|---|---|---|
| ctg | cac | aac | cac | tac | acg | cag | aag | agc | ctc | tcc | ctg | tcc | ccg | ggt | aaa | 2105 |
| Leu | His | Asn | His | Tyr | Thr | Gln | Lys | Ser | Leu | Ser | Leu | Ser | Pro | Gly | Lys |
| | | 455 | | | | | 460 | | | | | 465 | | | | tgagtgcgac ggccagaatt cattgatcat aatcagccat accacatttg tagag   2160

<210> SEQ ID NO 4
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Met Gly Trp Ser Cys Ile Ile Leu Phe Leu Val Ala Thr Ala Thr Gly
1               5                   10                  15

Val His Ser Arg Asp Ile Gln Met Thr Gln Ser Pro Ser Ser Met Tyr
            20                  25                  30

Ala Ser Leu Gly Glu Arg Val Thr Ile Thr Cys Lys Ala Ser Gln Asp
        35                  40                  45

Ile Asn Ser Tyr Leu Ser Trp Phe Gln Gln Lys Pro Gly Lys Ser Pro
    50                  55                  60

Lys Thr Leu Ile Tyr Arg Ala Asn Arg Leu Val Asp Gly Val Pro Ser
65                  70                  75                  80

Arg Phe Ser Gly Ser Gly Ser Gly Gln Asp Tyr Ser Leu Thr Ile Ser
                85                  90                  95

Ser Leu Glu Tyr Glu Asp Met Gly Ile Tyr Tyr Cys Leu Gln Tyr Asp
            100                 105                 110

Glu Phe Pro Tyr Thr Phe Gly Gly Gly Thr Lys Leu Glu Ile Lys Arg
        115                 120                 125

Thr Val Ala Ala Pro Ser Val Phe Ile Phe Pro Pro Ser Asp Glu Gln
    130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 5
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 5
atgggatgga gctgtatcat cctcttcttg gtagcaacag ctacaggtgt ccactctaga   60
gacatccaga tgacacagtc tccatcttcc atgtatgcat ctctaggaga gagagtcact   120

```
atcacttgca aggcgagtca ggacattaat agctatttaa gctggttcca gcagaaacca    180
gggaaatctc ctaagaccct gatctatcgt gcaaacagat tggtagatgg ggttccatca    240
aggttcagtg gcagtggatc tgggcaagat tattctctca ccatcagcag cctggagtat    300
gaagatatgg gaatttatta ttgtctacag tatgatgagt ttccgtacac gttcggaggg    360
gggaccaagc tggaaataaa acggactgtg gctgcaccat ctgtcttcat cttcccgcca    420
tctgatgagc agttgaaatc tggaactgcc tctgttgtgt gcctgctgaa taacttctat    480
cccagagagg ccaaagtaca gtggaaggtg gataacgccc tccaatcggg taactcccag    540
gagagtgtca cagagcagga cagcaaggac agcacctaca gcctcagcag caccctgacg    600
ctgagcaaag cagactacga gaaacacaaa gtctacgcct gcgaagtcac ccatcagggc    660
ctgagctcgc ccgtcacaaa gagcttcaac aggggagagt gttaa                   705

<210> SEQ ID NO 6
<211> LENGTH: 720
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (16)..(717)

<400> SEQUENCE: 6
aagcttgccg ccacc atg gga tgg agc tgt atc atc ctc ttc ttg gta gca        51
                Met Gly Trp Ser Cys Ile Ile Leu Phe Leu Val Ala
                 1               5                   10 aca gct aca ggt gtc cac tct aga gac atc cag atg aca cag tct cca        99
Thr Ala Thr Gly Val His Ser Arg Asp Ile Gln Met Thr Gln Ser Pro
         15                  20                  25 tct tcc atg tat gca tct cta gga gag aga gtc act atc act tgc aag       147
Ser Ser Met Tyr Ala Ser Leu Gly Glu Arg Val Thr Ile Thr Cys Lys
 30                  35                  40 gcg agt cag gac att aat agc tat tta agc tgg ttc cag cag aaa cca       195
Ala Ser Gln Asp Ile Asn Ser Tyr Leu Ser Trp Phe Gln Gln Lys Pro
45                  50                  55                  60 ggg aaa tct cct aag acc ctg atc tat cgt gca aac aga ttg gta gat       243
Gly Lys Ser Pro Lys Thr Leu Ile Tyr Arg Ala Asn Arg Leu Val Asp
                 65                  70                  75 ggg gtt cca tca agg ttc agt ggc agt gga tct ggg caa gat tat tct       291
Gly Val Pro Ser Arg Phe Ser Gly Ser Gly Ser Gly Gln Asp Tyr Ser
             80                  85                  90 ctc acc atc agc agc ctg gag tat gaa gat atg gga att tat tat tgt       339
Leu Thr Ile Ser Ser Leu Glu Tyr Glu Asp Met Gly Ile Tyr Tyr Cys
         95                 100                 105 cta cag tat gat gag ttt ccg tac acg ttc gga ggg ggg acc aag ctg       387
Leu Gln Tyr Asp Glu Phe Pro Tyr Thr Phe Gly Gly Gly Thr Lys Leu
     110                 115                 120 gaa ata aaa cgg act gtg gct gca cca tct gtc ttc atc ttc ccg cca       435
Glu Ile Lys Arg Thr Val Ala Ala Pro Ser Val Phe Ile Phe Pro Pro
125                 130                 135                 140 tct gat gag cag ttg aaa tct gga act gcc tct gtt gtg tgc ctg ctg       483
Ser Asp Glu Gln Leu Lys Ser Gly Thr Ala Ser Val Val Cys Leu Leu
                145                 150                 155 aat aac ttc tat ccc aga gag gcc aaa gta cag tgg aag gtg gat aac       531
Asn Asn Phe Tyr Pro Arg Glu Ala Lys Val Gln Trp Lys Val Asp Asn
            160                 165                 170 gcc ctc caa tcg ggt aac tcc cag gag agt gtc aca gag cag gac agc       579
Ala Leu Gln Ser Gly Asn Ser Gln Glu Ser Val Thr Glu Gln Asp Ser
```

```
Ala Leu Gln Ser Gly Asn Ser Gln Glu Ser Val Thr Glu Gln Asp Ser
            175                 180                 185 aag gac agc acc tac agc ctc agc agc acc ctg acg ctg agc aaa gca      627
Lys Asp Ser Thr Tyr Ser Leu Ser Ser Thr Leu Thr Leu Ser Lys Ala
    190                 195                 200 gac tac gag aaa cac aaa gtc tac gcc tgc gaa gtc acc cat cag ggc      675
Asp Tyr Glu Lys His Lys Val Tyr Ala Cys Glu Val Thr His Gln Gly
205                 210                 215                 220 ctg agc tcg ccc gtc aca aag agc ttc aac agg gga gag tgt taa          720
Leu Ser Ser Pro Val Thr Lys Ser Phe Asn Arg Gly Glu Cys
                225                 230

<210> SEQ ID NO 7
<211> LENGTH: 463
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 7

Met Gly Trp Ser Cys Ile Ile Leu Phe Leu Val Ala Thr Ala Thr Gly
1               5                   10                  15

Val His Ser Leu Glu Val Gln Leu Gln Gln Ser Gly Pro Glu Leu Val
            20                  25                  30

Lys Pro Gly Ala Ser Leu Lys Met Ser Cys Lys Ala Ser Gly Tyr Ser
        35                  40                  45

Phe Thr Asp Tyr Ile Ile Leu Trp Val Lys Gln Asn His Gly Lys Ser
    50                  55                  60

Leu Glu Trp Ile Gly His Ile Asp Pro Tyr Tyr Gly Ser Ser Asn Tyr
65                  70                  75                  80

Asn Leu Lys Phe Lys Gly Lys Ala Thr Leu Thr Val Asp Lys Ser Ser
                85                  90                  95

Ser Thr Ala Tyr Met Gln Leu Asn Ser Leu Thr Ser Glu Asp Ser Ala
            100                 105                 110

Val Tyr Tyr Cys Gly Arg Ser Lys Arg Asp Tyr Phe Asp Tyr Trp Gly
        115                 120                 125

Gln Gly Thr Thr Leu Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
        195                 200                 205

Pro Ser Ser Asn Phe Gly Thr Gln Thr Tyr Thr Cys Asn Val Asp His
    210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser Gln Glu Asp Pro Glu
        275                 280                 285
```

```
Val Gln Phe Asn Trp Tyr Val Asp Gly Val Glu Val His Asn Ala Lys
    290                 295                 300

Thr Lys Pro Arg Glu Glu Gln Phe Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys Lys Val Ser Asn Lys Gly Leu Pro Ser Ser Ile Glu Lys Thr Ile
            340                 345                 350

Ser Lys Ala Lys Gly Gln Pro Arg Glu Pro Gln Val Tyr Thr Leu Pro
        355                 360                 365

Pro Ser Gln Glu Glu Met Thr Lys Asn Gln Val Ser Leu Thr Cys Leu
    370                 375                 380

Val Lys Gly Phe Tyr Pro Ser Asp Ile Ala Val Glu Trp Glu Ser Asn
385                 390                 395                 400

Gly Gln Pro Glu Asn Asn Tyr Lys Thr Thr Pro Pro Val Leu Asp Ser
                405                 410                 415

Asp Gly Ser Phe Phe Leu Tyr Ser Arg Leu Thr Val Asp Lys Ser Arg
            420                 425                 430

Trp Gln Glu Gly Asn Val Phe Ser Cys Ser Val Met His Glu Ala Leu
        435                 440                 445

His Asn His Tyr Thr Gln Lys Ser Leu Ser Leu Ser Leu Gly Lys
    450                 455                 460

<210> SEQ ID NO 8
<211> LENGTH: 1999
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 8
atgggatgga gctgtatcat cctcttcttg gtagcaacag ctacaggtgt ccactccctc     60
gaggtccagc tgcaacagtc tggacctgag ctggtgaagc ctggggcttc actgaagatg    120
tcctgcaagg cttctggtta ttcattcact gactacatca tactctgggt gaagcagaac    180
catggaaaga gccttgagtg gattggacat attgatcctt actatggtag ttctaactac    240
aatctgaaat tcaagggcaa ggccacattg actgtagaca atcttccagc acagcctac    300 atgcagctca cagtctgac atctgaggac tctgcagtct attactgtgg aagatctaag    360
agggactact tgactactg gggccaaggc accactctca cagtttcctc agcctccacc    420
aagggcccat ccgtcttccc cctggcgccc tgctccagga gcacctccga gcacagcc    480 gccctgggct gcctggtcaa ggactacttc cccgaaccgg tgacggtgtc gtggaactca    540
ggcgccctga ccagcggcgt gcacaccttc ccggctgtcc tacagtcctc aggactctac    600
tccctcagca gcgtggtgac cgtgccctcc agcaacttcg gcacccagac ctacacctgc    660
aacgtagatc acaagcccag caacaccaag gtggacaaga cagttggtga gaggccagct    720
cagggaggga gggtgtctgc tggaagccag gctcagccct cctgcctgga cgcacccgg    780 ctgtgcagcc ccagcccagg gcagcaaggc aggccccatc tgtctcctca cccggaggcc    840 tctgccccgcc ccactcatgc tcagggagag ggtcttctgg cttttttccac caggctccag    900 gcaggcacag gctgggtgcc cctaccccag gcccttcaca cacaggggca ggtgcttggc    960
tcagacctgc caaaagccat atccgggagg accctgcccc tgacctaagc cgaccccaaa   1020
ggccaaactg tccactcccct cagctcggac accttctctc ctcccagatc cgagtaactc   1080
```

```
ccaatcttct ctctgcagag cgcaaatgtt gtgtcgagtg cccaccgtgc ccaggtaagc    1140
cagcccaggc ctcgccctcc agctcaaggc gggacaggtg ccctagagta gcctgcatcc    1200
agggacaggc cccagctggg tgctgacacg tccacctcca tctcttcctc agcaccacct    1260
gtggcaggac cgtcagtctt cctcttcccc ccaaaaccca aggacaccct catgatctcc    1320
cggacccctg aggtcacgtg cgtggtggtg gacgtgagcc aggaagaccc cgaggtccag    1380
ttcaactggt acgtggatgg cgtggaggtg cataatgcca agacaaagcc gcgggaggag    1440
cagttcaaca gcacgtaccg tgtggtcagc gtcctcaccg tcctgcacca ggactggctg    1500
aacggcaagg agtacaagtg caaggtctcc aacaaaggcc tcccgtcctc catcgagaaa    1560
accatctcca aagccaaagg tgggacccac ggggtgcgag ggccacatgg acagaggtca    1620
gctcggccca ccctctgccc tgggagtgac cgctgtgcca acctctgtcc ctacagggca    1680
gccccgagag ccacaggtgt acaccctgcc ccatcccag gaggagatga ccaagaacca    1740
ggtcagcctg acctgcctgg tcaaaggctt ctaccccagc gacatcgccg tggagtggga    1800
gagcaatggg cagccggaga caactacaa gaccacgcct cccgtgctgg actccgacgg    1860
ctccttcttc ctctacagca ggctaaccgt ggacaagagc aggtggcagg aggggaatgt    1920
cttctcatgc tccgtgatgc atgaggctct gcacaaccac tacacacaga gagcctctc    1980 cctgtctctg ggtaaatga                                                1999
```

<210> SEQ ID NO 9
<211> LENGTH: 337
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 9

```
Met Gly Trp Ser Cys Ile Ile Leu Phe Leu Val Ala Thr Ala Thr Gly
1               5                   10                  15

Val His Ser Leu Glu Val Gln Leu Gln Gln Ser Gly Pro Glu Leu Val
            20                  25                  30

Lys Pro Gly Ala Ser Leu Lys Met Ser Cys Lys Ala Ser Gly Tyr Ser
        35                  40                  45

Phe Thr Asp Tyr Ile Ile Leu Trp Val Lys Gln Asn His Gly Lys Ser
    50                  55                  60

Leu Glu Trp Ile Gly His Ile Asp Pro Tyr Tyr Gly Ser Ser Asn Tyr
65                  70                  75                  80

Asn Leu Lys Phe Lys Gly Lys Ala Thr Leu Thr Val Asp Lys Ser Ser
                85                  90                  95

Ser Thr Ala Tyr Met Gln Leu Asn Ser Leu Thr Ser Glu Asp Ser Ala
            100                 105                 110

Val Tyr Tyr Cys Gly Arg Ser Lys Arg Asp Tyr Phe Asp Tyr Trp Gly
        115                 120                 125

Gln Gly Thr Thr Leu Thr Val Ser Ser Ala Ser Thr Lys Gly Pro Ser
    130                 135                 140

Val Phe Pro Leu Ala Pro Cys Ser Arg Ser Thr Ser Glu Ser Thr Ala
145                 150                 155                 160

Ala Leu Gly Cys Leu Val Lys Asp Tyr Phe Pro Glu Pro Val Thr Val
                165                 170                 175

Ser Trp Asn Ser Gly Ala Leu Thr Ser Gly Val His Thr Phe Pro Ala
            180                 185                 190

Val Leu Gln Ser Ser Gly Leu Tyr Ser Leu Ser Ser Val Val Thr Val
```

```
                 195                 200                 205
Pro Ser Ser Asn Phe Gly Thr Gln Thr Tyr Thr Cys Asn Val Asp His
210                 215                 220

Lys Pro Ser Asn Thr Lys Val Asp Lys Thr Val Glu Arg Lys Cys Cys
225                 230                 235                 240

Val Glu Cys Pro Pro Cys Pro Ala Pro Pro Val Ala Gly Pro Ser Val
                245                 250                 255

Phe Leu Phe Pro Pro Lys Pro Lys Asp Thr Leu Met Ile Ser Arg Thr
            260                 265                 270

Pro Glu Val Thr Cys Val Val Val Asp Val Ser Gln Glu Asp Pro Glu
        275                 280                 285

Val Gln Phe Asn Trp Tyr Val Asp Gly Val Glu Val His Asn Ala Lys
    290                 295                 300

Thr Lys Pro Arg Glu Glu Gln Phe Asn Ser Thr Tyr Arg Val Val Ser
305                 310                 315                 320

Val Leu Thr Val Leu His Gln Asp Trp Leu Asn Gly Lys Glu Tyr Lys
                325                 330                 335

Cys

<210> SEQ ID NO 10
<211> LENGTH: 1600
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (79)..(783)
<220> FEATURE:
<221> NAME/KEY: CDS
<222> LOCATION: (1176)..(1211)

<400> SEQUENCE: 10
gctgacagac taacagactg ttcctttcca tgggtctttt ctgcagtcac cgtccttgac        60
acgaggcgcg ccgccacc atg gga tgg agc tgt atc atc ctc ttc ttg gta       111
                    Met Gly Trp Ser Cys Ile Ile Leu Phe Leu Val
                    1               5                   10 gca aca gct aca ggt gtc cac tcc ctc gag gtc cag ctg caa cag tct       159
Ala Thr Ala Thr Gly Val His Ser Leu Glu Val Gln Leu Gln Gln Ser
                15                  20                  25 gga cct gag ctg gtg aag cct ggg gct tca ctg aag atg tcc tgc aag       207
Gly Pro Glu Leu Val Lys Pro Gly Ala Ser Leu Lys Met Ser Cys Lys
        30                  35                  40 gct tct ggt tat tca ttc act gac tac atc ata ctc tgg gtg aag cag       255
Ala Ser Gly Tyr Ser Phe Thr Asp Tyr Ile Ile Leu Trp Val Lys Gln
    45                  50                  55 aac cat gga aag agc ctt gag tgg att gga cat att gat cct tac tat       303
Asn His Gly Lys Ser Leu Glu Trp Ile Gly His Ile Asp Pro Tyr Tyr
60                  65                  70                  75 ggt agt tct aac tac aat ctg aaa ttc aag ggc aag gcc aca ttg act       351
Gly Ser Ser Asn Tyr Asn Leu Lys Phe Lys Gly Lys Ala Thr Leu Thr
                80                  85                  90 gta gac aaa tct tcc agc aca gcc tac atg cag ctc aac agt ctg aca       399
Val Asp Lys Ser Ser Ser Thr Ala Tyr Met Gln Leu Asn Ser Leu Thr
            95                  100                 105 tct gag gac tct gca gtc tat tac tgt gga aga tct aag agg gac tac       447
Ser Glu Asp Ser Ala Val Tyr Tyr Cys Gly Arg Ser Lys Arg Asp Tyr
        110                 115                 120 ttt gac tac tgg ggc caa ggc acc act ctc aca gtt tcc tca gcc tcc       495
```

```
                Phe Asp Tyr Trp Gly Gln Gly Thr Thr Leu Thr Val Ser Ser Ala Ser
                    125                 130                 135 acc aag ggc cca tcc gtc ttc ccc ctg gcg ccc tgc tcc agg agc acc            543
Thr Lys Gly Pro Ser Val Phe Pro Leu Ala Pro Cys Ser Arg Ser Thr
140                 145                 150                 155 tcc gag agc aca gcc gcc ctg ggc tgc ctg gtc aag gac tac ttc ccc            591
Ser Glu Ser Thr Ala Ala Leu Gly Cys Leu Val Lys Asp Tyr Phe Pro
                160                 165                 170 gaa ccg gtg acg gtg tcg tgg aac tca ggc gcc ctg acc agc ggc gtg            639
Glu Pro Val Thr Val Ser Trp Asn Ser Gly Ala Leu Thr Ser Gly Val
            175                 180                 185 cac acc ttc ccg gct gtc cta cag tcc tca gga ctc tac tcc ctc agc            687
His Thr Phe Pro Ala Val Leu Gln Ser Ser Gly Leu Tyr Ser Leu Ser
        190                 195                 200 agc gtg gtg acc gtg ccc tcc agc aac ttc ggc acc cag acc tac acc            735
Ser Val Val Thr Val Pro Ser Ser Asn Phe Gly Thr Gln Thr Tyr Thr
    205                 210                 215 tgc aac gta gat cac aag ccc agc aac acc aag gtg gac aag aca gtt            783
Cys Asn Val Asp His Lys Pro Ser Asn Thr Lys Val Asp Lys Thr Val
220                 225                 230                 235 ggtgagaggc cagctcaggg agggaggggtg tctgctggaa gccaggctca gccctcctgc         843
ctggacgcac cccggctgtg cagccccagc ccagggcagc aaggcaggcc ccatctgtct          903
cctcacccgg aggcctctgc ccgccccact catgctcagg gagagggtct tctggctttt          963
tccaccaggc tccaggcagg cacaggctgg gtgcccctac cccaggccct tcacacacag         1023
gggcaggtgc ttggctcaga cctgccaaaa gccatatccg ggaggaccct gccctgacc         1083 taagccgacc ccaaaggcca aactgtccac tccctcagct cggacacctt ctctcctccc        1143
agatccgagt aactcccaat cttctctctg ca gag cgc aaa tgt tgt gtc gag          1196
                                     Glu Arg Lys Cys Cys Val Glu
                                                     240 tgc cca ccg tgc cca ggtaagccag cccaggcctc gccctccagc tcaaggcggg          1251
Cys Pro Pro Cys Pro
        245 acaggtgccc tagagtagcc tgcatccagg gacaggcccc agctgggtgc tgacacgtcc        1311 acctccatct cttcctcagc accacctgtg gcaggaccgt cagtcttcct cttccccca         1371 aaacccaagg acaccctcat gatctcccgg acccctgagg tcacgtgcgt ggtggtggac       1431 gtgagccagg aagaccccga ggtccagttc aactggtacg tggatggcgt ggaggtgcat       1491 aatgccaaga caaagccgcg ggaggagcag ttcaacagca cgtaccgtgt ggtcagcgtc       1551 ctcaccgtcc tgcaccagga ctggctgaac ggcaaggagt acaagtgca                   1600

<210> SEQ ID NO 11
<211> LENGTH: 234
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 11

Met Gly Trp Ser Cys Ile Ile Leu Phe Leu Val Ala Thr Ala Thr Gly
1               5                   10                  15

Val His Ser Arg Asp Ile Gln Met Thr Gln Ser Pro Ser Ser Met Tyr
            20                  25                  30

Ala Ser Leu Gly Glu Arg Val Thr Ile Thr Cys Lys Ala Ser Gln Asp
        35                  40                  45

Ile Asn Ser Tyr Leu Ser Trp Phe Gln Gln Lys Pro Gly Lys Ser Pro
```

```
                50              55                  60
Lys Thr Leu Ile Tyr Arg Ala Asn Arg Leu Val Asp Gly Val Pro Ser
 65                  70                  75                  80

Arg Phe Ser Gly Ser Gly Ser Gly Gln Asp Tyr Ser Leu Thr Ile Ser
                 85                  90                  95

Ser Leu Glu Tyr Glu Asp Met Gly Ile Tyr Tyr Cys Leu Gln Tyr Asp
             100                 105                 110

Glu Phe Pro Tyr Thr Phe Gly Gly Thr Lys Leu Glu Ile Lys Arg
         115                 120                 125

Thr Val Ala Ala Pro Ser Val Phe Ile Phe Pro Pro Ser Asp Glu Gln
130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys
225                 230

<210> SEQ ID NO 12
<211> LENGTH: 705
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 12
atgggatgga gctgtatcat cctcttcttg gtagcaacag ctacaggtgt ccactctaga    60
gacatccaga tgacacagtc tccatcttcc atgtatgcat ctctaggaga gagagtcact   120
atcacttgca aggcgagtca ggacattaat agctatttaa gctggttcca gcagaaacca   180
gggaaatctc ctaagaccct gatctatcgt gcaaacagat ggtagatgg ggttccatca   240 aggttcagtg gcagtggatc tgggcaagat tattctctca ccatcagcag cctggagtat   300
gaagatatgg gaatttatta ttgtctacag tatgatgagt ttccgtacac gttcggaggg   360
gggaccaagc tggaaataaa acggactgtg gctgcaccat ctgtcttcat cttcccgcca   420
tctgatgagc agttgaaatc tggaactgcc tctgttgtgt gcctgctgaa taacttctat   480
cccagagagg ccaaagtaca gtggaaggtg gataacgccc tccaatcggg taactcccag   540
gagagtgtca cagagcagga cagcaaggac agcacctaca gcctcagcag caccctgacg   600
ctgagcaaag cagactacga gaaacacaaa gtctacgcct gcgaagtcac ccatcagggc   660
ctgagctcgc ccgtcacaaa gagcttcaac aggggagagt gttaa                   705

<210> SEQ ID NO 13
<211> LENGTH: 240
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13
```

```
Met Gly Trp Ser Cys Ile Ile Leu Phe Leu Val Ala Thr Ala Thr Gly
 1               5                  10                  15

Val His Ser Arg Asp Ile Gln Met Thr Gln Ser Pro Ser Ser Met Tyr
             20                  25                  30

Ala Ser Leu Gly Glu Arg Val Thr Ile Thr Cys Lys Ala Ser Gln Asp
         35                  40                  45

Ile Asn Ser Tyr Leu Ser Trp Phe Gln Gln Lys Pro Gly Lys Ser Pro
 50                  55                  60

Lys Thr Leu Ile Tyr Arg Ala Asn Arg Leu Val Asp Gly Val Pro Ser
 65                  70                  75                  80

Arg Phe Ser Gly Ser Gly Ser Gly Gln Asp Tyr Ser Leu Thr Ile Ser
                 85                  90                  95

Ser Leu Glu Tyr Glu Asp Met Gly Ile Tyr Tyr Cys Leu Gln Tyr Asp
            100                 105                 110

Glu Phe Pro Tyr Thr Phe Gly Gly Thr Lys Leu Glu Ile Lys Arg
            115                 120                 125

Thr Val Ala Ala Pro Ser Val Phe Ile Phe Pro Pro Ser Asp Glu Gln
        130                 135                 140

Leu Lys Ser Gly Thr Ala Ser Val Val Cys Leu Leu Asn Asn Phe Tyr
145                 150                 155                 160

Pro Arg Glu Ala Lys Val Gln Trp Lys Val Asp Asn Ala Leu Gln Ser
                165                 170                 175

Gly Asn Ser Gln Glu Ser Val Thr Glu Gln Asp Ser Lys Asp Ser Thr
            180                 185                 190

Tyr Ser Leu Ser Ser Thr Leu Thr Leu Ser Lys Ala Asp Tyr Glu Lys
        195                 200                 205

His Lys Val Tyr Ala Cys Glu Val Thr His Gln Gly Leu Ser Ser Pro
    210                 215                 220

Val Thr Lys Ser Phe Asn Arg Gly Glu Cys Ser Ala Ala Ala Ile His
225                 230                 235                 240
```

<210> SEQ ID NO 14
<211> LENGTH: 738
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (16)..(735)

<400> SEQUENCE: 14

```
aagcttgccg ccacc atg gga tgg agc tgt atc atc ctc ttc ttg gta gca        51
                Met Gly Trp Ser Cys Ile Ile Leu Phe Leu Val Ala
                 1               5                  10 aca gct aca ggt gtc cac tct aga gac atc cag atg aca cag tct cca        99
Thr Ala Thr Gly Val His Ser Arg Asp Ile Gln Met Thr Gln Ser Pro
             15                  20                  25 tct tcc atg tat gca tct cta gga gag aga gtc act atc act tgc aag       147
Ser Ser Met Tyr Ala Ser Leu Gly Glu Arg Val Thr Ile Thr Cys Lys
         30                  35                  40 gcg agt cag gac att aat agc tat tta agc tgg ttc cag cag aaa cca       195
Ala Ser Gln Asp Ile Asn Ser Tyr Leu Ser Trp Phe Gln Gln Lys Pro
 45                  50                  55                  60 ggg aaa tct cct aag acc ctg atc tat cgt gca aac aga ttg gta gat       243
Gly Lys Ser Pro Lys Thr Leu Ile Tyr Arg Ala Asn Arg Leu Val Asp
                 65                  70                  75
```

```
ggg gtt cca tca agg ttc agt ggc agt gga tct ggg caa gat tat tct      291
Gly Val Pro Ser Arg Phe Ser Gly Ser Gly Ser Gly Gln Asp Tyr Ser
        80                  85                  90 ctc acc atc agc agc ctg gag tat gaa gat atg gga att tat tat tgt      339
Leu Thr Ile Ser Ser Leu Glu Tyr Glu Asp Met Gly Ile Tyr Tyr Cys
        95                 100                 105 cta cag tat gat gag ttt ccg tac acg ttc gga ggg ggg acc aag ctg      387
Leu Gln Tyr Asp Glu Phe Pro Tyr Thr Phe Gly Gly Gly Thr Lys Leu
       110                 115                 120 gaa ata aaa cgg act gtg gct gca cca tct gtc ttc atc ttc ccg cca      435
Glu Ile Lys Arg Thr Val Ala Ala Pro Ser Val Phe Ile Phe Pro Pro
125                 130                 135                 140 tct gat gag cag ttg aaa tct gga act gcc tct gtt gtg tgc ctg ctg      483
Ser Asp Glu Gln Leu Lys Ser Gly Thr Ala Ser Val Val Cys Leu Leu
                145                 150                 155 aat aac ttc tat ccc aga gag gcc aaa gta cag tgg aag gtg gat aac      531
Asn Asn Phe Tyr Pro Arg Glu Ala Lys Val Gln Trp Lys Val Asp Asn
                160                 165                 170 gcc ctc caa tcg ggt aac tcc cag gag agt gtc aca gag cag gac agc      579
Ala Leu Gln Ser Gly Asn Ser Gln Glu Ser Val Thr Glu Gln Asp Ser
        175                 180                 185 aag gac agc acc tac agc ctc agc agc acc ctg acg ctg agc aaa gca      627
Lys Asp Ser Thr Tyr Ser Leu Ser Ser Thr Leu Thr Leu Ser Lys Ala
        190                 195                 200 gac tac gag aaa cac aaa gtc tac gcc tgc gaa gtc acc cat cag ggc      675
Asp Tyr Glu Lys His Lys Val Tyr Ala Cys Glu Val Thr His Gln Gly
205                 210                 215                 220 ctg agc tcg ccc gtc aca aag agc ttc aac agg gga gag tgt tca gcg      723
Leu Ser Ser Pro Val Thr Lys Ser Phe Asn Arg Gly Glu Cys Ser Ala
                225                 230                 235 gcc gca att cat tga                                                  738
Ala Ala Ile His
        240

<210> SEQ ID NO 15
<211> LENGTH: 466
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 15

Met Gly Trp Ser Arg Ile Phe Leu Phe Leu Leu Ser Ile Ile Ala Gly
1               5                  10                  15

Val His Cys Gln Val Gln Leu Gln Gln Ser Gly Ser Glu Leu Lys Lys
            20                  25                  30

Pro Gly Ala Ser Val Lys Ile Ser Cys Lys Ala Ser Gly Tyr Ser Phe
        35                  40                  45

Thr Asp Tyr Ile Ile Leu Trp Val Arg Gln Asn Pro Gly Lys Gly Leu
    50                  55                  60

Glu Trp Ile Gly His Ile Asp Pro Tyr Gly Ser Ser Asn Tyr Asn
65                  70                  75                  80

Leu Lys Phe Lys Gly Arg Val Thr Ile Thr Ala Asp Gln Ser Thr Thr
                85                  90                  95

Thr Ala Tyr Met Glu Leu Ser Ser Leu Arg Ser Glu Asp Thr Ala Val
            100                 105                 110

Tyr Tyr Cys Gly Arg Ser Lys Arg Asp Tyr Phe Asp Tyr Trp Gly Gln
        115                 120                 125

Gly Thr Thr Leu Thr Val Ser Ser Ala Ser Thr Lys Gly Pro Ser Val
```

|     |     |     |     |     |     |     |     |     |     |     |     |
|-----|-----|-----|-----|-----|-----|-----|-----|-----|-----|-----|-----|
|     |     | 130 |     |     |     | 135 |     |     |     | 140 |     |
| Phe | Pro | Leu | Ala | Pro | Ser | Ser | Lys | Ser | Thr | Ser | Gly | Gly | Thr | Ala | Ala |
| 145 |     |     |     | 150 |     |     |     |     | 155 |     |     |     |     | 160 |     |
| Leu | Gly | Cys | Leu | Val | Lys | Asp | Tyr | Phe | Pro | Glu | Pro | Val | Thr | Val | Ser |
|     |     |     |     | 165 |     |     |     |     | 170 |     |     |     |     | 175 |     |
| Trp | Asn | Ser | Gly | Ala | Leu | Thr | Ser | Gly | Val | His | Thr | Phe | Pro | Ala | Val |
|     |     |     | 180 |     |     |     |     | 185 |     |     |     |     | 190 |     |     |
| Leu | Gln | Ser | Ser | Gly | Leu | Tyr | Ser | Leu | Ser | Ser | Val | Val | Thr | Val | Pro |
|     |     | 195 |     |     |     |     | 200 |     |     |     |     | 205 |     |     |     |
| Ser | Ser | Ser | Leu | Gly | Thr | Gln | Thr | Tyr | Ile | Cys | Asn | Val | Asn | His | Lys |
| 210 |     |     |     |     |     | 215 |     |     |     |     | 220 |     |     |     |     |
| Pro | Ser | Asn | Thr | Lys | Val | Asp | Lys | Arg | Val | Glu | Pro | Lys | Ser | Cys | Asp |
| 225 |     |     |     | 230 |     |     |     |     | 235 |     |     |     |     | 240 |     |
| Lys | Thr | His | Thr | Cys | Pro | Pro | Cys | Pro | Ala | Pro | Glu | Leu | Leu | Gly | Gly |
|     |     |     |     | 245 |     |     |     |     | 250 |     |     |     |     | 255 |     |
| Pro | Ser | Val | Phe | Leu | Phe | Pro | Pro | Lys | Pro | Lys | Asp | Thr | Leu | Met | Ile |
|     |     |     | 260 |     |     |     |     | 265 |     |     |     |     | 270 |     |     |
| Ser | Arg | Thr | Pro | Glu | Val | Thr | Cys | Val | Val | Val | Asp | Val | Ser | His | Glu |
|     |     | 275 |     |     |     |     | 280 |     |     |     |     | 285 |     |     |     |
| Asp | Pro | Glu | Val | Lys | Phe | Asn | Trp | Tyr | Val | Asp | Gly | Val | Glu | Val | His |
| 290 |     |     |     |     |     | 295 |     |     |     |     | 300 |     |     |     |     |
| Asn | Ala | Lys | Thr | Lys | Pro | Arg | Glu | Glu | Gln | Tyr | Asn | Ser | Thr | Tyr | Arg |
| 305 |     |     |     | 310 |     |     |     |     | 315 |     |     |     |     | 320 |     |
| Val | Val | Ser | Val | Leu | Thr | Val | Leu | His | Gln | Asp | Trp | Leu | Asn | Gly | Lys |
|     |     |     |     | 325 |     |     |     |     | 330 |     |     |     |     | 335 |     |
| Glu | Tyr | Lys | Cys | Lys | Val | Ser | Asn | Lys | Ala | Leu | Pro | Ala | Pro | Ile | Glu |
|     |     |     | 340 |     |     |     |     | 345 |     |     |     |     | 350 |     |     |
| Lys | Thr | Ile | Ser | Lys | Ala | Lys | Gly | Gln | Pro | Arg | Glu | Pro | Gln | Val | Tyr |
|     |     | 355 |     |     |     |     | 360 |     |     |     |     | 365 |     |     |     |
| Thr | Leu | Pro | Pro | Ser | Arg | Glu | Glu | Met | Thr | Lys | Asn | Gln | Val | Ser | Leu |
| 370 |     |     |     |     |     | 375 |     |     |     |     | 380 |     |     |     |     |
| Thr | Cys | Leu | Val | Lys | Gly | Phe | Tyr | Pro | Ser | Asp | Ile | Ala | Val | Glu | Trp |
| 385 |     |     |     | 390 |     |     |     |     | 395 |     |     |     |     | 400 |     |
| Glu | Ser | Asn | Gly | Gln | Pro | Glu | Asn | Asn | Tyr | Lys | Thr | Thr | Pro | Pro | Val |
|     |     |     |     | 405 |     |     |     |     | 410 |     |     |     |     | 415 |     |
| Leu | Asp | Ser | Asp | Gly | Ser | Phe | Phe | Leu | Tyr | Ser | Lys | Leu | Thr | Val | Asp |
|     |     |     | 420 |     |     |     |     | 425 |     |     |     |     | 430 |     |     |
| Lys | Ser | Arg | Trp | Gln | Gln | Gly | Asn | Val | Phe | Ser | Cys | Ser | Val | Met | His |
|     |     | 435 |     |     |     |     | 440 |     |     |     |     | 445 |     |     |     |
| Glu | Ala | Leu | His | Asn | His | Tyr | Thr | Gln | Lys | Ser | Leu | Ser | Leu | Ser | Pro |
| 450 |     |     |     |     |     | 455 |     |     |     |     | 460 |     |     |     |     |
| Gly | Lys |
| 465 |     |

```
<210> SEQ ID NO 16
<211> LENGTH: 1401
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 16
atgggatgga gccggatctt tctcttcctc ctgtcaataa ttgcaggtgt ccattgccag      60
gtccagctgc aacagtctgg atctgagctg aagaagcctg gggcttcagt gaagatctcc     120
```

```
tgcaaggctt ctggttattc attcactgac tacatcatac tctgggtgag cagaaccct    180
ggaaagggcc ttgagtggat tggacatatt gatccttact atggtagttc taactacaat    240
ctgaaattca agggcagagt gacaatcacc gccgaccagt ctaccaccac agcctacatg    300
gagctctcca gtctgagatc tgaggacact gcagtctatt actgtggaag atctaagagg    360
gactactttg actactgggg ccaaggcacc actctcacag tttcctcagc ctccaccaag    420
ggcccatcgg tcttcccgct agcaccctcc tccaagagca cctctggggg cacagcggcc    480
ctgggctgcc tggtcaagga ctacttcccc gaaccggtga cggtgtcgtg aactcaggc    540
gccctgacca gcggcgtgca caccttcccg gctgtcctac agtcctcagg actctactcc    600
ctcagcagcg tggtgaccgt gccctccagc agcttgggca cccagaccta catctgcaac    660
gtgaatcaca agcccagcaa caccaaggtg gacaagagag ttgagcccaa atcttgtgac    720
aaaactcaca catgcccacc gtgcccagca cctgaactcc tggggggacc gtcagtcttc    780
ctcttccccc caaaacccaa ggacaccctc atgatctccc ggaccctga ggtcacatgc    840
gtggtggtgg acgtgagcca cgaagaccct gaggtcaagt tcaactggta cgtggacggc    900
gtggaggtgc ataatgccaa gacaaagccg cgggaggagc agtacaacag cacgtaccgt    960
gtggtcagcg tcctcaccgt cctgcaccag gactggctga atggcaagga gtacaagtgc   1020
aaggtctcca acaaagccct cccagccccc atcgagaaaa ccatctccaa agccaaaggg   1080
cagccccgag aaccacaggt gtacaccctg cccccatccc gggaggagat gaccaagaac   1140
caggtcagcc tgacctgcct ggtcaaaggc ttctatccca gcgacatcgc cgtggagtgg   1200
gagagcaatg ggcagccgga gaacaactac aagaccacgc tcccgtgct ggactccgac    1260
ggctccttct cctctacag caagctcacc gtggacaaga gcaggtggca gcaggggaac   1320
gtcttctcat gctccgtgat gcatgaggct ctgcacaacc actacacgca gaagagcctc   1380
tccctgtctc cgggtaaatg a                                              1401
```

<210> SEQ ID NO 17
<211> LENGTH: 1402
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (2)..(1399)

<400> SEQUENCE: 17

```
c atg gga tgg agc cgg atc ttt ctc ttc ctc ctg tca ata att gca ggt    49
  Met Gly Trp Ser Arg Ile Phe Leu Phe Leu Leu Ser Ile Ile Ala Gly
  1               5                   10                  15 gtc cat tgc cag gtc cag ctg caa cag tct gga tct gag ctg aag aag    97
Val His Cys Gln Val Gln Leu Gln Gln Ser Gly Ser Glu Leu Lys Lys
            20                  25                  30 cct ggg gct tca gtg aag atc tcc tgc aag gct tct ggt tat tca ttc   145
Pro Gly Ala Ser Val Lys Ile Ser Cys Lys Ala Ser Gly Tyr Ser Phe
        35                  40                  45 act gac tac atc ata ctc tgg gtg agg cag aac cct gga aag ggc ctt   193
Thr Asp Tyr Ile Ile Leu Trp Val Arg Gln Asn Pro Gly Lys Gly Leu
    50                  55                  60 gag tgg att gga cat att gat cct tac tat ggt agt tct aac tac aat   241
Glu Trp Ile Gly His Ile Asp Pro Tyr Tyr Gly Ser Ser Asn Tyr Asn
65                  70                  75                  80 ctg aaa ttc aag ggc aga gtg aca atc acc gcc gac cag tct acc acc   289
Leu Lys Phe Lys Gly Arg Val Thr Ile Thr Ala Asp Gln Ser Thr Thr
```

|     |     |     |     |     |     |     |     |     |     |     |     |     |     |     |     |      |
| --- | --- | --- | --- | --- | --- | --- | --- | --- | --- | --- | --- | --- | --- | --- | --- | ---- |
|     |     |     | 85  |     |     |     | 90  |     |     |     | 95  |     |     |     |     |      |
| aca | gcc | tac | atg | gag | ctc | tcc | agt | ctg | aga | tct | gag | gac | act | gca | gtc | 337  |
| Thr | Ala | Tyr | Met | Glu | Leu | Ser | Ser | Leu | Arg | Ser | Glu | Asp | Thr | Ala | Val |      |
|     |     |     | 100 |     |     |     |     | 105 |     |     |     | 110 |     |     |     |      |
| tat | tac | tgt | gga | aga | tct | aag | agg | gac | tac | ttt | gac | tac | tgg | ggc | caa | 385  |
| Tyr | Tyr | Cys | Gly | Arg | Ser | Lys | Arg | Asp | Tyr | Phe | Asp | Tyr | Trp | Gly | Gln |      |
|     |     | 115 |     |     |     |     | 120 |     |     |     |     | 125 |     |     |     |      |
| ggc | acc | act | ctc | aca | gtt | tcc | tca | gcc | tcc | acc | aag | ggc | cca | tcg | gtc | 433  |
| Gly | Thr | Thr | Leu | Thr | Val | Ser | Ser | Ala | Ser | Thr | Lys | Gly | Pro | Ser | Val |      |
|     | 130 |     |     |     |     | 135 |     |     |     |     | 140 |     |     |     |     |      |
| ttc | ccg | cta | gca | ccc | tcc | tcc | aag | agc | acc | tct | ggg | ggc | aca | gcg | gcc | 481  |
| Phe | Pro | Leu | Ala | Pro | Ser | Ser | Lys | Ser | Thr | Ser | Gly | Gly | Thr | Ala | Ala |      |
| 145 |     |     |     |     | 150 |     |     |     |     | 155 |     |     |     |     | 160 |      |
| ctg | ggc | tgc | ctg | gtc | aag | gac | tac | ttc | ccc | gaa | ccg | gtg | acg | gtg | tcg | 529  |
| Leu | Gly | Cys | Leu | Val | Lys | Asp | Tyr | Phe | Pro | Glu | Pro | Val | Thr | Val | Ser |      |
|     |     |     |     | 165 |     |     |     |     | 170 |     |     |     |     | 175 |     |      |
| tgg | aac | tca | ggc | gcc | ctg | acc | agc | ggc | gtg | cac | acc | ttc | ccg | gct | gtc | 577  |
| Trp | Asn | Ser | Gly | Ala | Leu | Thr | Ser | Gly | Val | His | Thr | Phe | Pro | Ala | Val |      |
|     |     |     | 180 |     |     |     |     | 185 |     |     |     |     | 190 |     |     |      |
| cta | cag | tcc | tca | gga | ctc | tac | tcc | ctc | agc | agc | gtg | gtg | acc | gtg | ccc | 625  |
| Leu | Gln | Ser | Ser | Gly | Leu | Tyr | Ser | Leu | Ser | Ser | Val | Val | Thr | Val | Pro |      |
|     |     | 195 |     |     |     |     | 200 |     |     |     |     | 205 |     |     |     |      |
| tcc | agc | agc | ttg | ggc | acc | cag | acc | tac | atc | tgc | aac | gtg | aat | cac | aag | 673  |
| Ser | Ser | Ser | Leu | Gly | Thr | Gln | Thr | Tyr | Ile | Cys | Asn | Val | Asn | His | Lys |      |
|     | 210 |     |     |     |     | 215 |     |     |     |     | 220 |     |     |     |     |      |
| ccc | agc | aac | acc | aag | gtg | gac | aag | aga | gtt | gag | ccc | aaa | tct | tgt | gac | 721  |
| Pro | Ser | Asn | Thr | Lys | Val | Asp | Lys | Arg | Val | Glu | Pro | Lys | Ser | Cys | Asp |      |
| 225 |     |     |     |     | 230 |     |     |     |     | 235 |     |     |     |     | 240 |      |
| aaa | act | cac | aca | tgc | cca | ccg | tgc | cca | gca | cct | gaa | ctc | ctg | ggg | gga | 769  |
| Lys | Thr | His | Thr | Cys | Pro | Pro | Cys | Pro | Ala | Pro | Glu | Leu | Leu | Gly | Gly |      |
|     |     |     |     | 245 |     |     |     |     | 250 |     |     |     |     | 255 |     |      |
| ccg | tca | gtc | ttc | ctc | ttc | ccc | cca | aaa | ccc | aag | gac | acc | ctc | atg | atc | 817  |
| Pro | Ser | Val | Phe | Leu | Phe | Pro | Pro | Lys | Pro | Lys | Asp | Thr | Leu | Met | Ile |      |
|     |     |     | 260 |     |     |     |     | 265 |     |     |     |     | 270 |     |     |      |
| tcc | cgg | acc | cct | gag | gtc | aca | tgc | gtg | gtg | gtg | gac | gtg | agc | cac | gaa | 865  |
| Ser | Arg | Thr | Pro | Glu | Val | Thr | Cys | Val | Val | Val | Asp | Val | Ser | His | Glu |      |
|     |     | 275 |     |     |     |     | 280 |     |     |     |     | 285 |     |     |     |      |
| gac | cct | gag | gtc | aag | ttc | aac | tgg | tac | gtg | gac | ggc | gtg | gag | gtg | cat | 913  |
| Asp | Pro | Glu | Val | Lys | Phe | Asn | Trp | Tyr | Val | Asp | Gly | Val | Glu | Val | His |      |
|     | 290 |     |     |     |     | 295 |     |     |     |     | 300 |     |     |     |     |      |
| aat | gcc | aag | aca | aag | ccg | cgg | gag | gag | cag | tac | aac | agc | acg | tac | cgt | 961  |
| Asn | Ala | Lys | Thr | Lys | Pro | Arg | Glu | Glu | Gln | Tyr | Asn | Ser | Thr | Tyr | Arg |      |
| 305 |     |     |     |     | 310 |     |     |     |     | 315 |     |     |     |     | 320 |      |
| gtg | gtc | agc | gtc | ctc | acc | gtc | ctg | cac | cag | gac | tgg | ctg | aat | ggc | aag | 1009 |
| Val | Val | Ser | Val | Leu | Thr | Val | Leu | His | Gln | Asp | Trp | Leu | Asn | Gly | Lys |      |
|     |     |     |     | 325 |     |     |     |     | 330 |     |     |     |     | 335 |     |      |
| gag | tac | aag | tgc | aag | gtc | tcc | aac | aaa | gcc | ctc | cca | gcc | ccc | atc | gag | 1057 |
| Glu | Tyr | Lys | Cys | Lys | Val | Ser | Asn | Lys | Ala | Leu | Pro | Ala | Pro | Ile | Glu |      |
|     |     |     | 340 |     |     |     |     | 345 |     |     |     |     | 350 |     |     |      |
| aaa | acc | atc | tcc | aaa | gcc | aaa | ggg | cag | ccc | cga | gaa | cca | cag | gtg | tac | 1105 |
| Lys | Thr | Ile | Ser | Lys | Ala | Lys | Gly | Gln | Pro | Arg | Glu | Pro | Gln | Val | Tyr |      |
|     |     | 355 |     |     |     |     | 360 |     |     |     |     | 365 |     |     |     |      |
| acc | ctg | ccc | cca | tcc | cgg | gag | gag | atg | acc | aag | aac | cag | gtc | agc | ctg | 1153 |
| Thr | Leu | Pro | Pro | Ser | Arg | Glu | Glu | Met | Thr | Lys | Asn | Gln | Val | Ser | Leu |      |
|     | 370 |     |     |     |     | 375 |     |     |     |     | 380 |     |     |     |     |      |
| acc | tgc | ctg | gtc | aaa | ggc | ttc | tat | ccc | agc | gac | atc | gcc | gtg | gag | tgg | 1201 |
| Thr | Cys | Leu | Val | Lys | Gly | Phe | Tyr | Pro | Ser | Asp | Ile | Ala | Val | Glu | Trp |      |
| 385 |     |     |     |     | 390 |     |     |     |     | 395 |     |     |     |     | 400 |      |
| gag | agc | aat | ggg | cag | ccg | gag | aac | aac | tac | aag | acc | acg | cct | ccc | gtg | 1249 |
| Glu | Ser | Asn | Gly | Gln | Pro | Glu | Asn | Asn | Tyr | Lys | Thr | Thr | Pro | Pro | Val |      |

```
                          405                 410                 415
ctg gac tcc gac ggc tcc ttc ttc ctc tac agc aag ctc acc gtg gac    1297
Leu Asp Ser Asp Gly Ser Phe Phe Leu Tyr Ser Lys Leu Thr Val Asp
            420                 425                 430 aag agc agg tgg cag cag ggg aac gtc ttc tca tgc tcc gtg atg cat    1345
Lys Ser Arg Trp Gln Gln Gly Asn Val Phe Ser Cys Ser Val Met His
        435                 440                 445 gag gct ctg cac aac cac tac acg cag aag agc ctc tcc ctg tct ccg    1393
Glu Ala Leu His Asn His Tyr Thr Gln Lys Ser Leu Ser Leu Ser Pro
    450                 455                 460 ggt aaa tga                                                        1402
Gly Lys
465

<210> SEQ ID NO 18
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 18

Met Asp Met Arg Val Ser Ala Gln Leu Leu Gly Leu Leu Leu Leu Trp
1               5                   10                  15

Leu Ser Gly Ala Arg Cys Asp Ile Gln Met Thr Gln Ser Pro Ser Ser
            20                  25                  30

Leu Ser Ala Ser Ile Gly Asp Arg Val Thr Ile Thr Cys Lys Ala Ser
        35                  40                  45

Gln Asp Ile Asn Ser Tyr Leu Ser Trp Phe Gln Gln Lys Pro Gly Lys
    50                  55                  60

Ala Pro Lys Leu Leu Ile Tyr Arg Ala Asn Arg Leu Val Asp Gly Val
65                  70                  75                  80

Pro Ser Arg Phe Ser Gly Ser Gly Ser Gly Thr Asp Tyr Thr Leu Thr
                85                  90                  95

Ile Ser Ser Leu Gln Pro Glu Asp Phe Ala Val Tyr Tyr Cys Leu Gln
            100                 105                 110

Tyr Asp Glu Phe Pro Tyr Thr Phe Gly Gly Gly Thr Lys Leu Glu Ile
        115                 120                 125

Lys Arg Thr Val Ala Ala Pro Ser Val Phe Ile Phe Pro Pro Ser Asp
    130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
        195                 200                 205

Glu Lys His Lys Val Tyr Ala Cys Glu Val Thr His Gln Gly Leu Ser
    210                 215                 220

Ser Pro Val Thr Lys Ser Phe Asn Arg Gly Glu Cys
225                 230                 235

<210> SEQ ID NO 19
<211> LENGTH: 711
<212> TYPE: DNA
<213> ORGANISM: Artificial Sequence
<220> FEATURE:
```

<223> OTHER INFORMATION: Description of Artificial Sequence: Synthetic
      polynucleotide

<400> SEQUENCE: 19

```
atggacatga gggtctctgc tcagctcctg gggctcctgc tgctctggct ctcaggggcc      60
aggtgtgaca tccagatgac acagtctcca tcttccctgt ctgcatctat aggagacaga     120
gtcactatca cttgcaaggc gagtcaggac attaatagct atttaagctg gttccagcag     180
aaaccaggga agctcctaa gctgctgatc tatcgtgcaa acagattggt agatggggtt      240
ccatcaaggt tcagtggcag tggatctggg acagattata ctctcaccat cagcagcctg     300
cagcctgaag atttcgcagt ttattattgt ctacagtatg atgagtttcc gtacacgttc     360
ggagggggga ccaagctgga aataaaacgt acggtggctg caccatctgt cttcatcttc     420
ccgccatctg atgagcagtt gaaatctgga actgcctctg ttgtgtgcct gctgaataac     480
ttctatccca gagaggccaa agtacagtgg aaggtggata acgccctcca atcgggtaac     540
tcccaggaga gtgtcacaga gcaggacagc aaggacagca cctacagcct cagcagcacc     600
ctgacgctga gcaaagcaga ctacgagaaa cacaaagtct acgcctgcga agtcacccat     660
cagggcctga gctcgcccgt cacaaagagc ttcaacaggg gagagtgtta g              711
```

<210> SEQ ID NO 20
<211> LENGTH: 765
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (55)..(762)

<400> SEQUENCE: 20

```
tttccatggg tcttttctgc agtcaccgtc cttgacacga agcttgccgc cacc atg        57
                                                             Met
                                                             1 gac atg agg gtc tct gct cag ctc ctg ggg ctc ctg ctg ctc tgg ctc       105
Asp Met Arg Val Ser Ala Gln Leu Leu Gly Leu Leu Leu Leu Trp Leu
        5                   10                  15 tca ggg gcc agg tgt gac atc cag atg aca cag tct cca tct tcc ctg       153
Ser Gly Ala Arg Cys Asp Ile Gln Met Thr Gln Ser Pro Ser Ser Leu
         20                  25                  30 tct gca tct ata gga gac aga gtc act atc act tgc aag gcg agt cag       201
Ser Ala Ser Ile Gly Asp Arg Val Thr Ile Thr Cys Lys Ala Ser Gln
 35                  40                  45 gac att aat agc tat tta agc tgg ttc cag cag aaa cca ggg aaa gct       249
Asp Ile Asn Ser Tyr Leu Ser Trp Phe Gln Gln Lys Pro Gly Lys Ala
50                  55                  60                  65 cct aag ctg ctg atc tat cgt gca aac aga ttg gta gat ggg gtt cca       297
Pro Lys Leu Leu Ile Tyr Arg Ala Asn Arg Leu Val Asp Gly Val Pro
                 70                  75                  80 tca agg ttc agt ggc agt gga tct ggg aca gat tat act ctc acc atc       345
Ser Arg Phe Ser Gly Ser Gly Ser Gly Thr Asp Tyr Thr Leu Thr Ile
             85                  90                  95 agc agc ctg cag cct gaa gat ttc gca gtt tat tat tgt cta cag tat       393
Ser Ser Leu Gln Pro Glu Asp Phe Ala Val Tyr Tyr Cys Leu Gln Tyr
         100                 105                 110 gat gag ttt ccg tac acg ttc gga ggg gga acc aag ctg gaa ata aaa       441
Asp Glu Phe Pro Tyr Thr Phe Gly Gly Gly Thr Lys Leu Glu Ile Lys
     115                 120                 125 cgt acg gtg gct gca cca tct gtc ttc atc ttc ccg cca tct gat gag       489
Arg Thr Val Ala Ala Pro Ser Val Phe Ile Phe Pro Pro Ser Asp Glu
```

```
Arg Thr Val Ala Ala Pro Ser Val Phe Ile Phe Pro Pro Ser Asp Glu
130                 135                 140                 145 cag ttg aaa tct gga act gcc tct gtt gtg tgc ctg ctg aat aac ttc    537
Gln Leu Lys Ser Gly Thr Ala Ser Val Val Cys Leu Leu Asn Asn Phe
                150                 155                 160 tat ccc aga gag gcc aaa gta cag tgg aag gtg gat aac gcc ctc caa    585
Tyr Pro Arg Glu Ala Lys Val Gln Trp Lys Val Asp Asn Ala Leu Gln
            165                 170                 175 tcg ggt aac tcc cag gag agt gtc aca gag cag gac agc aag gac agc    633
Ser Gly Asn Ser Gln Glu Ser Val Thr Glu Gln Asp Ser Lys Asp Ser
        180                 185                 190 acc tac agc ctc agc agc acc ctg acg ctg agc aaa gca gac tac gag    681
Thr Tyr Ser Leu Ser Ser Thr Leu Thr Leu Ser Lys Ala Asp Tyr Glu
    195                 200                 205 aaa cac aaa gtc tac gcc tgc gaa gtc acc cat cag ggc ctg agc tcg    729
Lys His Lys Val Tyr Ala Cys Glu Val Thr His Gln Gly Leu Ser Ser
210                 215                 220                 225 ccc gtc aca aag agc ttc aac agg gga gag tgt tag                    765
Pro Val Thr Lys Ser Phe Asn Arg Gly Glu Cys
                230                 235

<210> SEQ ID NO 21
<211> LENGTH: 462
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 21

Met Gly Trp Ser Arg Ile Phe Leu Phe Leu Leu Ser Ile Ile Ala Gly
1               5                   10                  15

Val His Cys Gln Val Gln Leu Gln Gln Ser Gly Ser Glu Leu Lys Lys
                20                  25                  30

Pro Gly Ala Ser Val Lys Ile Ser Cys Lys Ala Ser Gly Tyr Ser Phe
            35                  40                  45

Thr Asp Tyr Ile Ile Leu Trp Val Arg Gln Asn Pro Gly Lys Gly Leu
        50                  55                  60

Glu Trp Ile Gly His Ile Asp Pro Tyr Tyr Gly Ser Ser Asn Tyr Asn
65                  70                  75                  80

Leu Lys Phe Lys Gly Arg Val Thr Ile Thr Ala Asp Gln Ser Thr Thr
                85                  90                  95

Thr Ala Tyr Met Glu Leu Ser Ser Leu Arg Ser Glu Asp Thr Ala Val
                100                 105                 110

Tyr Tyr Cys Gly Arg Ser Lys Arg Asp Tyr Phe Asp Tyr Trp Gly Gln
            115                 120                 125

Gly Thr Thr Leu Thr Val Ser Ser Ala Ser Thr Lys Gly Pro Ser Val
        130                 135                 140

Phe Pro Leu Ala Pro Cys Ser Arg Ser Thr Ser Glu Ser Thr Ala Ala
145                 150                 155                 160

Leu Gly Cys Leu Val Lys Asp Tyr Phe Pro Glu Pro Val Thr Val Ser
                165                 170                 175

Trp Asn Ser Gly Ala Leu Thr Ser Gly Val His Thr Phe Pro Ala Val
                180                 185                 190

Leu Gln Ser Ser Gly Leu Tyr Ser Leu Ser Ser Val Val Thr Val Pro
            195                 200                 205

Ser Ser Asn Phe Gly Thr Gln Thr Tyr Thr Cys Asn Val Asp His Lys
        210                 215                 220
```

```
Pro Ser Asn Thr Lys Val Asp Lys Thr Val Glu Arg Lys Cys Cys Val
225                 230                 235                 240

Glu Cys Pro Pro Cys Pro Ala Pro Pro Val Ala Gly Pro Ser Val Phe
            245                 250                 255

Leu Phe Pro Pro Lys Pro Lys Asp Thr Leu Met Ile Ser Arg Thr Pro
        260                 265                 270

Glu Val Thr Cys Val Val Val Asp Val Ser Gln Glu Asp Pro Glu Val
    275                 280                 285

Gln Phe Asn Trp Tyr Val Asp Gly Val Glu Val His Asn Ala Lys Thr
290                 295                 300

Lys Pro Arg Glu Glu Gln Phe Asn Ser Thr Tyr Arg Val Val Ser Val
305                 310                 315                 320

Leu Thr Val Leu His Gln Asp Trp Leu Asn Gly Lys Glu Tyr Lys Cys
            325                 330                 335

Lys Val Ser Asn Lys Gly Leu Pro Ser Ser Ile Glu Lys Thr Ile Ser
        340                 345                 350

Lys Ala Lys Gly Gln Pro Arg Glu Pro Gln Val Tyr Thr Leu Pro Pro
    355                 360                 365

Ser Gln Glu Glu Met Thr Lys Asn Gln Val Ser Leu Thr Cys Leu Val
370                 375                 380

Lys Gly Phe Tyr Pro Ser Asp Ile Ala Val Glu Trp Glu Ser Asn Gly
385                 390                 395                 400

Gln Pro Glu Asn Asn Tyr Lys Thr Thr Pro Pro Val Leu Asp Ser Asp
            405                 410                 415

Gly Ser Phe Phe Leu Tyr Ser Arg Leu Thr Val Asp Lys Ser Arg Trp
        420                 425                 430

Gln Glu Gly Asn Val Phe Ser Cys Ser Val Met His Glu Ala Leu His
    435                 440                 445

Asn His Tyr Thr Gln Lys Ser Leu Ser Leu Ser Leu Gly Lys
450                 455                 460

<210> SEQ ID NO 22
<211> LENGTH: 2002
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
atgggatgga gctgtatcat cctcttcttg gtagcaacag ctacaggtgt ccactccctc      60
gaggtccagc tgcaacagtc tggacctgag ctggtgaagc ctggggcttc actgaagatg     120
tcctgcaagg cttctggtta ttcattcact gactacatca tactctgggt gaagcagaac     180
catggaaaga gccttgagtg gattggacat attgatcctt actatggtag ttctaactac     240
aatctgaaat tcaagggcaa ggccacattg actgtagaca atcttccagc acagcctac      300 atgcagctca cagtctgac atctgaggac tctgcagtct attactgtgg aagatctaag     360
agggactact ttgactactg gggccaaggc accactctca cagtttcctc agcctccacc     420
aagggcccat ccgtcttccc cctggcgccc tgctccagga gcacctccga gagcacagcc     480
gccctgggct gcctggtcaa ggactacttc cccgaaccgg tgacggtgtc gtggaactca     540
ggcgccctga ccagcggcgt gcacaccttc ccggctgtcc tacagtcctc aggactctac     600
tccctcagca gcgtggtgac cgtgccctcc agcaacttcg gcacccagac ctacacctgc     660
aacgtagatc acaagcccag caacaccaag gtggacaaga cagttggtga gaggccagct     720
```

```
cagggaggga gggtgtctgc tggaagccag gctcagccct cctgcctgga cgcaccccgg      780
ctgtgcagcc ccagcccagg gcagcaaggc aggccccatc tgtctcctca cccggaggcc      840
tctgcccgcc ccactcatgc tcagggagag ggtcttctgg cttttccac caggctccag       900 gcaggcacag gctgggtgcc cctaccccag gcccttcaca cacaggggca ggtgcttggc      960
tcagacctgc caaaagccat atccgggagg accctgcccc tgacctaagc cgaccccaaa     1020
ggccaaactg tccactccct cagctcggac accttctctc ctcccagatc cgagtaactc     1080
ccaatcttct ctctgcagag cgcaaatgtt gtgtcgagtg cccaccgtgc ccaggtaagc     1140
cagcccaggc ctcgccctcc agctcaaggc gggacaggtg ccctagagta gcctgcatcc     1200
agggacaggc cccagctggg tgctgacacg tccacctcca tctcttcctc agcaccacct     1260
gtggcaggac cgtcagtctt cctcttcccc ccaaaaccca aggacaccct catgatctcc     1320 cggaccccctg aggtcacgtg cgtggtggtg gacgtgagcc aggaagaccc cgaggtccag    1380
ttcaactggt acgtggatgg cgtggaggtg cataatgcca agacaaagcc gcgggaggag     1440
cagttcaaca gcacgtaccg tgtggtcagc gtcctcaccg tcctgcacca ggactggctg     1500
aacggcaagg agtacaagtg caaggtctcc aacaaaggcc tcccgtcctc catcgagaaa    1560
accatctcca aagccaaagg tgggacccac ggggtgcgag ggccacatgg acagaggtca    1620
gctcggccca ccctctgccc tgggagtgac cgctgtgcca acctctgtcc ctacagggca    1680
gccccgagag ccacaggtgt acaccctgcc cccatcccag gaggagatga ccaagaacca    1740
ggtcagcctg acctgcctgg tcaaaggctt ctaccccagc gacatcgccg tggagtggga    1800
gagcaatggg cagccggaga caactacaa gaccacgcct cccgtgctgg actccgacgg    1860
ctccttcttc ctctacagca ggctaaccgt ggacaagagc aggtggcagg aggggaatgt    1920
cttctcatgc tccgtgatgc atgaggctct gcacaaccac tacacacaga gagcctctc     1980 cctgtctctg ggtaaatgat ga                                              2002

<210> SEQ ID NO 23
<211> LENGTH: 2163
<212> TYPE: DNA
<213> ORGANISM: Artificial Sequence
<220> FEATURE:
<223> OTHER INFORMATION: Description of Artificial Sequence: Synthetic
      polynucleotide
<220> FEATURE:
<221> NAME/KEY: CDS
<222> LOCATION: (94)..(798)
<220> FEATURE:
<221> NAME/KEY: CDS
<222> LOCATION: (1191)..(1226)
<220> FEATURE:
<221> NAME/KEY: CDS
<222> LOCATION: (1345)..(1671)
<220> FEATURE:
<221> NAME/KEY: CDS
<222> LOCATION: (1769)..(2089)

<400> SEQUENCE: 23
ccaccagaca taatagctga cagactaaca gactgttcct ttccatgggt cttttctgca      60
gtcaccgtcc ttgacacgaa gcttgccgcc acc atg gga tgg agc tgt atc atc     114
                                    Met Gly Trp Ser Cys Ile Ile
                                    1               5 ctc ttc ttg gta gca aca gct aca ggt gtc cac tcc ctc gag gtc cag      162
Leu Phe Leu Val Ala Thr Ala Thr Gly Val His Ser Leu Glu Val Gln
        10                  15                  20 ctg caa cag tct gga cct gag ctg gtg aag cct ggg gct tca ctg aag      210
Leu Gln Gln Ser Gly Pro Glu Leu Val Lys Pro Gly Ala Ser Leu Lys
25                  30                  35
```

```
atg tcc tgc aag gct tct ggt tat tca ttc act gac tac atc ata ctc      258
Met Ser Cys Lys Ala Ser Gly Tyr Ser Phe Thr Asp Tyr Ile Ile Leu
40              45                  50                  55 tgg gtg aag cag aac cat gga aag agc ctt gag tgg att gga cat att      306
Trp Val Lys Gln Asn His Gly Lys Ser Leu Glu Trp Ile Gly His Ile
                60                  65                  70 gat cct tac tat ggt agt tct aac tac aat ctg aaa ttc aag ggc aag      354
Asp Pro Tyr Tyr Gly Ser Ser Asn Tyr Asn Leu Lys Phe Lys Gly Lys
            75                  80                  85 gcc aca ttg act gta gac aaa tct tcc agc aca gcc tac atg cag ctc      402
Ala Thr Leu Thr Val Asp Lys Ser Ser Ser Thr Ala Tyr Met Gln Leu
        90                  95                 100 aac agt ctg aca tct gag gac tct gca gtc tat tac tgt gga aga tct      450
Asn Ser Leu Thr Ser Glu Asp Ser Ala Val Tyr Tyr Cys Gly Arg Ser
    105                 110                 115 aag agg gac tac ttt gac tac tgg ggc caa ggc acc act ctc aca gtt      498
Lys Arg Asp Tyr Phe Asp Tyr Trp Gly Gln Gly Thr Thr Leu Thr Val
120                 125                 130                 135 tcc tca gcc tcc acc aag ggc cca tcc gtc ttc ccc ctg gcg ccc tgc      546
Ser Ser Ala Ser Thr Lys Gly Pro Ser Val Phe Pro Leu Ala Pro Cys
                140                 145                 150 tcc agg agc acc tcc gag agc aca gcc gcc ctg ggc tgc ctg gtc aag      594
Ser Arg Ser Thr Ser Glu Ser Thr Ala Ala Leu Gly Cys Leu Val Lys
            155                 160                 165 gac tac ttc ccc gaa ccg gtg acg gtg tcg tgg aac tca ggc gcc ctg      642
Asp Tyr Phe Pro Glu Pro Val Thr Val Ser Trp Asn Ser Gly Ala Leu
        170                 175                 180 acc agc ggc gtg cac acc ttc ccg gct gtc cta cag tcc tca gga ctc      690
Thr Ser Gly Val His Thr Phe Pro Ala Val Leu Gln Ser Ser Gly Leu
    185                 190                 195 tac tcc ctc agc agc gtg gtg acc gtg ccc tcc agc aac ttc ggc acc      738
Tyr Ser Leu Ser Ser Val Val Thr Val Pro Ser Ser Asn Phe Gly Thr
200                 205                 210                 215 cag acc tac acc tgc aac gta gat cac aag ccc agc aac acc aag gtg      786
Gln Thr Tyr Thr Cys Asn Val Asp His Lys Pro Ser Asn Thr Lys Val
                220                 225                 230 gac aag aca gtt ggtgagaggc cagctcaggg agggaggtg tctgctggaa           838
Asp Lys Thr Val
            235 gccaggctca gccctcctgc ctggacgcac cccggctgtg cagccccagc ccagggcagc    898 aaggcaggcc ccatctgtct cctcacccgg aggcctctgc ccgccccact catgctcagg    958 gagagggtct tctggctttt tccaccaggc tccaggcagg cacaggctgg gtgccctac     1018 cccaggccct tcacacacag gggcaggtgc ttggctcaga cctgccaaaa gccatatccg    1078 ggaggaccct gccctgacc taagccgacc ccaaaggcca aactgtccac tccctcagct    1138 cggacacctt ctctcctccc agatccgagt aactcccaat cttctctctg ca gag cgc   1196
                                                          Glu Arg aaa tgt tgt gtc gag tgc cca ccg tgc cca ggtaagccag cccaggcctc        1246
Lys Cys Cys Val Glu Cys Pro Pro Cys Pro
240                 245 gccctccagc tcaaggcggg acaggtgccc tagagtagcc tgcatccagg acaggcccc     1306 agctgggtgc tgacacgtcc acctccatct cttcctca gca cca cct gtg gca gga   1362
                                          Ala Pro Pro Val Ala Gly
                                                          250 ccg tca gtc ttc ctc ttc ccc cca aaa ccc aag gac acc ctc atg atc      1410
Pro Ser Val Phe Leu Phe Pro Pro Lys Pro Lys Asp Thr Leu Met Ile
255                 260                 265
```

```
tcc cgg acc cct gag gtc acg tgc gtg gtg gtg gac gtg agc cag gaa    1458
Ser Arg Thr Pro Glu Val Thr Cys Val Val Val Asp Val Ser Gln Glu
270                 275                 280                 285 gac ccc gag gtc cag ttc aac tgg tac gtg gat ggc gtg gag gtg cat    1506
Asp Pro Glu Val Gln Phe Asn Trp Tyr Val Asp Gly Val Glu Val His
                290                 295                 300 aat gcc aag aca aag ccg cgg gag gag cag ttc aac agc acg tac cgt    1554
Asn Ala Lys Thr Lys Pro Arg Glu Glu Gln Phe Asn Ser Thr Tyr Arg
            305                 310                 315 gtg gtc agc gtc ctc acc gtc ctg cac cag gac tgg ctg aac ggc aag    1602
Val Val Ser Val Leu Thr Val Leu His Gln Asp Trp Leu Asn Gly Lys
        320                 325                 330 gag tac aag tgc aag gtc tcc aac aaa ggc ctc ccg tcc tcc atc gag    1650
Glu Tyr Lys Cys Lys Val Ser Asn Lys Gly Leu Pro Ser Ser Ile Glu
    335                 340                 345 aaa acc atc tcc aaa gcc aaa ggtgggaccc acggggtgcg agggccacat       1701
Lys Thr Ile Ser Lys Ala Lys
350                 355 ggacagaggt cagctcggcc caccctctgc cctgggagtg accgctgtgc caacctctgt    1761 ccctaca ggg cag ccc cga gag cca cag gtg tac acc ctg ccc cca tcc     1810
        Gly Gln Pro Arg Glu Pro Gln Val Tyr Thr Leu Pro Pro Ser
                360                 365                 370 cag gag gag atg acc aag aac cag gtc agc ctg acc tgc ctg gtc aaa    1858
Gln Glu Glu Met Thr Lys Asn Gln Val Ser Leu Thr Cys Leu Val Lys
                375                 380                 385 ggc ttc tac ccc agc gac atc gcc gtg gag tgg gag agc aat ggg cag    1906
Gly Phe Tyr Pro Ser Asp Ile Ala Val Glu Trp Glu Ser Asn Gly Gln
            390                 395                 400 ccg gag aac aac tac aag acc acg cct ccc gtg ctg gac tcc gac ggc    1954
Pro Glu Asn Asn Tyr Lys Thr Thr Pro Pro Val Leu Asp Ser Asp Gly
        405                 410                 415 tcc ttc ttc ctc tac agc agg cta acc gtg gac aag agc agg tgg cag    2002
Ser Phe Phe Leu Tyr Ser Arg Leu Thr Val Asp Lys Ser Arg Trp Gln
    420                 425                 430 gag ggg aat gtc ttc tca tgc tcc gtg atg cat gag gct ctg cac aac    2050
Glu Gly Asn Val Phe Ser Cys Ser Val Met His Glu Ala Leu His Asn
435                 440                 445                 450 cac tac aca cag aag agc ctc tcc ctg tct ctg ggt aaa tgatgagaat     2099
His Tyr Thr Gln Lys Ser Leu Ser Leu Ser Leu Gly Lys
                455                 460 tcattgatca taatcagcca taccacattt gtagaggttt tacttgcttt aaaaaacctc    2159
ccac                                                                2163

<210> SEQ ID NO 24
<211> LENGTH: 236
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Met Asp Met Arg Val Ser Ala Gln Leu Leu Gly Leu Leu Leu Leu Trp
1               5                   10                  15

Leu Ser Gly Ala Arg Cys Asp Ile Gln Met Thr Gln Ser Pro Ser Ser
            20                  25                  30

Leu Ser Ala Ser Ile Gly Asp Arg Val Thr Ile Thr Cys Lys Ala Ser
        35                  40                  45

Gln Asp Ile Asn Ser Tyr Leu Ser Trp Phe Gln Gln Lys Pro Gly Lys
    50                  55                  60
```

```
Ala Pro Lys Leu Leu Ile Tyr Arg Ala Asn Arg Leu Val Asp Gly Val
 65                  70                  75                  80

Pro Ser Arg Phe Ser Gly Ser Gly Thr Asp Tyr Thr Leu Thr
             85                  90                  95

Ile Ser Ser Leu Gln Pro Glu Asp Phe Ala Val Tyr Tyr Cys Leu Gln
            100                 105                 110

Tyr Asp Glu Phe Pro Tyr Thr Phe Gly Gly Gly Thr Lys Leu Glu Ile
            115                 120                 125

Lys Arg Thr Val Ala Ala Pro Ser Val Phe Ile Phe Pro Pro Ser Asp
130                 135                 140

Glu Gln Leu Lys Ser Gly Thr Ala Ser Val Val Cys Leu Leu Asn Asn
145                 150                 155                 160

Phe Tyr Pro Arg Glu Ala Lys Val Gln Trp Lys Val Asp Asn Ala Leu
                165                 170                 175

Gln Ser Gly Asn Ser Gln Glu Ser Val Thr Glu Gln Asp Ser Lys Asp
            180                 185                 190

Ser Thr Tyr Ser Leu Ser Ser Thr Leu Thr Leu Ser Lys Ala Asp Tyr
            195                 200                 205

Glu Lys His Lys Val Tyr Ala Cys Glu Val Thr His Gln Gly Leu Ser
210                 215                 220

Ser Pro Val Thr Lys Ser Phe Asn Arg Gly Glu Cys
225                 230                 235
```

<210> SEQ ID NO 25
<211> LENGTH: 711
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 25

```
atggacatga gggtctctgc tcagctcctg gggctcctgc tgctctggct ctcaggggcc      60
aggtgtgaca tccagatgac acagtctcca tcttccctgt ctgcatctat aggagacaga     120
gtcactatca cttgcaaggc gagtcaggac attaatagct atttaagctg gttccagcag     180
aaaccaggga aagctcctaa gctgctgatc tatcgtgcaa acagattggt agatggggtt     240
ccatcaaggt tcagtggcag tggatctggg acagattata ctctcaccat cagcagcctg     300
cagcctgaag atttcgcagt ttattattgt ctacagtatg atgagtttcc gtacacgttc     360
ggaggggggga ccaagctgga aataaaacgt acggtggctg caccatctgt cttcatcttc     420
ccgccatctg atgagcagtt gaaatctgga actgcctctg ttgtgtgcct gctgaataac     480
ttctatccca gagaggccaa agtacagtgg aaggtggata acgccctcca atcgggtaac     540
tcccaggaga gtgtcacaga gcaggacagc aaggacagca cctacagcct cagcagcacc     600
ctgacgctga gcaaagcaga ctacgagaaa cacaaagtct acgcctgcga agtcacccat     660
cagggcctga gctcgcccgt cacaaagagc ttcaacaggg gagagtgtta g              711
```

<210> SEQ ID NO 26
<211> LENGTH: 765
<212> TYPE: DNA
<213> ORGANISM: Artificial Sequence
<220> FEATURE:
<223> OTHER INFORMATION: Description of Artificial Sequence: Synthetic polynucleotide
<220> FEATURE:
<221> NAME/KEY: CDS
<222> LOCATION: (55)..(762)

<400> SEQUENCE: 26

```
tttccatggg tcttttctgc agtcaccgtc cttgacacga agcttgccgc cacc atg      57
                                                             Met
                                                             1 gac atg agg gtc tct gct cag ctc ctg ggg ctc ctg ctc tgg ctc         105
Asp Met Arg Val Ser Ala Gln Leu Leu Gly Leu Leu Leu Trp Leu
          5                  10                  15 tca ggg gcc agg tgt gac atc cag atg aca cag tct cca tct tcc ctg    153
Ser Gly Ala Arg Cys Asp Ile Gln Met Thr Gln Ser Pro Ser Ser Leu
         20                  25                  30 tct gca tct ata gga gac aga gtc act atc act tgc aag gcg agt cag    201
Ser Ala Ser Ile Gly Asp Arg Val Thr Ile Thr Cys Lys Ala Ser Gln
     35                  40                  45 gac att aat agc tat tta agc tgg ttc cag cag aaa cca ggg aaa gct    249
Asp Ile Asn Ser Tyr Leu Ser Trp Phe Gln Gln Lys Pro Gly Lys Ala
 50                  55                  60                  65 cct aag ctg ctg atc tat cgt gca aac aga ttg gta gat ggg gtt cca    297
Pro Lys Leu Leu Ile Tyr Arg Ala Asn Arg Leu Val Asp Gly Val Pro
                 70                  75                  80 tca agg ttc agt ggc agt gga tct ggg aca gat tat act ctc acc atc    345
Ser Arg Phe Ser Gly Ser Gly Ser Gly Thr Asp Tyr Thr Leu Thr Ile
             85                  90                  95 agc agc ctg cag cct gaa gat ttc gca gtt tat tat tgt cta cag tat    393
Ser Ser Leu Gln Pro Glu Asp Phe Ala Val Tyr Tyr Cys Leu Gln Tyr
         100                 105                 110 gat gag ttt ccg tac acg ttc gga ggg ggg acc aag ctg gaa ata aaa    441
Asp Glu Phe Pro Tyr Thr Phe Gly Gly Gly Thr Lys Leu Glu Ile Lys
    115                 120                 125 cgt acg gtg gct gca cca tct gtc ttc atc ttc ccg cca tct gat gag    489
Arg Thr Val Ala Ala Pro Ser Val Phe Ile Phe Pro Pro Ser Asp Glu
130                 135                 140                 145 cag ttg aaa tct gga act gcc tct gtt gtg tgc ctg ctg aat aac ttc    537
Gln Leu Lys Ser Gly Thr Ala Ser Val Val Cys Leu Leu Asn Asn Phe
                150                 155                 160 tat ccc aga gag gcc aaa gta cag tgg aag gtg gat aac gcc ctc caa    585
Tyr Pro Arg Glu Ala Lys Val Gln Trp Lys Val Asp Asn Ala Leu Gln
            165                 170                 175 tcg ggt aac tcc cag gag agt gtc aca gag cag gac agc aag gac agc    633
Ser Gly Asn Ser Gln Glu Ser Val Thr Glu Gln Asp Ser Lys Asp Ser
        180                 185                 190 acc tac agc ctc agc agc acc ctg acg ctg agc aaa gca gac tac gag    681
Thr Tyr Ser Leu Ser Ser Thr Leu Thr Leu Ser Lys Ala Asp Tyr Glu
    195                 200                 205 aaa cac aaa gtc tac gcc tgc gaa gtc acc cat cag ggc ctg agc tcg    729
Lys His Lys Val Tyr Ala Cys Glu Val Thr His Gln Gly Leu Ser Ser
210                 215                 220                 225 ccc gtc aca aag agc ttc aac agg gga gag tgt tag                    765
Pro Val Thr Lys Ser Phe Asn Arg Gly Glu Cys
                230                 235
```

<210> SEQ ID NO 27
<211> LENGTH: 448
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 27

Glu Val Gln Leu Val Glu Ser Gly Gly Gly Leu Val Lys Pro Gly Arg
1               5                   10                  15

```
Ser Leu Lys Leu Ser Cys Ala Ala Ser Gly Phe Thr Phe Ser Asp Tyr
         20                  25                  30

Tyr Met Ala Trp Val Arg Gln Ala Pro Lys Gly Leu Glu Trp Val
         35                  40                  45

Ala Ser Ile Gly Tyr Glu Gly Thr Ser Thr Tyr Tyr Gly Asp Ser Val
 50                  55                  60

Lys Gly Arg Phe Thr Ile Ser Arg Asp Asn Ala Lys Ser Thr Leu Tyr
 65                  70                  75                  80

Leu Gln Met Asn Ser Leu Arg Ser Glu Asp Thr Ala Thr Tyr Tyr Cys
             85                  90                  95

Thr Arg Leu Glu Leu Ala Gly Val Met Asp Ala Trp Gly Gln Gly Ala
             100                 105                 110

Ser Val Thr Val Ser Ser Ala Lys Thr Thr Ala Pro Ser Val Tyr Pro
         115                 120                 125

Leu Ala Pro Val Cys Gly Asp Thr Thr Gly Ser Ser Val Thr Leu Gly
 130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
             165                 170                 175

Ser Asp Leu Tyr Thr Leu Ser Ser Ser Val Thr Val Thr Ser Ser Thr
             180                 185                 190

Trp Pro Ser Gln Ser Ile Thr Cys Asn Val Ala His Pro Ala Ser Ser
         195                 200                 205

Thr Lys Val Asp Lys Lys Ile Glu Pro Arg Gly Pro Thr Ile Lys Pro
 210                 215                 220

Cys Pro Pro Cys Lys Cys Pro Ala Pro Asn Leu Glu Gly Gly Pro Ser
225                 230                 235                 240

Val Phe Ile Phe Pro Pro Lys Ile Lys Asp Val Leu Met Ile Ser Leu
             245                 250                 255

Ser Pro Ile Val Thr Cys Val Val Asp Val Ser Glu Asp Asp Pro
             260                 265                 270

Asp Val Gln Ile Ser Trp Phe Val Asn Asn Val Glu Val His Thr Ala
         275                 280                 285

Gln Thr Gln Thr His Arg Glu Asp Tyr Asn Ser Thr Leu Arg Val Val
 290                 295                 300

Ser Ala Leu Pro Ile Gln His Gln Asp Trp Met Ser Gly Lys Ala Phe
305                 310                 315                 320

Ala Cys Ala Val Asn Asn Lys Asp Leu Pro Ala Pro Ile Glu Arg Thr
             325                 330                 335

Ile Ser Lys Pro Lys Gly Ser Val Arg Ala Pro Gln Val Tyr Val Leu
         340                 345                 350

Pro Pro Pro Glu Glu Glu Met Thr Lys Lys Gln Val Thr Leu Thr Cys
         355                 360                 365

Met Val Thr Asp Phe Met Pro Glu Asp Ile Tyr Val Glu Trp Thr Asn
 370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
             405                 410                 415

Asn Trp Val Glu Arg Asn Ser Tyr Ser Cys Ser Val Val His Glu Gly
         420                 425                 430

Leu His Asn His His Thr Thr Lys Ser Phe Ser Arg Thr Pro Gly Lys
```

435        440        445

<210> SEQ ID NO 28
<211> LENGTH: 448
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 28

Glu Val Gln Leu Val Glu Ser Gly Gly Gly Leu Val Lys Pro Gly Arg
1               5                   10                  15

Ser Leu Lys Leu Ser Cys Ala Ala Ser Gly Phe Thr Phe Ser Asp Tyr
            20                  25                  30

Tyr Met Ala Trp Val Arg Gln Ala Pro Lys Lys Gly Leu Glu Trp Val
        35                  40                  45

Ala Ser Ile Gly Tyr Glu Gly Thr Ser Thr Tyr Tyr Gly Asp Ser Val
    50                  55                  60

Lys Gly Arg Phe Thr Ile Ser Arg Asp Asn Ala Lys Ser Thr Leu Tyr
65                  70                  75                  80

Leu Gln Met Asn Ser Leu Arg Ser Glu Asp Thr Ala Thr Tyr Tyr Cys
                85                  90                  95

Thr Arg Leu Glu Leu Ala Gly Val Met Asp Ala Trp Gly Gln Gly Ala
            100                 105                 110

Ser Val Thr Val Ser Ser Ala Lys Thr Thr Ala Pro Ser Val Tyr Pro
        115                 120                 125

Leu Ala Pro Val Cys Gly Asp Thr Thr Gly Ser Ser Val Thr Leu Gly
    130                 135                 140

Cys Leu Val Lys Gly Tyr Phe Pro Glu Pro Val Thr Leu Thr Trp Asn
145                 150                 155                 160

Ser Gly Ser Leu Ser Ser Gly Val His Thr Phe Pro Ala Val Leu Gln
                165                 170                 175

Ser Asp Leu Tyr Thr Leu Ser Ser Ser Val Thr Val Thr Ser Ser Thr
            180                 185                 190

Trp Pro Ser Gln Ser Ile Thr Cys Asn Val Ala His Pro Ala Ser Ser
        195                 200                 205

Thr Lys Val Asp Lys Lys Ile Glu Pro Arg Gly Pro Thr Ile Lys Pro
    210                 215                 220

Cys Pro Pro Cys Lys Cys Pro Ala Pro Asn Leu Leu Gly Gly Pro Ser
225                 230                 235                 240

Val Phe Ile Phe Pro Pro Lys Ile Lys Asp Val Leu Met Ile Ser Leu
                245                 250                 255

Ser Pro Ile Val Thr Cys Val Val Val Asp Val Ser Glu Asp Asp Pro
            260                 265                 270

Asp Val Gln Ile Ser Trp Phe Val Asn Asn Val Glu Val His Thr Ala
        275                 280                 285

Gln Thr Gln Thr His Arg Glu Asp Tyr Asn Ser Thr Leu Arg Val Val
    290                 295                 300

Ser Ala Leu Pro Ile Gln His Gln Asp Trp Met Ser Gly Lys Glu Phe
305                 310                 315                 320

Lys Cys Lys Val Asn Asn Lys Asp Leu Pro Ala Pro Ile Glu Arg Thr
                325                 330                 335

Ile Ser Lys Pro Lys Gly Ser Val Arg Ala Pro Gln Val Tyr Val Leu
            340                 345                 350

Pro Pro Pro Glu Glu Glu Met Thr Lys Lys Gln Val Thr Leu Thr Cys

-continued

```
                355                 360                 365
Met Val Thr Asp Phe Met Pro Glu Asp Ile Tyr Val Glu Trp Thr Asn
    370                 375                 380

Asn Gly Lys Thr Glu Leu Asn Tyr Lys Asn Thr Glu Pro Val Leu Asp
385                 390                 395                 400

Ser Asp Gly Ser Tyr Phe Met Tyr Ser Lys Leu Arg Val Glu Lys Lys
                405                 410                 415

Asn Trp Val Glu Arg Asn Ser Tyr Ser Cys Ser Val Val His Glu Gly
                420                 425                 430

Leu His Asn His His Thr Thr Lys Ser Phe Ser Arg Thr Pro Gly Lys
            435                 440                 445
```

ANTIBODIES TO OX-2/CD200 AND USES THEREOF IN INHIBITING IMMUNE RESPONSES

RELATED APPLICATIONS

This application is a continuation of U.S. application Ser. No. 12/670,379, filed Jul. 20, 2010, which is a national stage filing under 35 U.S.C. 371 of International Application PCT/US2008/009037, filed Jul. 25, 2008, which claims the benefit of U.S. Provisional Application No. 60/962,022, filed Jul. 25, 2007. The specifications of each of the foregoing applications are incorporated herein by reference in their entirety.

SEQUENCE LISTING

The instant application contains a Sequence Listing which has been submitted via EFS-Web and is hereby incorporated by reference in its entirety. Said ASCII copy, created on Aug. 24, 2012, is named ALXN132302_Seq.txt, and is 96,781 bytes in size.

TECHNICAL FIELD

The disclosure relates to OX-2/CD200 (herein referred to as CD200) binding agents and methods of preventing or inhibiting an immune response. The compositions and methods described herein may be used to treat patients with autoimmune disorders and graft recipients. The methods of therapy for promoting tolerance of grafts include administering a CD200-binding agent, such as an anti-CD200 antibody, to a transplant or graft recipient, thereby prolonging survival of the graft.

BACKGROUND

Immune cells help attack and eliminate foreign invaders such as infectious agents. However, in certain instances, such as in autoimmune disorders, allergies, and the rejection of tissue or organ transplants, the immune system can be the cause of illness. In transplantation of a graft (e.g., a cell, a tissue, or an organ) from a donor to a recipient, the recipient's immune reaction to the graft causes illness. Nevertheless, transplantation of cells, tissues and organs is very common and is often a life-saving procedure. Organ transplantation is the preferred treatment for most patients with chronic organ failure. Despite great improvement in treatments to inhibit immune rejection of a transplant (i.e., graft rejection), this rejection—which includes both acute and chronic rejection—continues to be the single largest impediment to successful organ transplantation. One-year survival rates for renal transplants, for example, average 88.3% with kidneys from deceased donors and 94.4% with kidneys received from living donors. The corresponding five-year survival rates for the transplanted kidneys are 63.3% and 76.5% (OPTN/SRTR Annual Report, 2002. Chapter 1 of the Annual Report produced by the Scientific Registry of Transplant Recipients (SRTR) in collaboration with the Organ Procurement and Transplantation Network (OPTN). See world wide web at unos.org/data/ar2002/ar02_chapter_one.htm.). For liver transplants, the one-year survival rates are 80.2% and 76.5% for livers from deceased and living donors, respectively. The corresponding five-year liver graft survival rates are 63.5% and 73.0% (OPTN/SRTR Annual Report, 2002. Chapter 1 of the Annual Report produced by the Scientific Registry of Transplant Recipients (SRTR) in collaboration with the Organ Procurement and Transplantation Network (OPTN). See world wide web at unos.org/data/ar2002/ar02_chapter_one.htm). The use of immunosuppressant drugs, especially cyclosporine A and more recently tacrolimus, has dramatically improved the success rate of organ transplantation. These agents have especially been successful in inhibiting acute rejection. Yet, as the numbers above show, there is still a need to improve both the short-term and especially the long-term survival rates following transplantation.

There are multiple types of transplants. A graft transplanted from one individual to the same individual is called an autologous graft or autograft. A graft transplanted between two genetically identical or syngeneic individuals is called a syngeneic graft. A graft transplanted between two genetically different individuals of the same species is called an allogeneic graft or allograft, and a graft transplanted between individuals of different species is called a xenogeneic graft or xenograft.

Currently more than 40,000 kidney, heart, lung, liver and pancreas transplants are performed in the United States each year (Abbas et al., 2000; *Cellular and Molecular Immunology* ($4^{th}$ edition), p. 363-383 (W.B. Saunders Company, New York). Other possible transplants include, but are not limited to, vascular tissue, eye, cornea, lens, skin, bone marrow, muscle, connective tissue, gastrointestinal tissue, nervous tissue, bone, stem cells, islets, cartilage, hepatocytes, and hematopoietic cells. Unfortunately, there are many more candidates for a transplant than there are donors. To overcome this shortage, a major effort is being made to learn how to use xenografts. While progress is being made in this field, at present most transplants are allografts.

In transplantation, therefore, the donor's genetic background is often different from the genetic background of the recipient (e.g., allotransplantation), and the donor and recipient thus differ in their histocompatibility antigens, i.e., antigens of the major histocompatibility complex (MHC), called the HLA system in humans. The recipient therefore recognizes the graft as a foreign substance, and various immune responses work to reject and eliminate the graft. Graft rejection refers to the immune responses of the recipient against the graft. The immune responses that act in graft rejection can be classified into (1) hyper-acute rejection, which is a strong rejection occurring immediately after transplantation; (2) acute rejection, which is observed within a few months after transplantation (also included is acute vascular rejection such as accelerated humoral rejection and de novo acute humoral rejection); and (3) chronic rejection observed several months after transplantation. Rejection is normally a result of T-cell mediated and/or humoral antibody attack, but may include additional secondary factors, cytokines and other immune cells such as macrophages. The molecules that the recipient's immune cells recognize as foreign on allografts are called alloantigens and these molecules on xenografts are called xenoantigens. The recipient's lymphocytes or antibodies that react with alloantigens or xenoantigens are described as being alloreactive or xenoreactive, respectively.

Cellular immunity (due to immunocompetent cells represented by T cells) and humoral immunity (due to antibodies) work in an intricately coordinated manner in graft rejection (see Rocha et al. 2003 *Immunol. Rev.* 196: 51-64). T cell responses to antigens from the donor organ are generally acknowledged to mediate acute rejection. In allotransplantation, CD8+ cytotoxic T cells recognize donor MHC molecules expressed on the allograft and/or on leukocytes (i.e., antigen-presenting cells) within the graft. In cases in which the allograft differs from the recipient at both class I and class II sites, recognition of the MHC molecules leads to activation of both CD8+ and CD4+ T cells. While allogeneic MHC antigens provide one signal to stimulate CD4+/T helper cells of the recipient, recipient macrophages provide a second signal, interleukin 1 (IL-1), which is essential to the activation of T helper cells. Activated T helper cells produce IL-2, which leads to the proliferation of cytotoxic T cells and lymphokine-activated killer cells and the release of IL-4 and IL-6. In addition, IL-2 promotes release of interferon gamma as well as tumor necrosis factor and other proinflammatory cytokines.

APCs (antigen-presenting cells, e.g., dendritic cells) are also involved in graft rejection, as mentioned above. Allograft and xenograft antigens can be processed and presented indirectly by recipient APCs, which may infiltrate the graft. Recipient APCs presenting donor antigens are transported to lymph nodes through the circulation, where they activate T cells. APC activity leads to lymphocyte proliferation and eventual T cell infiltration into the donor graft.

Another immune response in graft rejection is the production of anti-donor antibodies (such as alloantibodies in the case of an allograft), which is mediated by B-cells. This response, however, requires the activity of CD4+ T cells that stimulate B-cell growth, differentiation, and secretion of antibodies. Binding of alloantibodies to MHC antigens expressed on endothelial cells activates a complex response involving the complement and coagulation pathways, which ultimately results in inflammation and graft injury. Alloantibodies can also mediate antibody-dependent cellular cytotoxicity (ADCC) via the Fc region of the antibody molecule. The activities of alloantibodies and complement may be important for hyperacute, acute humoral, and chronic rejection of a graft, and alloantibodies to donor HLA class I or class II antigens have been associated with chronic rejection of various transplanted organs.

As a result of graft rejection, the graft ultimately becomes necrotic. Furthermore, the recipient develops not only severe systemic symptoms such as fever, leukocytosis and fatigue, but also swelling and tenderness at the transplantation site. Severe complications such as infections may also occur.

A limited number of immunosuppressive agents that suppress the function of immunocompetent cells are used to suppress graft rejection. Such immunosuppressive agents include cyclosporine (CsA); tacrolimus (FK-506); azathioprine (AZ); mycophenolate mofetil (MMF); mizoribine (MZ); leflunomide (LEF); adrenocortical steroids (also known as adrenocortical hormones, corticosteroids, corticoids) such as prednisolone and methylprednisolone; sirolimus (also known as rapamycin); deoxyspergualin (DSG); and FTY720 (also called Fingolimod, chemical name: 2-amino-2-[2-(4-octylphenyl)ethyl]-1,3-propanediol hydrochloride). Also being clinically developed as immunosuppressive agents are agents that block CTLA-4 and CD28, which are molecules responsible for transducing costimulatory signals necessary for the activation of T cells (costimulatory signal transduction molecules); such agents include CTLA-4 drugs that use the soluble region of CTLA-4 and the gene encoding it.

General immunosuppressives, such as corticosteroids and cytokine antagonists, can elicit undesirable side effects including toxicity and reduced resistance to infection. Thus, alternative, and perhaps more specific, methods of treating autoimmunity and promoting graft survival are needed.

One molecule that has been thought to induce immunosuppression and promote graft survival is OX-2, or CD200. CD200 is expressed on the surface of B cells, some T cells, dendritic cells and other cells and possesses a high degree of homology to molecules of the immunoglobulin gene family. CD200 has been implicated in immune suppression, and it has been shown, for example, that CD200-expressing cells can inhibit the stimulation of Th1 cytokine production (Gorczynski et al., 1998 *Transplantation* 65:1106-1114). In addition, soluble CD200 has been shown to promote allo- and xenograft survival in mice and to decrease antibody response to sheep erythrocytes in mice (Gorczynski et al. 1999 *J. Immunol.* 163: 1654-1660). Further, CD200-knockout mice exhibit a decreased ability to down-regulate APC activation compared to wildtype mice, resulting in chronic inflammation in the central nervous system, a hyper-inflammatory response, and increased susceptibility to certain experimental autoimmune disorders (Hoek et al. 2000 *Science* 290: 1768-1771). The immunosuppressive effects of CD200 are believed to be the result of CD200 binding to its receptor, CD200R (Hoek et al. supra; Gorczynski et al. 2000 *J. Immunol.* 165: 4854), which is expressed on cells of monocyte/myeloid lineage and of T-lymphocyte origin.

While CD200 has been shown to elicit immunosuppressive effects, an antibody to CD200 has been shown to inhibit these immunosuppressive effects. For example, an anti-CD200 antibody (including an anti-CD200 F(ab')$_2$ fragment) abolished the CD200Fc-induced prolonged survival of rat islet xenografts in mice (Gorczynski et al. 2002 *Transplantation*. 73: 1948-53).

Contrary to the published reports discussed above, the present disclosure demonstrates that an anti-CD200 antibody and compositions comprising an anti-CD200 antibody promote graft survival. Accordingly, the present disclosure provides novel compositions and methods for inhibiting graft rejection and promoting graft survival.

SUMMARY

The present disclosure relates to the discovery that administration of an anti-CD200 antibody can inhibit immunological responses to an immune challenge, such as a grafted tissue or organ. Accordingly, it is an objective of the present disclosure to provide methods and pharmaceutical agents to suppress, treat, or prevent immunological responses, where in particular embodiments the immunological response accompanies the transplantation of a cell, tissue, or organ (e.g., graft rejection or graft versus host disease). Also, the immunological response may occur at a later time, e.g., during a rejection episode in the recipient of a transplanted cell, tissue or organ. The methods and agents of the disclosure may employ medical and pharmaceutical techniques (for example, pharmaceutical agents such as low-molecular weight compounds and antibodies) to modulate the biological function of CD200 or to modulate the activity of cells expressing CD200.

In certain aspects, the present disclosure relates to agents that specifically bind to CD200. CD200-binding agents include but are not limited to polypeptides, small molecules, organometallic compounds, immunomodulatory agents, antibodies, antigen-binding fragments of antibodies, prodrugs, and/or peptidomimetic compounds. The agent may or may not inhibit or reduce the interaction of CD200 with a CD200 receptor (CD200R).

In certain embodiments, an agent that specifically binds CD200 is an anti-CD200 antibody. Antibodies, as referred to herein, include but are not limited to monoclonal and polyclonal antibodies, engineered antibodies (including chimeric, single chain, CDR-grafted, humanized, fully human antibodies, de-immunized antibodies, and artificially selected antibodies), and synthetic or semi-synthetic antibodies. Antibodies of the present disclosure also include other variations and derivatives of an antibody (e.g., an isolated or recombinant antibody, antibody conjugate or antibody derivative) and antibodies that are murine, human, chimeric, humanized, primatized, etc. Antibodies of the present disclosure also include antigen-binding fragments, such as, for example, Fab, Fab', F(ab')$_2$, F(ab')$_3$, Fd, Fv, domain antibodies (dAb), other monovalent and divalent fragments, complementarity determining region (CDR) fragments, single-chain antibodies (e.g., scFv, scFab, scFabAC), diabodies, triabodies, minibodies, nanobodies, and polypeptides that contain at least a portion of an antibody that is sufficient to confer specific binding to CD200, and fusions and derivatives of the foregoing. In certain aspects, the present disclosure relates to chimeric, humanized, human and de-immunized anti-CD200 antibodies and antigen-binding fragments thereof. In further embodiments, the disclosure relates to antibodies comprising the IgG1, IgG2, IgG3, IgG4, IgM, IgA1, IgA2, IgA, IgD, and/or IgE frameworks.

In particular embodiments, the agent that specifically binds CD200 may be an agent that inhibits the interaction between CD200 and a CD200R. In some embodiments, an agent that inhibits the interaction between CD200 and a CD200R is an anti-CD200 antibody or antigen-binding fragment thereof. In some embodiments, the antibody or antigen-binding fragment exhibits effector function, whereas in other embodiments, the antibody or antigen-binding fragment exhibits reduced or no effector function. In other embodiments, the agent is a soluble CD200R or a nonagonistic soluble CD200.

Accordingly, in certain embodiments, the present disclosure relates to a method of inhibiting an immune response in a subject in need thereof, wherein the method comprises administering to the subject an effective amount of i) an agent which inhibits interaction between CD200 and CD200R and ii) an immunosuppressive or immunomodulatory agent or drug. In certain embodiments, the immune response is a humoral response. In further embodiments, the immune response is an antibody mediated response. The agent may exhibit effector function in some embodiments. Alternatively, the agent may exhibit reduced or no effector function. In particular embodiments, the agent is an anti-CD200 antibody or antigen-binding fragment thereof. In other embodiments, the agent is a soluble CD200R or a nonagonistic soluble CD200. In any of the above embodiments, the immunomodulatory or immunosuppressive drug may target T cells, B cells, both T and B cells, or another immune cell. In particular embodiments, the immunosuppressive drug is cyclosporine A or rapamycin.

In certain embodiments, the present disclosure provides a method of inhibiting a humoral immune response in a subject in need thereof, wherein the method comprises administering to the subject an effective amount of an anti-CD200 antibody or antigen-binding fragment thereof. In such embodiments, the anti-CD200 antibody or antigen-binding fragment thereof is selected from the group consisting of a human antibody or antigen-binding fragment, a humanized antibody or antigen-binding fragment, a primatized antibody or antigen-binding fragment, a chimeric antibody or antigen-binding fragment, a murine antibody or antigen-binding fragment, and a de-immunized antibody or antigen-binding fragment. The antigen-binding fragment may further be selected from the group consisting of single-chain antibody, Fab, Fab', F(ab')$_2$, F(ab')$_3$, Fd, Fv, domain antibody, and any fragment of an anti-CD200 immunoglobulin that confers specific binding to CD200. Any of the aforementioned antibodies or antigen-binding fragments may be conjugated to a molecule, such as a polymer or a polypeptide. The polymer may be, in some embodiments, poly(ethylene) glycol (PEG).

The inhibition of a humoral immune response may include, for example, an inhibition of any one or more of the following responses: a) antigen presentation by APC; b) activation of helper (CD4+) T cells; c) proliferation of helper (CD4+) T-cells; d) differentiation of B cells; e) proliferation of B cells; and f) B-cell production of antibodies. In certain embodiments, the method results in a decrease in the production of B-cell antibodies, wherein the antibodies are selected from IgG, IgM, IgG1, and IgG2a immunoglobulins.

In certain embodiments, the present disclosure provides a method of inhibiting a humoral immune response in a subject in need thereof, wherein the method comprises administering to the subject an effective amount of an anti-CD200 antibody or antigen-binding fragment thereof and further comprises administering to the subject an immunomodulatory or immunosuppressive agent. The immunomodulatory or immunosuppressive agent may target T cells, B cells, both T and B cells, or another immune cell. In certain embodiments, the immunomodulatory or immunosuppressive agent is a calcineurin inhibitor. In further embodiments, the calcineurin inhibitor is selected from tacrolimus and cyclosporine A.

In other embodiments, the immunomodulatory or immunosuppressive agent administered in combination with an anti-CD200 antibody or fragment thereof is selected from the group consisting of adriamycin, azathiopurine, busulfan, cyclophosphamide, cyclosporine A, Cytoxan, fludarabine, 5-fluorouracil, methotrexate, mycophenolate mofetil, 6-mercaptopurine, a corticosteroid, a nonsteroidal anti-inflammatory, sirolimus (rapamycin), and tacrolimus (FK-506). In alternative embodiments, the immunomodulatory or immunosuppressive agent is an antibody selected from the group consisting of muromonab-CD3, alemtuzumab, basiliximab, daclizumab, rituximab, anti-thymocyte globulin and IVIg. In certain embodiments, the immunomodulatory or immunosuppressive agent is not an inhibitor of the complement pathway (e.g., the agent is not an antibody (such as an anti-C5 antibody) or molecule that inhibits complement activity).

In certain embodiments of the methods described herein, the subject in need of humoral immunosuppression is a mammal, and in further embodiments the subject is a human subject. In particular embodiments, the subject has received or will receive a transplant.

In certain embodiments, the disclosure relates to a method of decreasing the number of circulating B cells in a subject in need thereof, wherein the method comprises administering to the subject (a) an anti-CD200 antibody or antigen-binding fragment thereof and (b) an immunomodulatory or immunosuppressive agent. In additional embodiments, the disclosure relates to a method of decreasing the number of activated CD200-positive T cells in a subject in need thereof, wherein the method comprises administering to the subject (a) an anti-CD200 antibody or antigen-binding fragment thereof and (b) an immunomodulatory or immunosuppressive agent. Further, some embodiments relate to a method of inhibiting B cell activation in a subject in need thereof, wherein the method comprises administering to the subject (a) an anti-CD200 antibody or antigen-binding fragment thereof and (b) an immunomodulatory or immunosuppressive agent. For example, the anti-CD200 antibody or antigen-binding fragment and the agent may be administered in an amount sufficient to decrease the amount of circulating immunoglobulin in the subject. In any of the above embodiments, the subject may be a mammal, such as a primate or human subject. Optionally, the subject has received or will receive a cell, tissue, or organ transplant.

In certain aspects, the present disclosure relates to a method of inhibiting graft rejection in a graft recipient in need thereof, wherein the method comprises administering to the recipient therapeutically effective amounts of (a) an anti- CD200 antibody or antigen-binding fragment thereof and (b) an immunomodulatory or immunosuppressive agent. A therapeutically effective amount may refer to an amount of the combination of a) an anti-CD200 antibody and b) an immunomodulatory or immunosuppressive agent such that the combination is effective in inhibiting graft rejection. In certain embodiments, the anti-CD200 antibody or antigen-binding fragment thereof is selected from the group consisting of a human antibody or antigen-binding fragment thereof, a humanized antibody or antigen-binding fragment thereof, a primatized antibody or antigen-binding fragment thereof, a chimeric antibody or antigen-binding fragment thereof, a murine antibody or antigen-binding fragment thereof, and a de-immunized antibody or antigen-binding fragment thereof. The antigen-binding fragment may further be selected from the group consisting of single-chain antibody, Fab, Fab', $F(ab')_2$, $F(ab')_3$, Fd, Fv, domain antibody, and any fragment of an anti-CD200 immunoglobulin that confers specific binding to CD200. Any of the aforementioned antibodies or antigen-binding fragments may be conjugated to a molecule, such as a polymer or a polypeptide. The polymer may be, in some embodiments, poly(ethylene) glycol (PEG).

In certain embodiments of inhibiting graft rejection, the anti-CD200 antibody or antigen-binding fragment thereof and the immunomodulatory or immunosuppressive agent are administered prior to a transplant. In other embodiments, the antibody and agent are administered at the time of transplantation. In other embodiments, the antibody and agent are administered post-transplant. In some embodiments, the graft rejection is an acute humoral rejection of a grafted cell, tissue, or organ. In other embodiments, the graft rejection is a chronic humoral rejection of a grafted cell, tissue, or organ.

In certain embodiments of the present disclosure, the graft recipient is a recipient of a hematopoietic cell or bone marrow transplant, an allogeneic transplant of pancreatic islet cells, or a solid organ transplant selected from the group consisting of a heart transplant, a kidney-pancreas transplant, a kidney transplant, a liver transplant, a lung transplant, and a pancreas transplant. Additional examples of grafts include but are not limited to allotransplanted cells, tissues, or organs such as vascular tissue, eye, cornea, lens, skin, bone marrow, muscle, connective tissue, gastrointestinal tissue, nervous tissue, bone, stem cells, cartilage, hepatocytes, or hematopoietic cells.

In some embodiments of inhibiting graft rejection, the immunomodulatory or immunosuppressive agent is an agent that targets T cells or B cells or both T cells and B cells. In certain embodiments, the agent does not target the complement pathway and/or does not inhibit complement-mediated immune response. In particular embodiments, the immunomodulatory or immunosuppressive agent is a calcineurin inhibitor. In further embodiments, the calcineurin inhibitor is selected from tacrolimus and cyclosporine A.

In additional embodiments of inhibiting graft rejection, the immunomodulatory or immunosuppressive agent is selected from the group consisting of adriamycin, azathiopurine, busulfan, cyclophosphamide, cyclosporine A, fludarabine, 5-fluorouracil, methotrexate, mycophenolate mofetil, 6-mercaptopurine, a corticosteroid, a nonsteroidal anti-inflammatory, sirolimus (rapamycin), and tacrolimus (FK-506). In alternative embodiments, the immunomodulatory or immunosuppressive agent is an antibody selected from the group consisting of muromonab-CD3, alemtuzumab, basiliximab, daclizumab, rituximab, anti-thymocyte globulin and IVIg:

In certain embodiments, a method comprising administering an anti-CD200 antibody and an immunomodulatory or immunosuppressive agent results in an inhibition of a humoral immune response in the graft recipient. For example, in certain embodiments, the method results in a decrease in the production of anti-donor antibodies. The anti-donor antibodies may be selected from IgG, IgM, IgG1, and IgG2a immunoglobulins. In some embodiments, the graft recipient exhibits or suffers from an acute graft rejection of cell, tissue or organ allo- or xenotransplant. In other embodiments, the graft recipient exhibits or suffers from a chronic graft rejection of cell, tissue or organ allo- or xenotransplant.

In other embodiments, a method comprising administering an anti-CD200 antibody and an immunomodulatory or immunosuppressive agent results in an inhibition of a cellular immune response in the graft recipient. For example, in certain embodiments, the method results in a decrease in the production of recipient CD4+ and CD8+ T cells in lymphoid tissues. In some embodiments, the graft recipient exhibits or suffers from an acute graft rejection of cell, tissue or organ allo- or xenotransplant. In other embodiments, the graft recipient exhibits or suffers from a chronic graft rejection of cell, tissue or organ allo- or xenotransplant.

In certain aspects, the present disclosure relates to a method of treating or preventing graft rejection in a graft recipient in need thereof, wherein the method comprises administering to the recipient therapeutically effective amounts of (a) an anti-CD200 antibody or antigen-binding fragment thereof and (b) an immunomodulatory or immunosuppressive agent. In further embodiments, the present disclosure relates to a method of promoting or prolonging graft survival in a graft recipient, wherein the method comprises administering to the graft recipient therapeutically effective amounts of (a) an anti-CD200 antibody or antigen-binding fragment thereof and (b) an immunomodulatory or immunosuppressive agent. The anti-CD200 antibody or antigen-binding fragment thereof may be selected from among a human antibody or antigen-binding fragment thereof, a humanized antibody or antigen-binding fragment thereof, a primatized antibody or antigen-binding fragment thereof, a chimeric antibody or antigen-binding fragment thereof, a murine antibody or antigen-binding fragment thereof, and a de-immunized antibody or antigen-binding fragment thereof. The antigen-binding fragment may further be selected from among a single-chain antibody, Fab, Fab', $F(ab')_2$, $F(ab')_3$, Fd, Fv, domain antibody, and any fragment of an anti-CD200 immunoglobulin that confers specific binding to CD200.

In further embodiments, a method of prolonging or promoting graft survival of the present disclosure increases graft survival in the recipient by at least about 15%, by at least about 20%, by at least about 25%, by at least about 30%, by at least about 40%, or by at least about 50%, compared to the graft survival observed in a control recipient. A control recipient may be, for example, a graft recipient that does not receive a therapy post-transplant or that receives a monotherapy following transplant.

In certain embodiments, a method of promoting graft survival promotes long-term graft survival, wherein the long-term graft survival is selected from among: at least about 6 months post transplant, at least about 1 year post transplant; at least about 5 years post transplant; at least about 7.5 years post-transplant; and at least about 10 years post-transplant. In certain embodiments, the therapies described herein promote accommodation of the graft and the graft survives for the remaining life-time of the recipient.

In any of the embodiments of the present disclosure, the graft recipient may be a primate graft recipient, such as a non-human primate graft recipient. In further embodiments, the graft recipient is a human graft recipient.

In any of the embodiments described herein, an anti-CD200 antibody or antigen-binding fragment thereof may be administered systemically to a subject or to a graft recipient. Alternatively, the antibody or antigen-binding fragment thereof may be administered locally to the subject or graft recipient.

In embodiments comprising a combination of an anti-CD200 antibody or antigen-binding fragment thereof and an immunomodulatory or immunosuppressive agent, the anti-CD200 antibody or antigen-binding fragment thereof and immunomodulatory or immunosuppressive agent are administered sequentially. In other embodiments, the antibody or fragment thereof and agent are administered simultaneously.

The application contemplates combinations of any of the foregoing aspects and embodiments. All references and documents cited herein are incorporated in their entirety.

BRIEF DESCRIPTION OF THE FIGURES

FIGS. 1A-1F depict the amino acid sequences and nucleotide sequences for the heavy and light chains of antibody chC2aB7-hG1 (SEQ ID NOS: 1, 2, 3, 4, 5, and 6). FIG. 1C shows SEQ ID NO: 3 (nucleic acid sequence) and SEQ ID NO: 1 (amino acid sequence). SEQ ID NO: 3 as shown in the schematic is contiguous but is depicted with a corresponding nucleotide sequence that includes introns. FIG. 1F shows SEQ ID NO: 6 (nucleic acid sequence) and SEQ ID NO: 4 (amino acid sequence). SEQ ID NO:5 (shown in FIG. 1E) encodes SEQ ID NO:4 (shown in FIG. 1D).

Figure 2F:
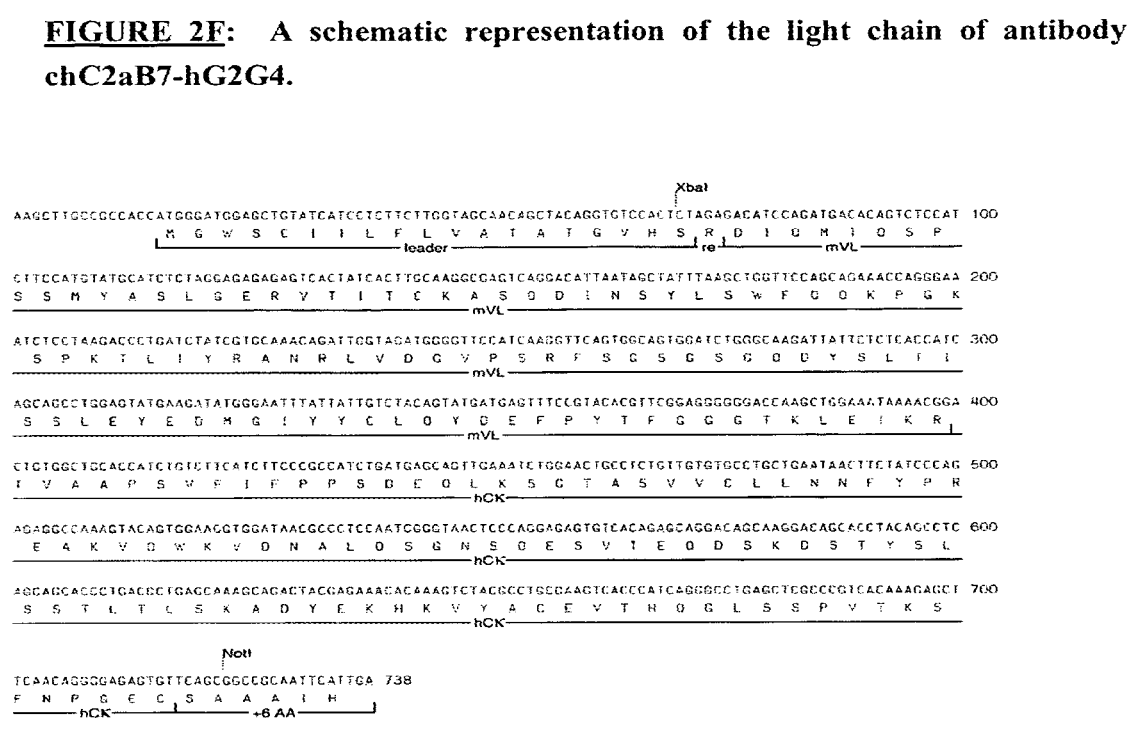

FIGS. 2A-2F depict the amino acid sequences and nucleotide sequences for the heavy and light chains of antibody chC2aB7-hG2G4 (SEQ ID NOS: 7, 8, 9, 10, 11, 12, 13, and 14). FIG. 2C shows SEQ ID NO: 10 (nucleic acid sequence) and SEQ ID NO: 9 (amino acid sequence). SEQ ID NO: 9 corresponds to amino acids 1-337 of SEQ ID NO: 7. As shown in the schematic, SEQ ID NO: 10 is contiguous but is depicted with a corresponding nucleotide sequence that includes introns. FIG. 2F shows SEQ ID NO: 14 (nucleic acid sequence) and SEQ ID NO: 13 (amino acid sequence). SEQ ID NO:12 (shown in FIG. 2E) encodes SEQ ID NO:11 (shown in FIG. 2D).

FIGS. 3A-3F depict the amino acid sequences and nucleotide sequences for the heavy and light chains of antibody hB7V3V2-hG1 (SEQ ID NOS: 15, 16, 17, 18, 19, and 20). FIG. 3C shows SEQ ID NO: 17 (nucleic acid sequence) and SEQ ID NO: 15 (amino acid sequence). FIG. 3F shows SEQ ID NO: 20 (nucleic acid sequence) and SEQ ID NO: 18 (amino acid sequence). SEQ ID NO:19 (shown in FIG. 3E) encodes SEQ ID NO:18 (shown in FIG. 3D).

Figure 4C:
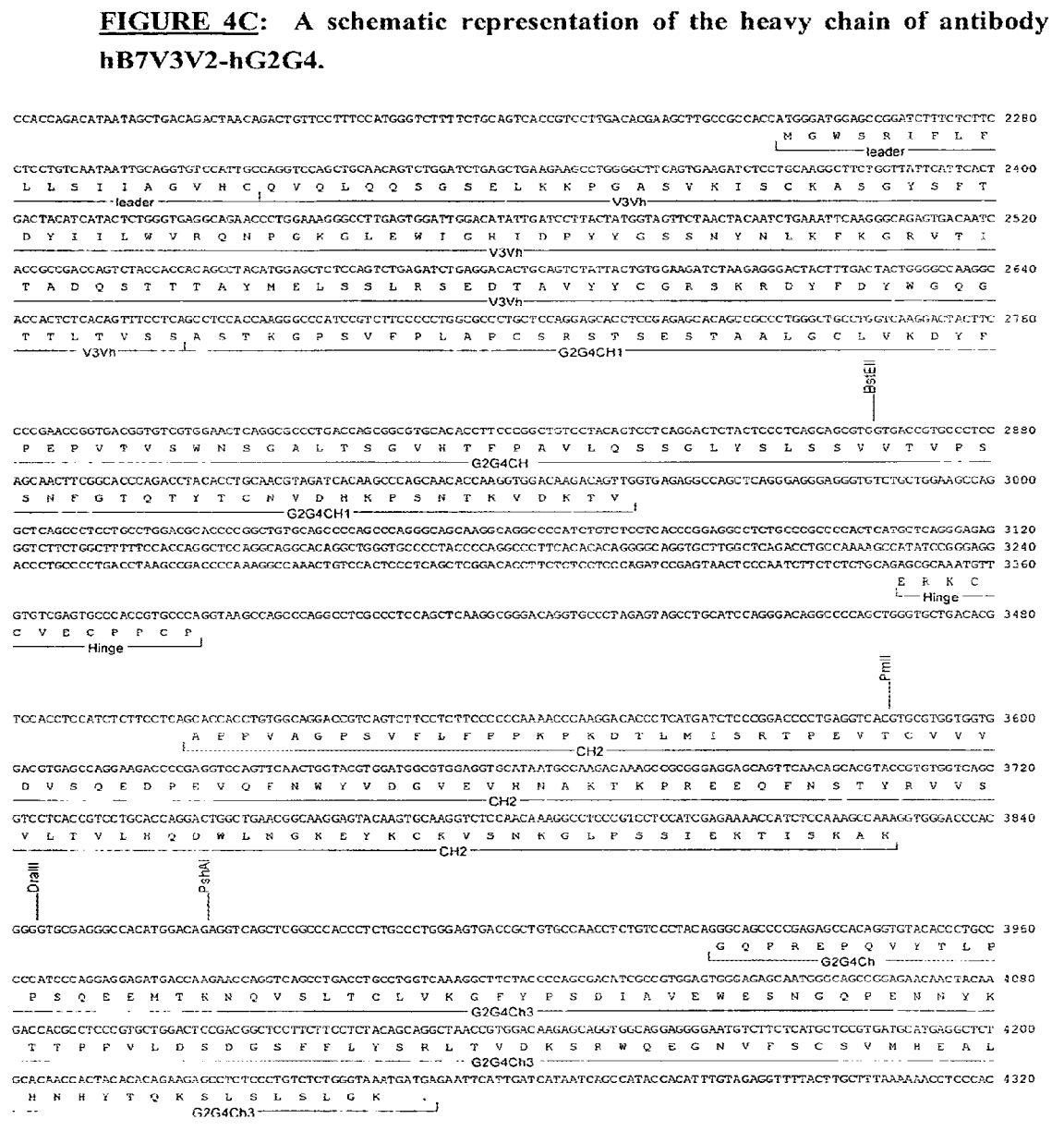

FIGS. 4A-4F depict the amino acid sequences and nucleotide sequences for the heavy and light chains of antibody hB7V3V2-hG2G4 (SEQ ID NOS: 21, 22, 23, 24, 25, and 26). FIG. 4C shows SEQ ID NO: 23 (nucleic acid sequence) and SEQ ID NO: 21 (amino acid sequence). SEQ ID NO: 23 as shown in the schematic is contiguous but is depicted with a corresponding nucleotide sequence that includes introns. FIG. 4F shows SEQ ID NO: 26 (nucleic acid sequence) and SEQ ID NO: 24 (amino acid sequence). SEQ ID NO:25 (shown in FIG. 4E) encodes SEQ ID NO:24 (shown in FIG. 4D).

FIG. 6 demonstrates the effects of anti-CD200 antibodies on ADCC of activated T-cells. CD3+ human T cells were stimulated with 10 μg/mL immobilized (plate-coated) mOKT3 for 72 hrs. Activated T cells were then chromated for use as targets and incubated with purified autologous CD56+ (NK) cells as effector cells. Cells were coincubated for 4 hours at 37° C. at 25:1 (A) or 10:1 (B) effector:target cell ratios in the presence or absence of a humanized anti-CD200 antibody capable of mediating effector function (V3V2-G1) or engineered to lack effector function (V3V2-G2G4). Data are represented as percent specific lysis. The anti-CD200 antibody with effector function efficiently mediated ADCC of the activated T-cell targets, whereas the anti-CD200 antibody with no effector function failed to mediate ADCC.

FIG. 7A provides the relative levels of circulating anti-donor IgG antibodies in heart allograft recipients following various immunomodulatory treatments. FIG. 7B provides the relative levels of circulating anti-donor IgM antibodies in heart allograft recipients following various immunomodulatory treatments. MFI is mean fluorescent intensity.

FIG. 10 shows the sequences of the heavy chains of OX90NE (SEQ ID NO:27) and OX90mG2a (SEQ ID NO:28). The four amino acid differences between the two molecules are highlighted in bold (amino acid residues 236, 319, 321 and 323). The variable portion of each encompasses amino acid residues 1-118. The constant region for each comprises amino acid residues 119-448.

DETAILED DESCRIPTION

I. Overview

A. Rejection of Transplants or Grafts

Figure 5:
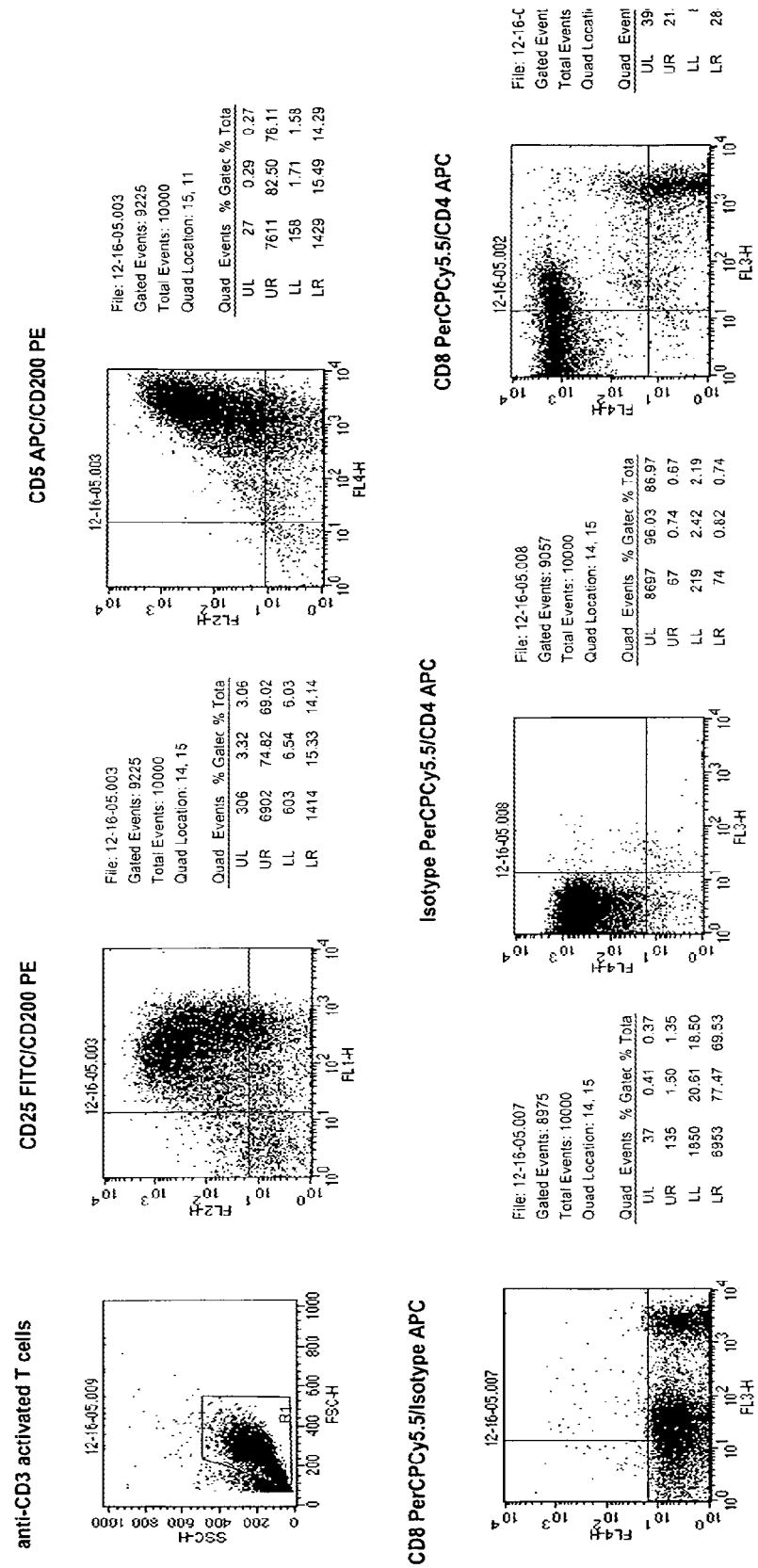
FIG. 5 shows flow cytometric analysis of CD200 expression on activated T-cells. CD3+ human cells were activated with mOKT3, harvested, washed and subjected to staining with the indicated fluorochrome-conjugated antibodies specific for human CD25, CD200, CD5, CD4 and CD8. Cells were washed and analyzed for immunofluorescence on a FACSCalibur flow cytometer using CellQuest software. Activation of human T cells results in a dramatic upregulation of CD200 expression.

Hyperacute rejection occurs within minutes to hours after transplant and is due to preformed antibodies to the transplanted tissue antigens. It is characterized by hemorrhage and thrombotic occlusion of the graft vasculature. The binding of antibody to endothelium activates complement, and antibody and complement induce a number of changes in the graft endothelium that promote intravascular thrombosis and lead to vascular occlusion, resulting in irreversible ischemic damage of the grafted organ (Abbas et al., 2000 *Cellular and Molecular Immunology* (4th edition), p. 363-383 (W.B. Saunders Company, New York)). Hyperacute rejection is often mediated by preexisting IgM alloantibodies, e.g., antibodies directed against the ABO blood group antigens expressed on red blood cells. This type of rejection, mediated by natural antibodies, is the main reason for rejection of xenotransplants. Hyperacute rejection due to natural IgM antibodies is no longer a major problem with allografts because allografts are usually selected to match the donor and recipient ABO type. Hyperacute rejection of an ABO matched allograft may still occur and is usually mediated by IgG antibodies directed against protein alloantigens, such as foreign MHC molecules, or against less well defined alloantigens expressed on vascular endothelial cells. Such IgG antibodies may arise as a result of prior exposure to alloantigens through blood transfusion, prior transplantation, or multiple pregnancies, for example.

Acute rejection is a process of vascular and parenchymal injury mediated by T cells, macrophages, and antibodies that usually begins after the first week of transplantation (Abbas et al., supra). T lymphocytes play a central role in acute rejection by responding to alloantigens, including MHC molecules, present on vascular endothelial and parenchymal cells. The activated T cells cause direct lysis of graft cells or produce cytokines that recruit and activate inflammatory cells, which cause necrosis. Both $CD4^+$ and $CD8^+$ T cells may contribute to acute rejection. The destruction of allogeneic cells in a graft is highly specific and is a hallmark of $CD8^+$ cytotoxic T lymphocyte killing. $CD4^+$ T cells may be important in mediating acute graft rejection by secreting cytokines and inducing delayed-type hypersensitivity-like reactions in grafts; some evidence indicates that $CD4^+$ T cells are sufficient to mediate acute rejection (Abbas et al., supra). Antibodies can also mediate acute rejection after a graft recipient mounts a humoral immune response to vessel wall antigens when the antibodies that are produced bind to the vessel wall and activate complement (Abbas et al., supra).

Chronic rejection is characterized by fibrosis with loss of normal organ structures occurring over a prolonged period. The pathogenesis of chronic rejection is less well understood than the pathogenesis of acute rejection. Graft arterial occlusion may occur as a result of the proliferation of intimal smooth muscle cells (Abbas et al., supra). This process is called accelerated or graft arteriosclerosis and can develop in any vascularized organ transplant within 6 months to a year after transplantation.

Allografts are rejected in part by the activation of T cells. The transplant recipient mounts a rejection response following $CD4^+$ T cell recognition of foreign antigens in the allograft. These antigens are encoded by the major histocompatibility complex (MHC) of which there are both Class I and Class II MHC molecules. In humans the class I MHC molecules are HLA-A, HLA-B, and HLA-C. The class II MHC molecules in humans are called HLA-DR, HLA-DQ and HLA-DP. In mice the class I MHC molecules are H-2K, H-2D and H-2L and the class II MHC molecules are I-A and I-E. When $CD4^+$ T cells bind processed or intact foreign MHC antigens they are activated and undergo clonal proliferation. The activated T cells secrete cytokines which aid in activating monocytes/macrophages, B cells and cytotoxic $CD8^+$ T cells. The activated monocytes/macrophages release agents which result in tissue damage, the B cells produce alloantibodies which lead to complement-mediated graft destruction, and the $CD8^+$ T cells kill graft cells in an antigen-specific manner through induction of apoptosis and cell lysis.

The importance of humoral immunity in graft rejection was initially thought to be limited to hyperacute rejection, in which the graft recipient possesses anti-donor HLA antibodies prior to transplantation, resulting in rapid destruction of the graft in the absence of an effective therapeutic regimen of antibody suppression. Recently, it has become evident that humoral immunity is also an important factor mediating both acute and chronic rejection. For example, clinical observations demonstrated that graft survival in patients capable of developing class I or class II anti-HLA alloantibodies (also referred to as "anti-MHC alloantibodies") was reduced compared to graft survival in patients that could not develop such antibodies. Clinical and experimental data also indicate that other donor-specific alloantibodies and autoantibodies are critical mediators of rejection. For a review of the evidence supporting a role for donor-specific antibodies in allograft rejection, see Rifle et al., *Transplantation,* 2005 79:S14-S18.

B. Immunosuppressive Agents

For a transplant to be successful, several modes of rejection must be overcome. Therefore multiple approaches are utilized in preventing or inhibiting rejection. Inhibiting graft rejection may require administration of immunosuppressants, often of several types, to prevent or inhibit the various modes of attack—e.g., inhibition of T-cell attack, inhibition of antibody responses, and inhibition of cytokine and complement effects. Prescreening of donors to match them with recipients is also a major factor in preventing rejection, especially in preventing hyperacute rejection. Immunoadsorption of anti-HLA antibodies prior to grafting may reduce hyperacute rejection. Prior to transplantation, the recipient or host may be administered anti-T cell reagents, e.g., the monoclonal antibody OKT3, Anti-Thymocyte Globulin (ATG), cyclosporine A, or tacrolimus (FK 506). Additionally, glucocorticoids and/or azathioprine (or other purine analogs) may be administered to the host prior to transplant. Drugs used to aid in preventing or inhibiting transplant rejection include, but are not limited to, ATG or ALG, OKT3, daclizumab, basiliximab, corticosteroids, 15-deoxyspergual in, LF15-0195, cyclosporine, tacrolimus, purine analogs such as azathioprine, methotrexate, mycophenolate mofetil, 6-mercaptopurine, bredinin, brequinar, leflunamide, cyclophosphamide, sirolimus, anti-CD4 monoclonal antibodies, CTLA4-Ig, rituxan, anti-CD154 monoclonal antibodies, anti-LFA1 monoclonal antibodies, anti-LFA-3 monoclonal antibodies, anti-CD2 monoclonal antibodies, and anti-CD45.

The numerous drugs utilized to delay graft rejection (i.e., to prolong graft survival) work in a variety of ways. See Stepkowski (2000). *Exp. Rev. Mol. Med.* 21 June, world wide web at expertreviews.org/00001769h.htm for a review of the mechanisms of action of several immunosuppressive drugs.

Cyclosporine A is one of the most widely used immunosuppressive drugs for inhibiting graft rejection. It is an inhibitor of interleukin-2 or IL-2 (it prevents mRNA transcription of interleukin-2). More directly, cyclosporine inhibits calcineurin activation that normally occurs upon T cell receptor stimulation. Calcineurin dephosphorylates NFAT (nuclear factor of activated T cells), thereby enabling NFAT to enter the nucleus and bind to interleukin-2 promoter. By blocking this process, cyclosporine A inhibits the activation of the $CD4^+$ T cells and the resulting cascade of events which would otherwise occur. Tacrolimus is another immunosuppressant that acts by inhibiting the production of interleukin-2 via calcineurin inhibition.

Rapamycin (Sirolimus), SDZ RAD, and interleukin-2 receptor blockers are drugs that inhibit the action of interleukin-2 and therefore prevent the cascade of events described above.

Inhibitors of purine or pyrimidine biosynthesis are also used to inhibit graft rejection. These inhibitors prevent DNA synthesis and thereby inhibit cell division including T cell proliferation. The result is the inhibition of T cell activity by preventing the formation of new T cells. Inhibitors of purine synthesis include azathioprine, methotrexate, mycophenolate mofetil (MMF) and mizoribine (bredinin). Inhibitors of pyrimidine synthesis include brequinar sodium and leflunomide. Cyclophosphamide is an inhibitor of both purine and pyrimidine synthesis.

Yet another method for inhibiting T cell activation is to treat the recipient with antibodies to T cells. OKT3 is a murine monoclonal antibody against CD3 which is part of the T cell receptor. This antibody initially activates T cells through the T cell receptor, then induces apoptosis of the activated T cell.

Numerous other drugs and methods for delaying allotransplant rejection are known to and used by persons of skill in the art. One approach is to deplete T cells, e.g., by irradiation. Depletion of T cells has often been used in bone marrow transplants, especially if there is a partial mismatch of major HLA. Administration to the recipient of an inhibitor (blocker) of the CD40 ligand-CD40 interaction and/or a blocker of the CD28-B7 interaction has also been used (U.S. Pat. No. 6,280, 957). Published PCT patent application WO 01/37860 discloses the administration of an anti-CD3 monoclonal antibody and IL-5 to inhibit the Th1 immune response. Published PCT patent application WO 00/27421 teaches a method for prophylaxis or treatment of corneal transplant rejection by administering a tumor necrosis factor-α antagonist. Glotz et al. (2002 *Am. J. Transplant.* 2:758-760) show that administration of intravenous immunoglobulins (IVIg) can induce a profound and sustained decrease in the titers of anti-HLA antibodies thereby allowing survival of an HLA-mismatched organ. Similar protocols have included plasma exchanges (Taube et al., 1984 *Lancet* 1:824-828) or immunoadsorption techniques coupled to immunosuppressive agents (Hiesse et al., 1992 *Nephrol. Dial. Transplant.* 7:944-951) or a combination of these methods (Montgomery et al., 2000 *Transplantation* 70:887-895). Changelian et al. (2003 *Science* 302:875-878) teach a model in which immunosuppression is caused by an oral inhibitor of Janus kinase 3 (JAK3), which is an enzyme necessary for the proper signaling of cytokine receptors which use the common gamma chain (γc) (Interleukins-2, -4, -7, -9, -15, -21), the result being an inhibition of T cell activation. Antisense nucleic acids against ICAM-1 have been used alone or in combination with a monoclonal antibody specific for leukocyte-function associated antigen 1 (LFA-1) in a study of heart allograft transplantation (Stepkowski, supra). Similarly, an anti-ICAM-1 antibody has been used in combination with anti-LFA-1 antibody to treat heart allografts (Stepkowski, supra). Antisense oligonucleotides have additionally been used in conjunction with cyclosporine in rat heart or kidney allograft models, resulting in a synergistic effect to prolong the survival of the grafts (Stepkowski, supra). Chronic transplant rejection has been treated by administering an antagonist of TGF-β, which is a cytokine involved in differentiation, proliferation, and apoptosis (U.S. Patent Application Publication US 2003/0180301).

C. CD200 and Immunosuppression

Another mechanism that has been thought to be involved in suppressing the immune response involves the molecule CD200. CD200 is a highly conserved type I transmembrane glycoprotein expressed on various cell types including cells of the immune system (e.g., T-cells, B-cells, and dendritic cells (Barclay et al., 2002 *TRENDS Immunol.* 23:285-290)) as well as certain cancer cells. The protein interacts with its receptor CD200R on myeloid cells and sub-populations of T cells (Wright et al. 2003 *J. Immunol.* 171: 3034-3046 and Wright et al., 2000 *Immunity* 13:233-242); it has been thought that the CD200:CD200R interaction delivers an immunomodulatory signal to cells and induces immunosuppression including apoptosis-associated immune tolerance (Rosenblum et al. 2004 *Blood* 103: 2691-2698).

Previous studies, especially numerous articles by Gorczynski et al., have indicated that CD200 is immunosuppressive. For example, Gorczynski et al. (*Clin. Immunol.* 104: 256-264 (2002)) teach that in a mouse collagen-induced arthritis (CIA) model, treatment with soluble CD200 (CD200Fc) ameliorates CIA. In the transplant setting, Gorczynski et al. (*Eur. J. Immunol.* 31: 2331-2337 (2001)) report that soluble CD200 protein promotes allograft survival while anti-CD200 antibodies prevent immunosuppression and result in shortened times of allograft survival.

In contrast to previous reports, the present disclosure demonstrates that administration of an anti-CD200 antibody promotes graft survival. While not wishing to be bound by any particular mechanism(s) of action, prolonged survival of a graft may be due to the killing or inactivation of T-cells and/or the inhibition of B-cell activity (e.g., inhibition of a humoral response against the graft). For example, CD200 is highly expressed on activated T and B cells, compared with lower levels of expression on resting cells. Accordingly, administration of an anti-CD200 antibody could result in activated T cells and B cells being coated with antibody, rendering the cells susceptible to antibody-mediated cellular cytotoxicity (ADCC), complement-dependent cytotoxicity (CDC), and/or other effector functions such as apoptosis. One possible result of antibody administration could be, therefore, killing of activated immune cells and a suppression of the immune response. However, as described below, this effect is seen not only with antibodies which have effector function but also with antibodies lacking effector function. Therefore, it appears that if the killing of B and/or T cells is involved, effector function is only part of the story. As shown below, inhibiting the interaction of CD200 with the CD200 receptor (CD200R), whether using an antibody with effector function or without effector function, can suppress the immune response and promote graft survival as well as be used in ameliorating autoimmune disease. Again, without wishing to be bound by any particular mechanism of action, the inhibition of binding of CD200 to CD200R seems to be the important first step.

Accordingly, anti-CD200 antibody administration may prolong graft survival via one or more of the following mechanisms: (i) inhibition of antibody production (e.g., via a reduction in the number of B cells, such as by killing of B cells); (ii) alteration of cytokine production (e.g., production of TNF-α and IL-12) by, for example, a reduction in the number of T cells (such as by T cell killing, for example); (iii) induction of an intravenous immunoglobulin (IVIg) effect (e.g., soluble CD200 shed from the cell surface may bind to the anti-CD200 antibody to form a complex); (iv) interference with antigen presentation, resulting in subsequent anergy of immune cells; (v) induction of immune regulation; and/or (vi) inhibition or blocking of the activity of other presently unknown CD200 interactions that are immunostimulatory. As possible scenarios for this latter mechanism, different CD200 receptors exist (e.g., five receptors are known in mouse and two receptors are known in human), and these different receptors use different signaling mechanisms (e.g., extended cytoplasmic domains versus adapter proteins such as DAP12) (Wright et al. *J. Immunol.*, 2003, 171: 3034-3046). Accordingly, it is possible that the different signaling pathways mediated by the different CD200Rs could have opposing effects on the immune system. Additionally or alternatively, while it is thought that the immunosuppressive activity of CD200 is mediated via the CD200:CD200R interaction, an anti-CD200 receptor antibody may crosslink the CD200 receptor, thereby activating the receptor and inducing immune suppression.

II. CD200-Binding Agents

The present disclosure relates to compositions and methods for inhibiting or preventing graft rejection and prolonging graft survival. In certain aspects, the present disclosure relates to CD200-binding agents. As used herein, a CD200-binding agent includes any agent that is capable of specifically binding CD200. Examples of CD200-binding agents include but are not limited to polypeptides, antibodies, small molecules, and peptidomimetics. In certain embodiments, the CD200-binding agent disrupts the interaction of CD200 and CD200R. In other embodiments, the CD200-binding agents are capable of targeting CD200-expressing cells for depletion or elimination.

In certain aspects, the CD200-binding agents are polypeptides. Polypeptides utilized in the present disclosure can be constructed using different techniques that are known to persons skilled in the art. In one embodiment, the polypeptides are obtained by chemical synthesis. In other embodiments, the polypeptides are antibodies constructed from a fragment or several fragments of one or more antibodies. In further embodiments, the polypeptide is an anti-CD200 antibody as described herein.

Thus in certain embodiments, the CD200-binding agents are anti-CD200 antibodies. As used herein, the term "antibodies" refers to complete antibodies or antibody fragments capable of binding to CD200. Included are monoclonal and polyclonal antibodies, engineered antibodies (including chimeric, single chain, CDR-grafted, humanized, fully human antibodies, and artificially selected antibodies), and synthetic or semi-synthetic antibodies produced using phage display or alternative techniques, and other variations and derivatives of an antibody (e.g., an isolated, recombinant or synthetic antibody, antibody conjugate or antibody derivative, and an antigen-binding fragment). Also included are antibodies that are murine, chimeric, human, humanized, primatized, etc. Antigen-binding fragments include, for example, Fab, Fab', F(ab')$_2$, F(ab')$_3$, Fd, Fv, domain antibodies (dAb), other monovalent and divalent fragments, complementarity determining region (CDR) fragments, single-chain antibodies (e.g., scFv, scFab, scFabAC), diabodies, triabodies, minibodies, nanobodies, and polypeptides that contain at least a portion of an antibody that is sufficient to confer specific binding to CD200; and fusions and derivatives of the foregoing. An Fd fragment is an antibody fragment that consists of the $V_H$ and $C_{H1}$ domains; an Fv fragment consists of the $V_L$ and $V_H$ domains of a single arm of an antibody; an scFv fragment is a single chain antibody comprising a heavy chain variable region ($V_H$) and a light chain variable region ($V_L$) joined by a peptide linker; an scFab fragment is a single chain antibody comprising a fragment difficult (Fd) joined to a light chain by a peptide linker; a scFabAC fragment is a scFab variant without cysteines (see, e.g., Hust et al., *BMC Biotech* 7: 14 (2007)), and a dAb fragment (single domain antibody) comprises a single variable domain (e.g., a $V_H$ or a $V_L$ domain) (Ward et al., *Nature* 341:544-546 (1989)). See, e.g., Holliger and Hudson, *Nature Biotechnology* 23: 1126-1136 (2005). Small fragments, such as Fv and scFv, possess advantageous properties for diagnostic and therapeutic applications on account of their small size and consequent superior tissue distribution. To improve in vivo stability and the in vivo half-life of small fragments, the fragments may be conjugated (directly or indirectly) to a molecule such as poly(ethylene) glycol, for example.

The present disclosure also relates to antibodies engineered or produced in ways to contain variant or altered constant or Fc regions with either increased or decreased ability to bind one or more effector cells; such variant antibodies include but are not limited to antibodies in which the constant or Fc region contains altered glycosylation patterns. Antibodies with engineered or variant constant or Fc regions can be useful in modulating effector functions, such as, for example, ADCC and CDC. Such antibodies with engineered or variant constant or Fc regions may be useful in instances where CD200 is expressed in normal tissue, for example; variant anti-CD200 antibodies without effector function in these instances may elicit the desired therapeutic response while not damaging normal tissue.

The disclosure also relates to anti-CD200 antibodies comprising heavy and light chains as provided herein, including heavy and light chains that are homologous or similar to the heavy and/or light chains provided herein. "Homology" or "identity" or "similarity" refers to sequence similarity between two peptides or between two nucleic acid molecules. Homology and identity can each be determined by comparing a position in each sequence which may be aligned for purposes of comparison. When an equivalent position in the compared sequences is occupied by the same base or amino acid, then the molecules are identical at that position; when the equivalent site is occupied by the same or a similar amino acid residue (e.g., similar in steric and/or electronic nature), then the molecules can be referred to as homologous (similar) at that position. Expression as a percentage of homology/similarity or identity refers to a function of the number of identical or similar amino acids at positions shared by the compared sequences. The term "homology" describes a mathematically based comparison of sequence similarities which is used to identify genes or proteins with similar functions or motifs. As used herein, "identity" means the percentage of identical nucleotide or amino acid residues at corresponding positions in two or more sequences when the sequences are aligned to maximize sequence matching, i.e., taking into account gaps and insertions. Thus methods to determine identity are designed to give the largest match between the sequences tested (see Computational Molecular Biology, Lesk, A. M., ed., Oxford University Press, New York, 1988; Biocomputing: Informatics and Genome Projects, Smith, D. W., ed., Academic Press, New York, 1993; Computer Analysis of Sequence Data, Part I, Griffin, A. M., and Griffin, H. G., eds., Humana Press, New Jersey, 1994; Sequence Analysis in Molecular Biology, von Heinje, G., Academic Press, 1987; and Sequence Analysis Primer, Gribskov, M. and Devereux, J., eds., Stockton Press, New York, 1991; and Carillo, H., and Lipman, D., SIAM J. Applied Math., 48: 1073 (1988), Devereux, J., et al., Nucleic Acids Research 12(1): 387 (1984), BLASTP, BLASTN, FASTA (Altschul, S. F. et al., J. Mol. Biol. 215: 403-410 (1990) and Altschul et al. Nucleic Acids Res. 25: 3389-3402 (1997)) and BLAST X (BLAST Manual, Altschul, S., et al., NCBI NLM NIH Bethesda, Md. 20894; Altschul, S., et al., J. Mol. Biol. 215: 403-410 (1990)). A sequence which is "unrelated" or "non-homologous" shares less than 40% identity, though preferably less than 25% identity with a sequence of the present disclosure. In comparing two sequences, the absence of residues (amino acids or nucleic acids) or presence of extra residues also decreases the identity and homology/similarity.

Accordingly, the disclosure relates to antibodies as described herein without the leader sequences. Thus antibodies of the disclosure may comprise heavy and light chains in which the leader sequence is either absent or replaced by a different leader sequence. If host cells are used to produce antibodies of the present disclosure, appropriate leader sequences may therefore be selected according to the particular host cell used.

Antibodies may be produced by methods well known in the art. For example, monoclonal anti-CD200 antibodies may be generated using CD200 positive cells, CD200 polypeptide, or a fragment of CD200 polypeptide as an immunogen, thus raising an immune response in animals from which antibody-producing cells and in turn monoclonal antibodies may be isolated. The sequence of such antibodies may be determined and the antibodies or variants thereof produced by recombinant techniques. Recombinant techniques may be used to produce chimeric, CDR-grafted, humanized and fully human antibodies based on the sequence of the monoclonal antibodies as well as polypeptides capable of binding to CD200.

Moreover, antibodies derived from recombinant libraries ("phage antibodies") may be selected using CD200-positive cells, or polypeptides derived therefrom, as bait to isolate the antibodies or polypeptides on the basis of target specificity. The production and isolation of non-human and chimeric anti-CD200 antibodies are well within the purview of the skilled artisan.

Recombinant DNA technology is used to improve the antibodies produced in non-human cells. Thus, chimeric antibodies may be constructed in order to decrease the immunogenicity thereof in diagnostic or therapeutic applications. Moreover, immunogenicity may be minimized by humanizing the antibodies by CDR grafting and, optionally, framework modification. See, U.S. Pat. No. 5,225,539, the contents of which are incorporated herein by reference.

Antibodies may be obtained from animal serum or, in the case of monoclonal antibodies or fragments thereof, produced in cell culture. Recombinant DNA technology may be used to produce the antibodies according to established procedure, including procedures in bacterial or preferably mammalian cell culture. The selected cell culture system preferably secretes the antibody product.

In another embodiment, a process for the production of an antibody disclosed herein includes culturing a host, e.g. *E. coli* or a mammalian cell, which has been transformed with a hybrid vector. The vector includes one or more expression cassettes containing a promoter operably linked to a first DNA sequence encoding a signal peptide linked in the proper reading frame to a second DNA sequence encoding the antibody protein. The antibody protein is then collected and isolated. Optionally, the expression cassette may include a promoter operably linked to polycistronic, for example bicistronic, DNA sequences encoding antibody proteins each individually operably linked to a signal peptide in the proper reading frame.

Multiplication of hybridoma cells or mammalian host cells in vitro is carried out in suitable culture media, which include the customary standard culture media (such as, for example Dulbecco's Modified Eagle Medium (DMEM) or RPMI 1640 medium), optionally replenished by a mammalian serum (e.g. fetal calf serum), or trace elements and growth sustaining supplements (e.g. feeder cells such as normal mouse peritoneal exudate cells, spleen cells, bone marrow macrophages, 2-aminoethanol, insulin, transferrin, low density lipoprotein, oleic acid, or the like). Multiplication of host cells which are bacterial cells or yeast cells is likewise carried out in suitable culture media known in the art. For example, for bacteria suitable culture media include medium LE, NZCYM, NZYM, NZM, Terrific Broth, SOB, SOC, 2×YT, or M9 Minimal Medium. For yeast, suitable culture media include medium YPD, YEPD, Minimal Medium, or Complete Minimal Dropout Medium.

In vitro production provides relatively pure antibody preparations and allows scale-up production to give large amounts of the desired antibodies. Techniques for bacterial cell, yeast, plant, or mammalian cell cultivation are known in the art and include homogeneous suspension culture (e.g. in an airlift reactor or in a continuous stirrer reactor), and immobilized or entrapped cell culture (e.g. in hollow fibers, microcapsules, on agarose microbeads or ceramic cartridges).

Large quantities of the desired antibodies can also be obtained by multiplying mammalian cells in vivo. For this purpose, hybridoma cells producing the desired antibodies are injected into histocompatible mammals to cause growth of antibody-producing tumors. Optionally, the animals are primed with a hydrocarbon, especially mineral oils such as pristane (tetramethyl-pentadecane), prior to the injection. After one to three weeks, the antibodies are isolated from the body fluids of those mammals. For example, hybridoma cells obtained by fusion of suitable myeloma cells with antibody-producing spleen cells from Balb/c mice, or transfected cells derived from hybridoma cell line Sp2/0 that produce the desired antibodies are injected intraperitoneally into Balb/c mice optionally pre-treated with pristane. After one to two weeks, ascitic fluid is taken from the animals.

The foregoing, and other, techniques are discussed in, for example, Kohler and Milstein, (1975) Nature 256:495-497; U.S. Pat. No. 4,376,110; Harlow and Lane, Antibodies: a Laboratory Manual, (1988) Cold Spring Harbor, the disclosures of which are all incorporated herein by reference. Techniques for the preparation of recombinant antibody molecules are described in the above references and also in, for example WO97/08320; U.S. Pat. No. 5,427,908; U.S. Pat. No. 5,508,717; Smith, 1985, Science, Vol. 225, pp 1315-1317; Parmley and Smith, 1988, Gene 73, pp 305-318; De La Cruz et al., 1988, Journal of Biological Chemistry, 263 pp 4318-4322; U.S. Pat. No. 5,403,484; U.S. Pat. No. 5,223,409; WO88/06630; WO92/15679; U.S. Pat. No. 5,780,279; U.S. Pat. No. 5,571,698; U.S. Pat. No. 6,040,136; Davis et al., 1999, Cancer Metastasis Rev., 18(4):421-5; Taylor, et al., Nucleic Acids Research 20 (1992): 6287-6295; Tomizuka et al., Proc. Natl. Academy of Sciences USA 97(2) (2000): 722-727. The contents of all these references are incorporated herein by reference.

The cell culture supernatants are screened for the desired antibodies, preferentially by immunofluorescent staining of CD200-positive cells, by immunoblotting, by an enzyme immunoassay, e.g. a sandwich assay or a dot-assay, or a radioimmunoassay.

For isolation of the antibodies, the immunoglobulins in the culture supernatants or in the ascitic fluid may be concentrated, e.g. by precipitation with ammonium sulfate, dialysis against hygroscopic material such as polyethylene glycol, filtration through selective membranes, or the like. If necessary and/or desired, the antibodies are purified by the customary chromatography methods, for example gel filtration, ion-exchange chromatography, chromatography over DEAE-cellulose and/or (immuno-) affinity chromatography, e.g. affinity chromatography with one or more surface polypeptides derived from a CD200-positive cell line, or with Protein-A or -G.

Another embodiment provides a process for the preparation of a bacterial cell line secreting antibodies directed against CD200 in a suitable mammal. For example a rabbit is immunized with pooled samples from CD200-positive tissue or cells or CD200 polypeptide or fragments thereof. A phage display library produced from the immunized rabbit is constructed and panned for the desired antibodies in accordance with methods well known in the art (such as, for example, the methods disclosed in the various references incorporated herein by reference).

Hybridoma cells secreting the monoclonal antibodies are also disclosed. The preferred hybridoma cells are genetically stable, secrete monoclonal antibodies described herein of the desired specificity, and can be expanded from deep-frozen cultures by thawing and propagation in vitro or as ascites in vivo.

In another embodiment, a process is provided for the preparation of a hybridoma cell line secreting monoclonal antibodies against CD200. In that process, a suitable mammal, for example a Balb/c mouse, is immunized with one or more polypeptides or antigenic fragments of CD200 or with one or more polypeptides or antigenic fragments derived from a CD200-positive cell, the CD200-positive cell itself, or an antigenic carrier containing a purified polypeptide as described. Antibody-producing cells of the immunized mammal are grown briefly in culture or fused with cells of a suitable myeloma cell line. The hybrid cells obtained in the fusion are cloned, and cell clones secreting the desired antibodies are selected. For example, spleen cells of Balb/c mice immunized with a CD200-positive Chronic Lymphocytic Leukemia (CLL) cell line are fused with cells of the myeloma cell line PAI or the myeloma cell line Sp2/0-Ag 14. The obtained hybrid cells are then screened for secretion of the desired antibodies and positive hybridoma cells are cloned.

Preferred is a process for the preparation of a hybridoma cell line, characterized in that Balb/c mice are immunized by injecting subcutaneously and/or intraperitoneally between $10^6$ and $10^7$ cells of a CD200-positive cell line several times, e.g. four to six times, over several months, e.g. between two and four months. Spleen cells from the immunized mice are taken two to four days after the last injection and fused with cells of the myeloma cell line PAI in the presence of a fusion promoter, preferably polyethylene glycol. Preferably, the myeloma cells are fused with a three- to twenty-fold excess of spleen cells from the immunized mice in a solution containing about 30% to about 50% polyethylene glycol of a molecular weight around 4000. After the fusion, the cells are expanded in suitable culture media as described hereinbefore, supplemented with a selection medium, for example HAT medium, at regular intervals in order to prevent normal myeloma cells from overgrowing the desired hybridoma cells.

The antibodies and fragments thereof can be "chimeric". Chimeric antibodies and antigen-binding fragments thereof comprise portions from two or more different species (e.g., mouse and human). Chimeric antibodies can be produced with mouse variable regions of desired specificity spliced into human constant domain gene segments (for example, U.S. Pat. No. 4,816,567). In this manner, non-human antibodies can be modified to make them more suitable for human clinical application.

The monoclonal antibodies of the present disclosure also include "humanized" forms of the non-human (i.e., mouse) antibodies. Humanized or CDR-grafted mAbs are particularly useful as therapeutic agents for humans because they are not cleared from the circulation as rapidly as mouse antibodies and do not typically provoke an adverse immune reaction. Generally, a humanized antibody has one or more amino acid residues introduced into it from a non-human source. These non-human amino acid residues are often referred to as "import" residues, which are typically taken from an "import" variable domain. Methods of preparing humanized antibodies are generally well known in the art. For example, humanization can be essentially performed following the method of Winter and co-workers (Jones et al., Nature 321: 522-525 (1986); Riechmann et al., Nature, 332:323-327 (1988); Verhoeyen et al., Science, 239: 1534-1536 (1988)), by substituting rodent CDRs or CDR sequences for the corresponding sequences of a human antibody. Also see Staelens et al. 2006 Mol Immunol 43: 1243-1257. In particular embodiments, humanized forms of non-human (e.g., mouse) antibodies are human antibodies (recipient antibody) in which hypervariable (CDR) region residues of the recipient antibody are replaced by hypervariable region residues from a non-human species (donor antibody) such as a mouse, rat, rabbit, or non-human primate having the desired specificity, affinity, and binding capacity. In some instances, framework region residues of the human immunoglobulin are also replaced by corresponding non-human residues (so called "back mutations"). In addition, phage display libraries can be used to vary amino acids at chosen positions within the antibody sequence. The properties of a humanized antibody are also affected by the choice of the human framework. Furthermore, humanized and chimerized antibodies can be modified to comprise residues that are not found in the recipient antibody or in the donor antibody in order to further improve antibody properties, such as, for example, affinity or effector function.

Fully human antibodies are also provided in the disclosure. The term "human antibody" includes antibodies having variable and constant regions (if present) derived from human germline immunoglobulin sequences. Human antibodies can include amino acid residues not encoded by human germline immunoglobulin sequences (e.g., mutations introduced by random or site-specific mutagenesis in vitro or by somatic mutation in vivo). However, the term "human antibody" does not include antibodies in which CDR sequences derived from the germline of another mammalian species, such as a mouse, have been grafted onto human framework sequences (i.e., humanized antibodies). Fully human or human antibodies may be derived from transgenic mice carrying human antibody genes (carrying the variable (V), diversity (D), joining (J), and constant (C) exons) or from human cells. For example, it is now possible to produce transgenic animals (e.g., mice) that are capable, upon immunization, of producing a full repertoire of human antibodies in the absence of endogenous immunoglobulin production (see, e.g., Jakobovits et al., *Proc. Natl. Acad. Sci. USA*, 90:2551 (1993); Jakobovits et al., *Nature*, 362:255-258 (1993); Bruggemann et al., *Year in Immuno.*, 7:33 (1993); and Duchosal et al. *Nature* 355:258 (1992). Transgenic mice strains can be engineered to contain gene sequences from unrearranged human immunoglobulin genes. The human sequences may code for both the heavy and light chains of human antibodies and would function correctly in the mice, undergoing rearrangement to provide a wide antibody repertoire similar to that in humans. The transgenic mice can be immunized with the target protein (e.g., CD200, fragments thereof, or cells expressing CD200) to create a diverse array of specific antibodies and their encoding RNA. Nucleic acids encoding the antibody chain components of such antibodies may then be cloned from the animal into a display vector. Typically, separate populations of nucleic acids encoding heavy and light chain sequences are cloned, and the separate populations then recombined on insertion into the vector, such that any given copy of the vector receives a random combination of a heavy and a light chain. The vector is designed to express antibody chains so that they can be assembled and displayed on the outer surface of a display package containing the vector. For example, antibody chains can be expressed as fusion proteins with a phage coat protein from the outer surface of the phage. Thereafter, display packages can be screened for display of antibodies binding to a target.

In addition, human antibodies can be derived from phage-display libraries (Hoogenboom et al., *J. Mol. Biol.*, 227:381 (1992); Marks et al., *J. Mol. Biol.*, 222:581-597 (1991); Vaughan et al. *Nature Biotech* 14:309 (1996)). Synthetic phage libraries can be created which use randomized combinations of synthetic human antibody V-regions. By selection on antigen fully human antibodies can be made in which the V-regions are very human-like in nature. See U.S. Pat. Nos. 6,794,132, 6,680,209, 4,634,666, and Ostberg et al. (1983), *Hybridoma* 2:361-367, the contents of which are incorporated by reference.

For the generation of human antibodies, also see Mendez et al. *Nature Genetics* 15:146-156 (1997), Green and Jakobovits *J. Exp. Med.* 188:483-495 (1998), the disclosures of which are hereby incorporated by reference. Human antibodies are further discussed and delineated in U.S. Pat. Nos. 5,939,598 and 6,673,986. Also see U.S. Pat. Nos. 6,114,598, 6,075,181, and 6,162,963, all filed Jun. 5, 1995. Also see U.S. Pat. No. 6,150,584, filed Oct. 2, 1996 and U.S. Pat. Nos. 6,713,610 and 6,657,103 as well as U.S. patent application Ser. Nos. 10/421,011 (US 2003-0229905 A1), 10/455,013 (US 2004-0010810 A1), 10/627,250 (US 2004-0093622 A1), 10/656,623 (US 2006-0040363 A1), 10/658,521 (US 2005-0054055 A1), 10/917,703 (US 2005-0076395 A1) and 10/978,297 (US 2005-0287630 A1). See also PCT/US93/06926 filed on Jul. 23, 1993, European Patent No. EP 0 463 151 B1, grant published Jun. 12, 1996, International Patent Application No. WO 94/02602, published Feb. 3, 1994, International Patent Application No. WO 96/34096, published Oct. 31, 1996, and WO 98/24893, published Jun. 11, 1998. The disclosures of each of the above-cited patents, applications, and references are hereby incorporated by reference in their entirety.

In an alternative approach, others, including GenPharm International, Inc., have utilized a "minilocus" approach. In the minilocus approach, an exogenous Ig locus is mimicked through the inclusion of pieces (individual genes) from the Ig locus. Thus, one or more $V_H$ genes, one or more $D_H$ genes, one or more $J_H$ genes, a mu constant region, and a second constant region (preferably a gamma constant region) are formed into a construct for insertion into an animal. This approach is described in U.S. Pat. No. 5,545,807 to Surani et al. and U.S. Pat. Nos. 5,545,806, 5,625,825, 5,625,126, 5,633,425, 5,661,016, 5,770,429, 5,789,650, and 5,814,318 each to Lonberg and Kay, U.S. Pat. No. 5,591,669 to Krimpenfort and Berns, U.S. Pat. Nos. 5,612,205, 5,721,367, 5,789,215 to Berns et al., and U.S. Pat. No. 5,643,763 to Choi and Dunn, and GenPharm International. Also see U.S. Pat. Nos. 5,569,825, 5,877,397, 6,300,129, 5,874,299, 6,255,458, and 7,041,871, the disclosures of which are hereby incorporated by reference. See also European Patent No. 0 546 073 B1, International Patent Application Nos. WO 92/03918, WO 92/22645, WO 92/22647, WO 92/22670, WO 93/12227, WO 94/00569, WO 94/25585, WO 96/14436, WO 97/13852, and WO 98/24884, the disclosures of which are hereby incorporated by reference in their entirety. See further Taylor et al. (1992 Nucleic Acids Res. 20: 6287), Chen et al. (1993 Int. Immunol. 5: 647), Tuaillon et al. (1993 Proc. Natl. Acad. Sci. USA 90: 3720-4), Choi et al., (1993 Nature Genetics 4: 117), Lonberg et al. (1994 Nature 368: 856-859), Taylor et al. (1994 International Immunology 6: 579-591), and Tuaillon et al. (1995 J. Immunol. 154: 6453-65), Fishwild et al. (1996 Nature Biotechnology 14: 845), and Tuaillon et al. (2000 Eur J. Immunol. 10: 2998-3005), the disclosures of which are hereby incorporated by reference in their entirety.

In certain embodiments, de-immunized anti-CD200 antibodies or antigen-binding fragments thereof are provided. De-immunized antibodies or antigen-binding fragments thereof may be modified so as to render the antibody or antigen-binding fragment thereof non-immunogenic, or less immunogenic, to a given species. De-immunization can be achieved by modifying the antibody or antigen-binding fragment thereof utilizing any of a variety of techniques known to persons skilled in the art (see e.g., PCT Publication Nos. WO 04/108158 and WO 00/34317). For example, an antibody or antigen-binding fragment thereof may be de-immunized by identifying potential T cell epitopes and/or B cell epitopes within the amino acid sequence of the antibody or antigen-binding fragment thereof and removing one or more of the potential T cell epitopes and/or B cell epitopes from the antibody or antigen-binding fragment thereof, for example, using recombinant techniques. The modified antibody or antigen-binding fragment thereof may then optionally be produced and tested to identify antibodies or antigen-binding fragments thereof that have retained one or more desired biological activities, such as, for example, binding affinity, but have reduced immunogenicity. Methods for identifying potential T cell epitopes and/or B cell epitopes may be carried out using techniques known in the art; such as, for example, computational methods (see e.g., PCT Publication No. WO 02/069232), in vitro or in silico techniques, and biological assays or physical methods (such as, for example, determination of the binding of peptides to MHC molecules, determination of the binding of peptide:MHC complexes to the T cell receptors from the species to receive the antibody or antigen-binding fragment thereof, testing of the protein or peptide parts thereof using transgenic animals with the MHC molecules of the species to receive the antibody or antigen-binding fragment thereof, or testing with transgenic animals reconstituted with immune system cells from the species to receive the antibody or antigen-binding fragment thereof, etc.). In various embodiments, the de-immunized anti-CD200 antibodies described herein include de-immunized antigen-binding fragments, Fab, Fv, scFv, Fab' and F(ab)$_2$, monoclonal antibodies, murine antibodies, engineered antibodies (such as, for example, chimeric, single chain, CDR-grafted, humanized, fully human antibodies, and artificially selected antibodies), synthetic antibodies and semi-synthetic antibodies.

In a further embodiment, recombinant DNA comprising an insert coding for a heavy chain variable domain and/or for a light chain variable domain of antibodies directed to CD200 or a CD200-positive cell line are produced. The term DNA includes coding single stranded DNAs, double stranded DNAs consisting of said coding DNAs and of complementary DNAs thereto, or these complementary (single stranded) DNAs themselves.

Furthermore, DNA encoding a heavy chain variable domain and/or a light chain variable domain of antibodies directed to CD200 or the CD200-positive cell line can be enzymatically or chemically synthesized DNA having the authentic DNA sequence coding for a heavy chain variable domain and/or for the light chain variable domain, or a mutant thereof. A mutant of the authentic DNA is a DNA encoding a heavy chain variable domain and/or a light chain variable domain of the above-mentioned antibodies in which one or more amino acids are deleted, inserted, or exchanged with one or more other amino acids. Preferably said modification(s) are outside the CDRs of the heavy chain variable domain and/or of the light chain variable domain of the antibody in humanization and expression optimization applications. The term mutant DNA also embraces silent mutants wherein one or more nucleotides are replaced by other nucleotides with the new codons coding for the same amino acid(s). The term mutant sequence also includes a degenerate sequence. Degenerate sequences are degenerate within the meaning of the genetic code in that an unlimited number of nucleotides are replaced by other nucleotides without resulting in a change of the amino acid sequence originally encoded. Such degenerate sequences may be useful due to their different restriction sites and/or frequency of particular codons which are preferred by the specific host, particularly E. coli, to obtain an optimal expression of the heavy chain variable domain and/or a light chain variable domain.

The term mutant is intended to include a DNA mutant obtained by in vitro mutagenesis of the authentic DNA according to methods known in the art.

For the assembly of complete tetrameric immunoglobulin molecules and the expression of chimeric antibodies, the recombinant DNA inserts coding for heavy and light chain variable domains are fused with the corresponding DNAs coding for heavy and light chain constant domains, then transferred into appropriate host cells, for example after incorporation into hybrid vectors.

Recombinant DNAs including an insert coding for a heavy chain variable domain of an antibody directed to CD200 or a CD200-positive cell line fused to a human constant domain IgG, for example γ1, γ2, -γ3 or γ4; in particular embodiments γ1 or γ4 may be used. Recombinant DNAs including an insert coding for a light chain variable domain of an antibody directed to the cell line disclosed herein fused to a human constant domain κ or λ, preferably κ are also provided.

Another embodiment pertains to recombinant DNAs coding for a recombinant polypeptide wherein the heavy chain variable domain and the light chain variable domain are linked by way of a spacer group, optionally comprising a signal sequence facilitating the processing of the antibody in the host cell and/or a DNA sequence encoding a peptide facilitating the purification of the antibody and/or a cleavage site and/or a peptide spacer and/or an agent. The DNA coding for an agent is intended to be a DNA coding for the agent useful in diagnostic or therapeutic applications. Thus, agent molecules which are toxins or enzymes, especially enzymes capable of catalyzing the activation of prodrugs, are particularly indicated. The DNA encoding such an agent has the sequence of a naturally occurring enzyme or toxin encoding DNA, or a mutant thereof, and can be prepared by methods well known in the art.

Accordingly, the monoclonal antibodies or antigen-binding fragments of the disclosure can be naked antibodies or antigen-binding fragments thereof that are not conjugated to other agents, for example, a therapeutic agent or detectable label. Alternatively, the monoclonal antibody or antigen-binding fragment thereof can be conjugated to an agent such as, for example, a cytotoxic agent, a small molecule, a hormone, an enzyme, a growth factor, a cytokine, a ribozyme, a peptidomimetic, a chemical, a prodrug, a nucleic acid molecule including coding sequences (such as antisense, RNAi, gene-targeting constructs, etc.), or a detectable label (e.g., an NMR or X-ray contrasting agent, fluorescent molecule, etc.). In certain embodiments, an anti-CD200 polypeptide or antigen-binding fragment (e.g., Fab, Fv, single-chain scFv, Fab' and F(ab')$_2$) is linked to a molecule that increases the half-life of said polypeptide or antigen-binding fragment. Molecules that may be linked to said anti-CD200 polypeptide or antigen-binding fragment include but are not limited to serum proteins including albumin, polypeptides, other proteins or protein domains, and PEG.

Several possible vector systems are available for the expression of cloned heavy chain and light chain genes in mammalian cells. One class of vectors relies upon the integration of the desired gene sequences into the host cell genome. Cells which have stably integrated DNA can be selected by simultaneously introducing drug resistance genes such as E. coli gpt (Mulligan, R. C. and Berg, P., Proc. Natl. Acad. Sci., USA, 78: 2072 (1981)) or Tn5 neo (Southern, P. J. and Berg, P., J. Mol. Appl. Genet., 1: 327 (1982)). The selectable marker gene can be either linked to the DNA gene sequences to be expressed, or introduced into the same cell by co-transfection (Wigler, M. et al., Cell, 16: 77 (1979)). A second class of vectors utilizes DNA elements which confer autonomously replicating capabilities to an extrachromosomal plasmid. These vectors can be derived from animal viruses, such as bovine papillomavirus (Sarver, N. et al., Proc. Natl. Acad. Sci., USA, 79: 7147 (1982)), polyoma virus (Deans, R. J. et al., Proc. Natl. Acad. Sci., USA, 81: 1292 (1984)), or SV40 virus (Lusky, M. and Botchan, M., Nature, 293: 79 (1981)).

Since an immunoglobulin cDNA is comprised only of sequences representing the mature mRNA encoding an antibody protein, additional gene expression elements regulating transcription of the gene and processing of the RNA are required for the synthesis of immunoglobulin mRNA. These elements may include splice signals, transcription promoters, including inducible promoters, enhancers, and termination signals. cDNA expression vectors incorporating such elements include those described by Okayama, H. and Berg, P., Mol. Cell. Biol., 3: 280 (1983); Cepko, C. L. et al., Cell, 37: 1053 (1984); and Kaufman, R. J., Proc. Natl. Acad. Sci., USA, 82: 689 (1985).

In the therapeutic embodiments of the present disclosure, bispecific antibodies are contemplated. Bispecific antibodies are monoclonal, preferably human or humanized, antibodies that have binding specificities for at least two different antigens. In the present case, one of the binding specificities is for the CD200 antigen on a cell (such as, e.g., a cancer cell or immune cell), the other one is for any other antigen, and preferably for a cell-surface protein or receptor or receptor subunit.

Methods for making bispecific antibodies are within the purview of those skilled in the art. Traditionally, the recombinant production of bispecific antibodies is based on the co-expression of two immunoglobulin heavy-chain/light-chain pairs, where the two heavy chains have different specificities (Milstein and Cuello, Nature, 305:537-539 (1983)). Antibody variable domains with the desired binding specificities (antibody-antigen combining sites) can be fused to immunoglobulin constant domain sequences. The fusion preferably is with an immunoglobulin heavy-chain constant domain, including at least part of the hinge, CH2, and CH3 regions. DNAs encoding the immunoglobulin heavy-chain fusions and, if desired, the immunoglobulin light chain, are inserted into separate expression vectors, and are co-transfected into a suitable host organism. For further details of illustrative currently known methods for generating bispecific antibodies see, for example, Suresh et al., Methods in Enzymology, 121:210 (1986); WO 96/27011; Brennan et al., Science 229:81 (1985); Shalaby et al., J. Exp. Med. 175:217-225 (1992); Kostelny et al., J. Immunol. 148(5):1547-1553 (1992); Hollinger et al., Proc. Natl. Acad. Sci. USA 90:6444-6448 (1993); Gruber et al., J. Immunol. 152:5368 (1994); and Tutt et al., J. Immunol. 147:60 (1991). Bispecific antibodies also include cross-linked or heteroconjugate antibodies. Heteroconjugate antibodies may be made using any convenient cross-linking methods. Suitable cross-linking agents are well known in the art, and are disclosed in U.S. Pat. No. 4,676,980, along with a number of cross-linking techniques.

Various techniques for making and isolating bispecific antibody fragments directly from recombinant cell culture have also been described. For example, bispecific antibodies have been produced using leucine zippers. Kostelny et al., J. Immunol., 148(5):1547-1553 (1992). The leucine zipper peptides from the Fos and Jun proteins may be linked to the Fab' portions of two different antibodies by gene fusion. The antibody homodimers may be reduced at the hinge region to form monomers and then re-oxidized to form the antibody heterodimers. This method can also be utilized for the production of antibody homodimers. The "diabody" technology described by Hollinger et al., *Proc. Natl. Acad. Sci. USA* 90:6444-6448 (1993) has provided an alternative mechanism for making bispecific antibody fragments. The fragments comprise a heavy-chain variable domain ($V_H$) connected to a light-chain variable domain ($V_L$) by a linker which is too short to allow pairing between the two domains on the same chain. Accordingly, the $V_H$ and $V_L$ domains of one fragment are forced to pair with the complementary $V_L$ and $V_H$ domains of another fragment, thereby forming two antigen-binding sites. Another strategy for making bispecific antibody fragments by the use of single-chain Fv (scFv) dimers has also been reported. See Gruber et al., *J. Immunol.*, 152:5368 (1994). Alternatively, the antibodies can be "linear antibodies" as described in Zapata et al. *Protein Eng.* 8(10):1057-1062 (1995). Briefly, these antibodies comprise a pair of tandem Fd segments ($V_H$—$C_H$1-$V_H$—$C_H$1) which form a pair of antigen binding regions. Linear antibodies can be bispecific or monospecific.

In certain embodiments, the disclosure relates to fusion molecules wherein an anti-CD200 antibody or antigen-binding fragment is linked to a second molecule. Accordingly, the present disclosure provides anti-CD200 antibody conjugates. Anti-CD200 antibody conjugates comprise an antibody or antigen-binding portion of an anti-CD200 antibody and a heterologous moiety. The heterologous moiety may be a polypeptide (such as human serum albumin), a small molecule, a nucleic acid, a polymer (including natural and synthetic polymers such as PEG), metals, etc. The heterologous moiety may be a detectable or labeling moiety, such as a fluorescent or luminescent agent, or it may be a cytotoxic agent, an antibiotic, or a radioisotope or radionuclide. Antibody conjugates or fusion molecules of the present disclosure may therefore comprise, for example, a small molecule, polypeptide, peptidomimetic, heteroclitic peptide, a chemotherapeutic agent, an immunomodulatory agent, a targeting moiety, or a nucleic acid construct (e.g., antisense, RNAi, or gene-targeting construct).

In particular embodiments where increased integrity or longevity of an anti-CD200 antibody or fragment thereof is desired, the antibody or fragment thereof may be conjugated to a molecule that will increase the half-life of the fragment in vivo. Such molecules include polymers such as PEG or other synthetic polymers—e.g., polyalkylene, polyalkenylene, polyoxyalkylene, etc. A fragment may alternatively be fused or otherwise linked to a polypeptide, protein domain, serum protein, or albumin. The antigen-binding fragment may be a Fab, Fv, single-chain fragments or scFv, Fab', F(ab')$_2$, or F(ab')$_3$, for example.

III. Methods of Inhibiting Immune Responses

A. Methods of Inhibiting a Humoral Immune Response

The immune system is capable of producing two types of antigen-specific responses to foreign antigens: cell-mediated immunity, which refers to effector functions of the immune system mediated by T lymphocytes, and humoral immunity, which refers to production of antigen-specific antibodies by B lymphocytes. Humoral immunity is mediated by activated B cells, which secrete antibodies specific to antigens on the surfaces of invading microbes, for example (such as viruses or bacteria). The antibodies bind to and target the invading microbes for destruction.

The development of humoral immunity against most antigens requires not only antibody-producing B cells or B lymphocytes but also the involvement of helper T (Th) cells or Th lymphocytes. (Mitchison, *Eur. J. Immunol.*, 1:18-25 (1971); Claman and Chaperon, *Transplant Rev.*, 1:92-119 (1969); Katz et al, *Proc. Natl. Acad. Sci. USA*, 70:2624-2629 (1973); Reff et al., *Nature*, 226:1257-1260 (1970)). Th cells provide certain signals in response to stimulation by thymus-dependent antigens. While soluble molecules released by Th cells (for instance cytokines such as IL-4 and IL-5) mediate some B lymphocyte activation, B cell activation also requires a contact-dependent interaction between B cells and Th cells (Hirohata et al., *J. Immunol.*, 140:3736-3744 (1988); Bartlett et al., *J. Immunol.*, 143:1745-1765 (1989); Brian, *Proc. Natl. Acad. Sci. USA*, 85:564-568 (1988); Hodgkin et al., *J. Immunol.*, 145:2025-2034 (1990); and Noelle et al, *J. Immunol.*, 146:1118-1124 (1991)).

The present disclosure demonstrates that administration of an anti-CD200 antibody inhibits B cell activity. Specifically, the disclosure shows that an anti-CD200 antibody can reduce the level of circulating immunoglobulin (e.g., IgG and IgM) following immune stimulation.

Accordingly, in certain embodiments, the present disclosure relates to methods and compositions for preventing or inhibiting a humoral immune response in a subject in need thereof comprising administering a CD200-binding agent. In certain embodiments, the binding agent is an anti-CD200 antibody or antigen-binding fragment thereof as described herein.

In some embodiments, administration of an anti-CD200 antibody is effective to inhibit B cells. For example, an anti-CD200 antibody of the present disclosure may be effective to target and/or inhibit circulating B cells and/or mature, antibody-secreting B cells. Accordingly, the methods and compositions of the disclosure may be effective to reduce or deplete circulating B cells as well as circulating immunoglobulin. In further embodiments, administration of an anti-CD200 antibody results in decreased levels of circulating IgG and/or IgM immunoglobulin.

While not wishing to be restricted to any particular mode of action, an anti-CD200 antibody may mediate ADCC, CDC, and/or apoptosis of B cells to which the antibody binds, as described elsewhere herein. The antibody may be a murine, chimeric, human, humanized, primatized, or de-immunized anti-CD200 antibody or antigen-binding fragment thereof. Optionally, the antibody may elicit increased effector function. However, as noted earlier, effector function, while possibly playing a role, is not the only means by which the desired effect is brought about.

A subject in need of prevention or inhibition of a humoral immune response may be, in certain embodiments, a patient with an autoimmune disorder or a transplant recipient. Accordingly, in certain embodiments the disclosure relates to immunotherapeutic compositions and methods for the treatment and prevention of graft versus host disease (GVHD) and graft rejection in patients wherein the compositions and methods comprise an agent that inhibits the interaction between CD200 and CD200R, preferably wherein said agent is an anti-CD200 antibody. In particular embodiments, the transplant recipient or patient with an autoimmune disorder is human. In further embodiments, the disclosure relates to methods for treating or preventing an acute or a chronic humoral rejection in a transplant recipient.

In certain embodiments, the agent, e.g., an anti-CD200 antibody, is used in combination with lower doses of traditional therapeutic drugs than would be possible in the absence of the agent (e.g., anti-CD200 antibody). In another embodiment, the compositions and methods of the disclosure obviate the need for a more severe form of therapy, such as radiation therapy, high-dose immunomodulatory therapy, or splenectomy. Combination treatments are discussed in more detail below and include, for example, adriamycin, azathiopurine, busulfan, cyclophosphamide, cyclosporine A, Cytoxan, fludarabine, 5-fluorouracil, methotrexate, mycophenolate mofetil, a nonsteroidal anti-inflammatory, rapamycin, sirolimus, and tacrolimus. Other examples include antibodies such as, e.g., OKT3™ (muromonab-CD3), CAMPATH™-1G, CAMPATH™-1H (alemtuzumab), or CAMPATH™-1M, SIMULEC™ (basiliximab), ZENAPAX™ (daclizumab), RITUXAN™ (rituximab), and anti-thymocyte globulin.

In embodiments where an anti-CD200 is administered to a transplant recipient to inhibit a humoral immune response, the anti-CD200 antibody may be administered to a transplant recipient prior to or following transplantation, alone or in combination with one or more therapeutic agents or regimens for the treatment or prevention of GVHD and graft rejection. For example, an anti-CD200 antibody may be used to deplete alloantibodies from a transplant recipient prior to or following transplantation of an allogeneic graft. An anti-CD200 antibody may also be used to immuno-deplete CD200+ antibody-producing cells from the graft ex vivo, prior to transplantation, or in the donor, as prophylaxis against GVHD and graft rejection.

A transplant recipient in need of prophylaxis or treatment for humoral rejection may be identified according to the knowledge and skill in the art. For example, a transplant recipient in need of prophylaxis against graft rejection may be identified as a patient or patient population having detectable circulating anti-HLA alloantibodies prior to transplantation. In another example, the patient or patient population is identified as having panel reactive alloantibodies prior to transplantation. The presence of detectable circulating anti-HLA alloantibodies in a transplant recipient post-transplantation can also be used to identify a patient or patient population in need of treatment for humoral rejection according to the disclosure. The patient or patient population in need of treatment for humoral rejection can also be identified according to other clinical criteria that indicate that a transplant recipient is at risk for developing a humoral rejection or has already developed a humoral rejection. For example, a transplant recipient in need of treatment for humoral rejection may be identified as a patient or patient population in an early stage of humoral rejection, such as a latent humoral response characterized by circulating anti-donor alloantibodies. An early stage humoral rejection may also be a silent reaction characterized by circulating anti-donor alloantibodies and C4d deposition, or a subclinical rejection characterized by circulating anti-donor alloantibodies, C4d deposition, and tissue pathology. In later stages, the recipient may be identified as a patient or patient population presenting with clinical indications of humoral rejection characterized according to the knowledge and skill in the art—for example, by circulating anti-donor alloantibodies, C4d deposition, tissue pathology, and graft dysfunction.

Anti-CD200 antibodies as described herein may be used to inhibit or prevent a humoral immune response in recipients of various kinds of transplanted cells, tissues, and organs. For example, a graft may be autologous, allogeneic, or xenogeneic to the recipient. The graft may be a cell, tissue, or organ graft, including, but not limited to, bone marrow grafts, peripheral blood stem cell grafts, skin grafts, arterial and venous grafts, pancreatic islet cell grafts, and transplants of the kidney, liver, pancreas, thyroid, and heart. In one embodiment, the autologous graft is a bone marrow graft, an arterial graft, a venous graft, or a skin graft. In another embodiment, the allograft is a bone marrow graft, a corneal graft, a kidney transplant, a heart transplant, a liver transplant, a lung transplant, a pancreatic transplant, a pancreatic islet cell transplant, or a combined transplant of a kidney and pancreas. In another embodiment, the graft is a xenograft, preferably wherein the donor is a pig. Further, an anti-CD200 antibody, used alone or in combination with a second agent, may also be used to suppress a deleterious immune response to a non-biological graft or implant, including, but not limited to, an artificial joint, a stent, or a pacemaker device.

Accordingly, the present disclosure relates to a method of inhibiting or preventing a humoral immune response (such as but not limited to humoral graft rejection) in a subject in need thereof comprising administering to the subject an agent which inhibits an interaction between CD200 and CD200R, e.g., anti-CD200 antibody, either alone or preferably in combination with one or more other therapeutic agents. In certain embodiments, the antibody is administered in an amount sufficient to decrease the number of circulating B cells and/or decrease the amount of circulating immunoglobulin (e.g., IgG and/or IgM).

B. Methods of Inhibiting a Cellular Immune Response

Cellular immune responses are initiated when antigen-presenting cells present an antigen to CD4+ T helper (Th) lymphocytes resulting in T cell activation, proliferation, and differentiation of effector T lymphocytes (e.g., cytotoxic CD8+ T cells). Following exposure to antigens (such as exposure resulting from infection or the grafting of foreign tissue), naive T cells differentiate into Th1 and Th2 cells. Th1 cells produce IFN-γ and IL-2, both of which are associated with cell-mediated immune responses. Th1 cells play a role in immune responses commonly involved in the rejection of foreign tissue grafts as well as many autoimmune diseases. Th2 cells produce cytokines such as IL-4 and are associated with antibody-mediated immune responses (i.e., B cell-mediated responses) such as those responses commonly involved in allergies and allergic inflammatory responses such as asthma. Th2 cells may also contribute to the rejection of grafts. In numerous situations, a cellular immune response is desirable, for example, in defending the body against bacterial or viral infection, inhibiting the proliferation of cancerous cells and the like. However, in other situations, such effector T cells are undesirable, e.g., in a graft recipient.

Whether the immune system is activated by or tolerized to an antigen depends upon the balance between T effector cell activation and T regulatory cell activation. T regulatory cells are responsible for the induction and maintenance of immunological tolerance. These cells are T cells which produce low levels of IL-2, IL-4, IL-5, and IL-12. Regulatory T cells produce TNFα, TGFβ, IFN-γ, and IL-10, albeit at lower levels than effector T cells. Although TGFβ is the predominant cytokine produced by regulatory T cells, this cytokine is produced at lower levels than in Th1 or Th2 cells, e.g., an order of magnitude less than in Th1 or Th2 cells. Regulatory T cells can be found in the CD4+ CD25+ population of cells (see, e.g., Waldmann and Cobbold. 2001 *Immunity* 14:399). Regulatory T cells actively suppress the proliferation and cytokine production of Th1, Th2, or naive T cells which have been stimulated in culture with an activating signal (e.g., antigen and antigen presenting cells or with a signal that mimics antigen in the context of MHC, e.g., anti-CD3 antibody, plus anti-CD28 antibody).

The present disclosure demonstrates that anti-CD200 antibody treatment reduces the number of activated CD4+ and CD8+ T cells following stimulation. Accordingly, the present disclosure relates to methods and compositions for preventing or inhibiting a cellular immune response in a subject in need thereof comprising administering a CD200-binding agent. In certain embodiments, the binding agent is an anti-CD200 antibody or antigen-binding fragment thereof as described herein.

In some embodiments, administration of an anti-CD200 antibody is effective to inhibit T cell activation and/or proliferation or to reduce the number of activated T cells. For example, an anti-CD200 antibody of the present disclosure may be effective to target and/or inhibit activated, CD200-expressing T cells, including Th1 and/or Th2 cells. Accordingly, the methods and compositions of the disclosure may be effective to reduce or deplete activated T cells as well as B cells that would otherwise be activated by Th2 cells (see discussion above). Accordingly, anti-CD200 inhibition of T cells may also result in a reduction of activated B cells and/or circulating immunoglobulin.

While not wishing to be restricted to any particular mode of action, an anti-CD200 antibody may mediate ADCC, CDC, and/or apoptosis of T cells to which the antibody binds, as described elsewhere herein. The antibody may increase the number or function of regulatory T cells. The antibody may be a murine, chimeric, human, humanized, primatized, or de-immunized anti-CD200 antibody or antigen-binding fragment thereof. Optionally, the antibody may elicit increased effector function.

A subject in need of prevention or inhibition of a cellular immune response may be, in certain embodiments, a patient with an autoimmune disorder or a transplant recipient. Accordingly, in certain embodiments the disclosure relates to immunotherapeutic compositions and methods for the treatment or prevention of graft versus host disease (GVHD) and graft rejection in patients, wherein the compositions and methods comprise an anti-CD200 antibody. In particular embodiments, the transplant recipient or patient with an autoimmune disorder is human. In further embodiments, the disclosure relates to methods for treating or preventing an acute or a chronic T cell-mediated rejection in a transplant recipient.

In certain embodiments, an anti-CD200 antibody is used in combination with lower doses of traditional therapeutic agents than would be possible in the absence of the anti-CD200 antibody. In another embodiment, the compositions and methods of the disclosure obviate the need for a more severe form of therapy, such as radiation therapy, high-dose immunomodulatory therapy (such as a high-dose of a therapy that targets T cells), or splenectomy. Combination treatments are discussed in more detail below and include, for example, adriamycin, azathiopurine, busulfan, cyclophosphamide, cyclosporine A, Cytoxan, fludarabine, 5-fluorouracil, methotrexate, mycophenolate mofetil, a nonsteroidal anti-inflammatory, rapamycin, sirolimus, and tacrolimus. Other examples include antibodies such as, e.g., OKT3 (muromonab-CD3), CAMPATH-1G, CAMPATH-1H (alemtuzumab), or CAMPATH-1M, SIMULEC (basiliximab), ZENAPAX (daclizumab), RITUXAN (rituximab), and anti-thymocyte globulin.

Accordingly, in embodiments where an anti-CD200 is administered to a transplant recipient to inhibit a cellular or T cell-mediated immune response, the anti-CD200 antibody may be administered to a transplant recipient prior to or following transplantation, alone or in combination with one or more other therapeutic agents or regimens for the treatment or prevention of GVHD and graft rejection. For example, an anti-CD200 antibody may be used to block or inhibit activation of T cells, to disrupt alloantigen presentation or to expand regulatory T cells.

C. Methods of Depleting or Eliminating Cells Overexpressing CD200

In accordance with the present disclosure, methods are provided for depleting cells that express CD200 in a subject by administering to the subject a therapy comprising a CD200-binding agent. As mentioned above, CD200 is expressed on certain immune cells. The disparate expression of CD200 provides an avenue by which to target activated immune cells (i.e., CD200-positive cells) for therapy. For example, CD200-positive immune cells may be targeted for depletion in methods of treating autoimmune disorders or graft rejection.

As discussed above, CD200, through its interaction with CD200R on myeloid cells, modulates immunosuppression by delivering an inhibitory signal for myeloid activity and/or migration. CD200-knockout mice, for example, demonstrate a more active immune response following immunogenic stimuli (Hoek et al. *Science* 2000, 290:1768-1771), and CD200-expressing cells elicit immunosuppression by inducing a shift in the cytokine profile of stimulated immune cells. Specifically, CD200-positive cells are capable of inducing a shift from Th1 to Th2 cytokine production in mixed cell population assays. While CD200-positive cells are capable of suppressing the immune response, CD200-positive cells, accordingly, may be capable of escaping immune cell attack. However expression of CD200 on the membrane of immune cells can be exploited to target these cells in therapy. For example, an anti-CD200 antibody can specifically target CD200-positive cells and target CD200-positive cells to immune effector cells. The antibody may optionally disrupt the CD200:CD200R interaction. The embodiments of this disclosure, therefore, relate to methods of targeting CD200-positive cells for depletion comprising administering a CD200-binding agent.

In one aspect, the present disclosure relates to methods of modulating ADCC and/or CDC of CD200-positive target cells by administering a murine, chimeric, humanized, or human anti-CD200 antibody or fragment thereof to a subject in need thereof. The disclosure relates to variant anti-CD200 antibodies that elicit increased ADCC and/or CDC and to variant anti-CD200 antibodies that exhibit reduced or no ADCC and/or CDC activity.

IV. Methods of Treating Transplant Patients

The CD200-binding agents and polypeptides and/or antibodies utilized in the present disclosure are especially indicated for therapeutic applications as described herein. Accordingly, CD200-binding agents and anti-CD200 antibodies and variants thereof may be used in therapies, including combination therapies, in the diagnosis and prognosis of disease, as well as in the monitoring of disease progression.

While not wishing to be bound by any particular mechanism(s), an anti-CD200 antibody, antigen-binding fragment, polypeptide, or other CD200-binding agent may promote graft survival by eliminating CD200-positive cells, e.g., by binding to such cells and targeting these cells for immune attack and cell killing. For example, an anti-CD200 antibody or other binding agent may recruit effector cells or other ligands (e.g., complement component) to the CD200-positive cell to which the antibody or binding agent is bound and target the CD200-positive cell for effector-mediated cell death.

In certain aspects, the disclosure relates to methods of treating patients who have received or will receive a transplant (e.g., a xenotransplant or allotransplant) comprising administering a CD200-binding agent. In certain embodiments, the binding agent is an anti-CD200 antibody or antigen-binding fragment thereof. Additionally, the antibody may be a murine, chimeric, humanized, human or de-immunized anti-CD200 antibody. Thus, methods of treating transplant patients may comprise any of the CD200-binding agents and antibodies set forth in the present disclosure.

In certain embodiments, anti-CD200 antibodies or CD200-binding agents may be used for depleting any type of cell that expresses CD200 on its surface, including for example, immune cells such as T-cells, B-cells, and dendritic cells. In one embodiment, anti-CD200 antibodies may be useful for targeted destruction of immune cells involved in an unwanted immune response, such as, for example, immune responses associated with transplant rejection. Exemplary immune responses that may be inhibited or prevented with the anti-CD200 antibodies provided herein include, for example, inflammatory responses (e.g., an anti-CD200 antibody may inhibit the production of inflammatory cytokines such as TNF-α and INF-γ), the production of antibodies specific to alloantigens and/or xenoantigens, and T-cell mediated responses.

In accordance with the methods and compositions described herein, therefore, the disclosure relates to methods of treating an allograft patient. An anti-CD200 antibody or other CD200-binding agent of the present disclosure may be administered to a patient prior to a transplant or allograft procedure or after the procedure in order to decrease or eliminate CD200-positive immune cells that could reduce the patient's acceptance of the transplanted organ, tissue, or cell. In a particular embodiment, an anti-CD200 antibody with increased effector function is given to a transplant patient.

Anti-CD200 antibodies of the present disclosure may be used for inhibiting rejection or promoting survival of a wide range of organ, tissue, and cell grafts as described above. The antibodies may also be used to inhibit graft versus host disease following bone marrow transplantation, for example.

In certain embodiments where the graft recipient is human, an allograft may be MHC mismatched. In certain embodiments, the MHC mismatched allograft is an HLA mismatched allograft. In further embodiments, the recipient is ABO mismatched to the allograft.

Therapies comprising CD200-binding agents or antibodies may be administered to patients in combination therapies. Accordingly, targeted killing of certain populations of immune cells for treating or preventing graft rejection, or for enhancing or extending transplant survival, may be administered as part of a combination therapy. For example, a patient receiving a first therapy comprising a CD200-binding agent (e.g., an anti-CD200 antibody described herein) may also be given a second therapy. The CD200-binding agent may be administered simultaneously with the second therapy. Alternatively, the CD200 antagonist may be administered prior to or following the second therapy. Second therapies include but are not limited to polypeptides, small molecules, chemicals, metals, organometallic compounds, inorganic compounds, nucleic acid molecules, oligonucleotides, aptamers, spiegelmers, antisense nucleic acids, locked nucleic acid (LNA) inhibitors, peptide nucleic acid (PNA) inhibitors, immunomodulatory agents, antigen-binding fragments, prodrugs, and peptidomimetic compounds. In particular embodiments, the second therapy comprises an anti-inflammatory agent, immunosuppressive agent, and/or anti-infective agent.

Combination therapies of the present disclosure include, for example, a CD200-binding agent as described herein (e.g., an anti-CD200 antibody or antigen-binding fragment thereof) administered concurrently or sequentially in series with steroids, anti-malarials, aspirin, non-steroidal anti-inflammatory drugs, immunosuppressants, or cytotoxic drugs. Included are corticosteroids (e.g. prednisone, dexamethasone, and prednisolone), methotrexate, methylprednisolone, macrolide immunosuppressants (e.g. sirolimus and tacrolimus), mitotic inhibitors (e.g. azathioprine, cyclophosphamide, and methotrexate), fungal metabolites that inhibit the activity of T lymphocytes (e.g. cyclosporine), mycophenolate mofetil, glatiramer acetate, and cytotoxic and DNA-damaging agents (e.g. chlorambucil). In certain embodiments, the immunosuppressive agent is selected from among OKT3 (muromonab-CD3), azathioprene, leflunamide, brequinar, ATG, ALG, 15-deoxyspergualin, LF15-0195 (Tesch et al. *Kidney Int.* 2001 60(4):1354-65; Yang et al. *J. Leukocyte Biol.* 2003; 74:438-447), CTLA-4-Ig (belatacept), rituxan, IVIg and bredinin. Anti-inflammatory agents include but are not limited to thalidomide and analogs thereof such as lenalidomide (Revlimid, CC-5013) and CC-4047 (Actimid). For allograft or transplant patients, for example, anti-CD200 therapy may be combined with antibody treatments including daclizumab, a genetically engineered human IgG1 monoclonal antibody that binds specifically to the α-chain of the interleukin-2 receptor, as well as various other antibodies targeting immune cells or other cells (e.g., anti-T cell antibodies). Such combination therapies may be useful in inhibiting immune responses. The disclosure also relates to therapies for transplant patients comprising a CD200-binding agent (such as, for example, the antibodies and variants thereof described in the present disclosure) conjugated to one or more agents.

In certain embodiments, more than one immunosuppressive drug is administered. In other embodiments, an immunomodulatory treatment method, e.g., plasmapheresis, splenectomy or immunoadsorption, is used in combination with an anti-CD200 antibody. Conversely, a combination therapy comprising an anti-CD200 antibody may eliminate the need for such a treatment.

In particular embodiments, an anti-CD200 antibody is administered in conjunction with an inhibitor of cellular immune function. Such inhibitors include but are not limited to cyclosporine A, tacrolimus, rapamycin, anti-T cell antibodies, daclizumab, and muromonab-CD3. As demonstrated in the present disclosure, a combination of an anti-CD200 antibody and an inhibitor of cellular immune function increases survival of a graft compared to the survival observed in a control graft recipient (e.g., a recipient receiving no treatment or a recipient receiving monotherapy, such as an inhibitor of cellular immune function). Increased survival includes, for example, at least about 15%, at least about 20%, at least about 25%, at least about 30%, at least about 40%, or at least about 50% increase in survival time (measured in days, months, or years, for example).

In particular embodiments, a combination treatment comprising an anti-CD200 antibody and a T cell inhibitor leads to long-term survival of allografts. Long-term survival in humans includes, for example, at least about 5 years, at least about 7.5 years, and at least about 10 years survival post-transplant. In certain embodiments, a combination treatment comprising an anti-CD200 antibody or antigen-binding fragment thereof and an inhibitor of T cell activity leads to accommodation of the graft.

While not wishing to be bound by any particular mechanism(s), in such combinations an inhibitor of cellular immune function may inhibit T cell responses and alter cytokine profiles while an anti-CD200 antibody inhibits antibody response and possibly also T cell responses. In particular embodiments, administration of an anti-CD200 antibody allows the successful use of a lower dose of an inhibitor of cellular immune function (e.g., cyclosporine A) than the dose that would otherwise be required to achieve the same or similar level of graft survival.

Accordingly, in certain aspects, the present disclosure relates to methods for enhancing the suppressive effect on graft rejection of existing immunosuppressive agents (cyclosporine, azathioprine, adrenocortical steroids, FK-506, etc.) using CD200-binding agents such as anti-CD200 antibodies and antigen-binding fragments thereof.

Depending on the nature of the combinatory therapy, administration of the anti-CD200 antibody may be continued while the other therapy is being administered and/or thereafter. Administration of the antibody may be made in a single dose, or in multiple doses. In some instances, administration of the anti-CD200 antibody is commenced at least several days prior to the conventional therapy, while in other instances, administration is begun either immediately before or at the time of the administration of the conventional therapy. In some cases, the anti-CD200 antibody will be administered after other therapies, or it could be administered alternating with other therapies.

In certain embodiments, the antibodies of the present disclosure may be used to deliver a variety of cytotoxic compounds. Any cytotoxic compound can be fused to the present antibodies. The fusion can be achieved chemically or genetically (e.g., via expression as a single, fused molecule). The cytotoxic compound can be a biological, such as a polypeptide, or a small molecule. As those skilled in the art will appreciate, for small molecules, chemical fusion is used, while for biological compounds, either chemical or genetic fusion can be employed.

Non-limiting examples of cytotoxic compounds include therapeutic drugs, a compound emitting radiation, molecules of plant, fungal, or bacterial origin, biological proteins, and mixtures thereof. The cytotoxic drugs can be intracellularly acting cytotoxic drugs, such as short-range radiation emitters, including, for example, short-range, high-energy α-emitters. Enzymatically active toxins and fragments thereof are exemplified by diphtheria toxin A fragment, nonbinding active fragments of diphtheria toxin, exotoxin A (from *Pseudomonas aeruginosa*), ricin A chain, abrin A chain, modeccin A chain, alpha-sarcin, certain *Aleurites fordii* proteins, certain Dianthin proteins, *Phytolacca americana* proteins (PAP, PAPII and PAP-S), Morodica charantia inhibitor, curcin, crotin, *Saponaria officinalis* inhibitor, gelonin, mitogillin, restrictocin, phenomycin, and enomycin, for example. Procedures for preparing enzymatically active polypeptides of the immunotoxins are described in WO85/03508, which is hereby incorporated by reference. Certain cytotoxic moieties are derived from adriamycin, chlorambucil, daunomycin, methotrexate, neocarzinostatin, and platinum, for example.

Procedures for conjugating the antibodies with the cytotoxic agents have been previously described and are within the purview of one skilled in the art.

In another embodiment in accordance with the present disclosure, methods are provided for monitoring the progress and/or effectiveness of a therapeutic treatment. The method involves administering an immunomodulatory therapy and determining CD200 levels in a subject at least twice to determine the effectiveness of the therapy. For example, pre-treatment levels of CD200 can be ascertained and, after at least one administration of the therapy, levels of CD200 can again be determined. A decrease in CD200 levels is indicative of an effective treatment. Measurement of CD200 levels can be used by the practitioner as a guide for increasing dosage amount or frequency of the therapy. It should of course be understood that CD200 levels can be directly monitored or, alternatively, any marker that correlates with CD200 can be monitored.

V. Modes of Administration and Formulations

The route of antibody administration of the antibodies of the present disclosure (whether the pure antibody, a labeled antibody, an antibody fused to a toxin, etc.) is in accord with known methods, e.g., injection or infusion by intravenous, intraperitoneal, intracerebral, intramuscular, subcutaneous, intraocular, intraarterial, intrathecal, inhalation or intralesional routes, or by sustained release systems. The antibody is preferably administered continuously by infusion or by bolus injection. One may administer the antibodies in a local or systemic manner.

The present antibodies may be prepared in a mixture with a pharmaceutically acceptable carrier. Techniques for formulation and administration of the compounds of the instant application may be found in "Remington's Pharmaceutical Sciences," Mack Publishing Co., Easton, Pa., latest edition. This therapeutic composition can be administered intravenously or through the nose or lung, preferably as a liquid or powder aerosol (lyophilized). The composition may also be administered parenterally or subcutaneously as desired. When administered systemically, the therapeutic composition should be sterile, substantially pyrogen-free and in a parenterally acceptable solution having due regard for pH, isotonicity, and stability. For example, a pharmaceutical preparation is substantially free of pyrogenic materials so as to be suitable for administration as a human therapeutic. These conditions are known to those skilled in the art.

According to the compositions and methods set forth in the present embodiments, the disclosure relates to any pharmaceutical composition comprising an anti-CD200 antibody. Included are chimeric, humanized, human and de-immunized anti-CD200 antibodies and antigen-binding fragments, including single-chain antibodies. Also included are murine, chimeric, humanized, human and de-immunized variant anti-CD200 antibodies and antigen-binding fragments with altered effector function(s) as described herein. Pharmaceutical compositions of the disclosure may further comprise one or more immunomodulatory or immunosuppressive agents, such as an inhibitor of T cell function.

Pharmaceutical compositions suitable for use include compositions wherein one or more of the present antibodies are contained in an amount effective to achieve their intended purpose. More specifically, a therapeutically effective amount means an amount of antibody effective to prevent, alleviate or ameliorate symptoms of disease or prolong the survival of the subject being treated or to prolong the survival of the grafted organ, tissue or cells. Determination of a therapeutically effective amount is well within the capability of those skilled in the art, especially in light of the detailed disclosure provided herein. Therapeutically effective dosages may be determined by using in vitro and in vivo methods.

In certain aspects, the disclosure provides the use of a CD200-binding agent and an immunomodulatory or immunosuppressive agent in the manufacture of a medicament or medicament package for prolonging survival of or inhibiting disease in a subject in need thereof (e.g., a graft recipient). In certain embodiments, more than one immunosuppressive agent is included in the medicament or medicament package. In certain embodiments, the binding agent (e.g., an anti-CD200 antibody or fragment thereof) and the immunomodulatory or immunosuppressive agent are in a formulation suitable for concurrent administration to the subject in need thereof. In certain embodiments, the binding agent (e.g., an anti-CD200 antibody or fragment thereof) and the immunomodulatory or immunosuppressive agent are in a formulation or formulations suitable for sequential administration to the subject in need thereof. In certain embodiments, an anti- CD200 antibody or antigen-binding fragment thereof is in a formulation suitable for chronic administration to the subject in need thereof. In certain embodiments, the immunomodulatory or immunosuppressive agent is in a formulation suitable for chronic administration to a subject in need thereof, such as a graft recipient.

In certain embodiments, a CD200-binding agent is an antibody in a lyophilized formulation comprising the antibody and a lyoprotectant. In certain embodiments, an immunomodulatory or immunosuppressive agent of the disclosure is in a lyophilized formulation comprising the immunosuppressive agent and a lyoprotectant. In certain embodiments, the antibody and immunosuppressive agent are in the same lyophilized formulation comprising said antibody, said immunosuppressive drug, and a lyoprotectant. In certain embodiments, a CD200-binding agent such as an anti-CD200 antibody is in an injection system comprising a syringe that comprises a cartridge, wherein the cartridge contains the antibody in a formulation suitable for injection. In certain embodiments, an immunomodulatory or immunosuppressive agent is in an injection system comprising a syringe that comprises a cartridge, wherein the cartridge contains the immunomodulatory or immunosuppressive agent in a formulation suitable for injection. In certain embodiments, an anti-CD200 antibody and an immunomodulatory or immunosuppressive agent are in an injection system comprising a syringe that comprises a cartridge, wherein said cartridge contains the antibody and the immunomodulatory or immunosuppressive agent in a formulation suitable for injection. The antibody and or the immunomodulatory or immunosuppressive agent may be in unit dosage form(s). Accordingly, the present disclosure provides methods of inhibiting immune responses, including humoral and cellular responses, and methods of inhibiting graft rejection, or of prolonging survival of transplanted cells, tissues or organs. In particular, methods of prolonging survival of allotransplanted cells, tissues or organs are provided. These methods are directed to using a CD200-binding agent, such as an anti-CD200 antibody, optionally in combination with one or more immunosuppressants and/or immunosuppressive methods. The disclosure also provides use of a CD200-binding agent, such as an anti-CD200 antibody, optionally with one or more immunosuppressants, in the manufacture of one or more medicaments or medicament packages. Such medicaments or medicament packages are useful in inhibiting immune responses, such as in a patient with an autoimmune disorder or in a transplant recipient.

VI. Exemplification

EXAMPLE 1

T Cell Killing by Antibody hB7V3V2

To evaluate whether incubation of activated T cells with anti-CD200 antibodies containing a constant region mediating effector function (e.g. an IgG1 constant region) results in the killing of the T cells, T cells were activated and killing assays were set up as described below.

A. CD3+ T Cell Isolation

Human peripheral blood lymphocytes (PBLs) were obtained from normal healthy volunteers by density gradient centrifugation of heparinized whole blood using the Accuspin™ System. Fifteen mL of Histopaque-1077 (Sigma, St. Louis, Mo.; cat# H8889) was added to each Accuspin tube (Sigma, St. Louis, Mo.; cat#A2055) which was then centrifuged at 1500 rpm for 2 minutes so that the Histopaque was allowed to pass through the frit. Thirty mL of whole blood was layered over the frit and the tubes were centrifuged for 15 minutes at 2000 rpm at room temperature with no brake. The PBL interface was collected and mononuclear cells were washed twice in PBS with 2% heat-inactivated fetal bovine serum (FBS) (Atlas Biologicals, Ft. Collins, Colo.; cat# F-0500-D) with 1200 rpm centrifugation for 10 minutes. CD3+ T cells were isolated by passage over a HTCC-5 column (R&D Systems) according to the manufacturer's instructions. Eluted cells were washed, counted and resuspended in RPMI 1640 containing 5% heat-inactivated single donor serum, 2 mM L-glutamine, 10 mM Hepes and penicillin/streptomycin.

B. Activation with Plate-Bound mOKT3

Wells of 12-well plates (Falcon) were coated by overnight incubation at 4° C. with 10 μg/mL mOKT3 (Orthoclone) diluted in PBS. Residual antibody was removed and the plates gently rinsed with PBS. Purified CD3+ T cells, isolated as described above, were added to the plates at a final concentration of $2\times10^6$/well in RPMI 1640 containing 5% heat-inactivated single donor serum, 2 mM L-glutamine, 10 mM Hepes and penicillin/streptomycin. Cells were maintained for 72 hours at 37° C. in a humidified incubator containing 5% $CO_2$.

C. $^{51}$Chromium Labeling of mOKT3-Activated CD3+ Target Cells

At the end of the culture period, mOKT3-activated CD3+ cells were harvested, washed and resuspended at $10^7$ cells/mL in RPMI 1640 without serum. Cells were chromated by the addition of 125 μCi of $^{51}$Chromium (Perkin Elmer, Billerica, Mass.)/$10^6$ cells for 2 hours at 37° C. Labeled cells were harvested, washed in RPMI containing 5% heat-inactivated single donor serum and resuspended at a final concentration of $2\times10^5$ cells/mL in the same medium.

D. Preparation of Autologous NK Effector Cells

Human peripheral blood lymphocytes (PBLs) from the same individual were obtained as described above by density gradient centrifugation. The PBL interface was collected and mononuclear cells were washed twice in PBS with 2% heat-inactivated fetal bovine serum (FBS) (Atlas Biologicals, Ft. Collins, Colo.; cat# F-0500-D) with 1200 rpm centrifugation for 10 minutes. CD56+ cells were isolated by positive selection over anti-CD56-conjugated magnetic beads (Miltenyi Biotec, Auburn, Calif., Cat #120-000-307) according to the manufacturer's instructions. Eluted cells were washed, counted and resuspended at $1.3\times10^6$ cells/mL in RPMI 1640 containing 5% heat-inactivated single donor serum, 2 mM L-glutamine, 10 mM Hepes and penicillin/streptomycin. Cells were incubated overnight at 37° C. in a humidified incubator containing 5% $CO_2$ at a final concentration of $4\times10^6$ cells/well in 3 mL of the same medium. At the end of the culture period, the cells were harvested, washed, counted and resuspended in serum-free RPMI containing 2 mM L-glutamine, 10 mM Hepes, $2\times10^{-5}$ M 2-mercaptoethanol and penicillin/streptomycin.

E. ADCC Assay $^{51}$Cr-labelled mOKT3-activated CD3+ target cells prepared as described above were distributed in wells of a 96-well plate at $10^4$ cells/well in 50 μL. CD56+ effector cells were harvested, washed, counted and resuspended at either $2.5\times10^6$ cells/mL (for an effector:target cell ratio of 25:1) or $10^6$ cells/mL (for an effector:target cell ratio of 10:1) and were distributed (100 μL/well) to wells containing the target cells. Ten-fold dilutions of anti-CD200 antibodies (V3V2-G1 or V3V2-G2/G4) were added to the effectors and targets at final concentrations of 10, 1, 0.1 and 0.01 μg/mL. Assay controls included the following: 1) effectors and targets in the absence of antibody (0 Ab); 2) target cells in the absence of effectors (spontaneous lysis) and 3) effectors and targets incubated with 0.2% Tween-80 (maximum release). All cell culture conditions were performed in triplicate. Cells were incubated at 37° C. for 4 hours in a humidified incubator containing 5% $CO_2$. At the end of the culture period, the plates were centrifuged to pellet the cells and 150 µL of cell supernatant was transferred to scintillation vials and counted in a gamma scintillation counter (Wallac). The results are expressed as percent specific lysis according to the following formula:

(Mean sample counts per minute (cpm)–mean spontaneous lysis)×100 (mean maximum lysis-mean spontaneous lysis)

F. Flow Cytometry

One hundred µL it of cell suspensions (mOKT3-activated CD3+ cells or purified CD56+ NK cells) prepared as described above were distributed to wells of a 96-well round bottom plate (Falcon, Franklin Lakes N.J.; cat#353077). Cells were incubated for 30 minutes at 4° C. with the indicated combinations of the following fluorescein isothiocyanate (FITC)-, Phycoerythrin (PE)-, PerCP-Cy5.5-, or allophycocyanin (APC)-conjugated antibodies (all from Becton-Dickinson, San Jose, Calif.); anti-human CD25-FITC (cat#555431); anti-human CD3-APC (cat#555335); anti-human CD200-PE (cat #552475); anti-human CD8-PerCP-Cy5.5 (cat#341051); anti-human CD4-APC (cat#555349); anti-human CD5-APC (cat#555355) and anti-human CD56-APC (cat#341025). Isotype controls for each labeled antibody were also included. After washing cells twice with FACS buffer (1800 rpm centrifugation for 3 minutes), cells were resuspended in 300 µL of PBS (Mediatech, Herndon, Va.; cat#21-031-CV) and analyzed by flow cytometry using a FACSCalibur machine and CellQuest Software (Becton Dickinson, San Jose, Calif.).

As shown in FIG. 5, activated T cells show high CD200 expression on their surface. Activated T cells are efficiently killed in the presence of hB7V3V2-G1 but not hB7V3V2-hG2G4 when NK cells are used as effector cells (FIG. 6). These data demonstrate that anti-CD200 antibodies with effector function can eliminate activated T cells. Such an antibody can be of therapeutic use in the transplantation setting or for the treatment of autoimmune diseases.

In addition to regulatory T cells, plasmacytoid dendritic cells have been shown to play a negative immunoregulatory role in human cancer (Wei S, et al., *Cancer Res.* 2005 Jun. 15; 65(12):5020-6). Combination of a therapy eliminating plasmacytoid dendritic cells with anti-CD200 therapy can therefore be advantageous.

EXAMPLE 2

Anti-CD200 mAb Prevents Acute Allograft Rejection in a Mouse Cardiac Transplantation Model The calcineurin inhibitors, such as cyclosporine A (CsA) and tacrolimus, are known to have narrow therapeutic ranges. Even at therapeutic doses, these drugs carry a considerable risk for nephrotoxicity (Seron, D., and F. Moreso. 2004, *Transplant Proc* 36:257 S). Treatment with subtherapeutic levels of either CsA or tacrolimus results in significantly lower incidence of nephrotoxicity but at the same time shows marked graft rejection (Seron, D., and F. Moreso. 2004. *Transplant Proc* 36:257 S; Dunn et al., 2001, *Drugs* 61:1957; Scott et al. 2003 *Drugs* 63:1247). The limitations and side effects of current therapy regimens indicate that it is of value to search for novel drugs that reduce the requirement of CsA and have synergy with low dose CsA to prevent acute rejection and prolong graft survival.

The present study examined graft survival in a C57BL/6-to-BALB/c fully MHC-mismatched mouse heart transplantation model. Each experimental group consisted of five animals. Treatments were administered as follows:
Anti-CD200 mAb: 100 µg/mouse/day, days 0-14, i.p.
Rapamycin (Rapa): 2 mg/kg/day, days 0-13, orally
Cyclosporine A (CsA):
 Low dose/long-term treatment: 5 mg/kg/day, days 0-endpoint, s.c.
 High dose/long-term treatment: 15 mg/kg/day, days 0-endpoint, s.c.
 High dose/short-term treatment: 15 mg/kg/day, days 0-28, s.c.

Figure 11:
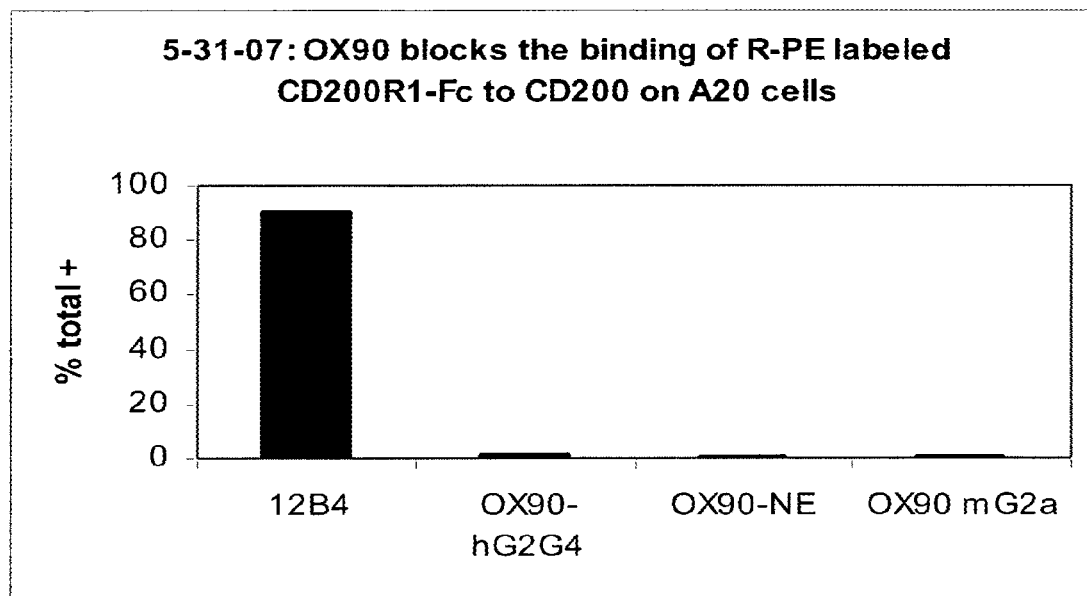
FIG. 11 shows that the OX90 antibodies are blocking antibodies in that they block the binding of CD200 to the CD200R1 receptor.

The anti-CD200 mAb used was OX90mG2a, a chimeric antibody derived from OX90, a rat anti-mouse CD200 mAb obtained as a hybridoma from the European Collection of Cell Cultures (ECACC No. 03062502; see Hoek et al., Science 290:1768-1771 (2000)). The rat antibody was genetically modified to contain the rat heavy chain variable regions fused to a murine IgG2a constant region and the rat light chain variable region fused to a murine kappa constant region. The antibody used to obtain the data for Table 1 was obtained from a different antibody preparation than the preparation from which the antibody in Table 2 was obtained. Table 2 additionally includes data using an antibody called OX90NE. Antibody OX90NE is a rat anti-mouse CD200 antibody that has been engineered to have decreased effector function. This was accomplished by mutating four amino acid residues of OX90mG2a heavy chain (the light chains are identical). The sequences of OX90mG2a and OX90NE are shown in FIG. 10. The various OX90 antibodies are blocking antibodies, as shown in FIG. 11. Cells of the A20 line, which express high levels of murine CD200, were incubated with 20 µg/mL 12B4 (control) or OX90 variant antibodies for 30 minutes at 4° C. Cells were washed and incubated with 10 µg/mL CD200R1-Fc conjugated with R-PE (Invitrogen/molecular probes, catalog Z 25155) for 30 minutes at 4° C. Binding was analyzed by flow cytometry. As shown, OX90hG2G4, OX90NE and OX90mG2a efficiently block the binding of R-PE labeled CD200R1-Fc to CD200 on A20 cells, whereas the control antibody 12B4 does not block binding.

Graft Histology

At necropsy, heart tissue samples were fixed in 10% buffered formaldehyde, embedded in paraffin and sectioned for hematoxylin and eosin (H&E) staining. The microscopic sections were examined in a blinded fashion for severity of rejection by a pathologist (B.G.). Criteria for graft rejection included the presence of vasculitis, thrombosis, hemorrhage and lymphocyte infiltration and were scored as: 0, no change; 1, minimum change; 2, mild change; 3, moderate change; or 4, marked change compared to normal tissues.

Immunohistochemistry

Four micrometer sections were cut from cardiac frozen tissue samples embedded in Tissue-Tek Optimum Cutting Temperature (O.C.T.) gel (Skura Finetek, Torrance, Calif.), mounted on gelatin-coated glass microscope slides and stained by a standard indirect avidin-biotin immunoperoxidase method using an Elite Vectastain ABC kit (Vector Laboratories Inc., Burlingame, Calif.). Specimens were evaluated for the presence of $CD4^+$ and $CD8^+$ T cells using a biotin-conjugated rat anti-mouse CD4 mAb (clone YTS 191.1.2, Cedarlane Laboratories Ltd., Hornby, Ontario, Canada) and a biotin-conjugated rat anti-mouse CD8 mAb (clone 53-6.7, BD Biosciences, Franklin Lakes, N.J.), respectively. Intragraft monocyte/macrophage infiltration was detected with a biotin-conjugated rat anti-mouse Mac-1 mAb (Cedarlane). Mouse IgG and IgM deposition was detected in grafts using biotin-conjugated goat anti-mouse-IgG and goat anti-mouse-IgM, respectively (Cedarlane). For identification of complement deposition, tissue sections were sequentially incubated with polyclonal goat anti-mouse C3 or anti-mouse C5 sera (Quidel, San Diego, Calif.), biotinylated rabbit anti-goat IgG (Vector Laboratories), and HRP-conjugated-streptavidin (Zymed Laboratories, South San Francisco, Calif.). Slides were washed with phosphate-buffered saline (PBS) between the antibody incubation steps and examined under light microscopy. Negative controls were performed by omitting the primary antibodies. Antibody reactivity was evaluated in five high-powered fields of each section using tissue samples from five animals per treatment group. The intensity of staining was graded from 0 to 4+ according to the following: 0, negative; 1+, equivocal; 2+, weak; 3+, moderate and 4+, intensive staining.

TABLE 1

Experimental Groups and Survival Data

| Treatment | Individual survival (days) | MST ± SD (days) |
|---|---|---|
| 1) Untreated | 8, 8, 9, 9 (Historical data) | 8.5 ± 0.6 |
| 2) CsA (Low dose/long-term) | 9, 10, 10, 10, 11, 11 (Historical data) | 10.1 ± 0.3 |
| 3) CsA (High dose/long-term) | 15, 16, 16, 17 (Historical data) | 16 ± 0.8 |
| 4) OX90mG2a | 8, 9, 9, 9, 10, 11 | 9 |
| 5) OX90mG2a + CsA (High dose/long-term) | >100 × 4 | >100 |
| 6) OX90mG2a + CsA (High dose/short-term) | 56 (B), 71 (B), 75 (B) | 71 |
| 7) OX90mG2a + CsA (Low dose/long-term) | 53, 54, 54, >76 (A), >76 (A), >81 (A-), >81 (A-) | >76 |
| 8) OX90mG2a + Rapa | >100 × 6 | >100 |

* The degree of pulsation is scored as: A, beating strongly; B, mild decline in the intensity of pulsation; C, noticeable decline in the intensity of pulsation; or D, complete cessation of cardiac impulses.
MST = Mean Survival Time;
SD = Standard Deviation.

TABLE 2

Heart Graft Survival:

| Groups | Individual Survival* | Median Survival (days) |
|---|---|---|
| 1) OX90mG2a | 9, 10, 10, 11 | 10 |
| 2) OX90mG2a + CsA (Low dose/long-term) | 13#, 13#, 14#, 31#, 40**, 75, 78 | 75 |
| 3) OX-90NE + CsA (Low dose/long-term) | 14#, 16#, 39, 39, 64, 67, 68 | 64 |
| 4) Isotype control (12B4) + CsA (Low dose/long-term) | 12, 12, 13, 14 | 12.5 |

*The degree of pulsation is scored as: A, beating strongly; B, mild decline in the intensity of pulsation; C, noticeable decline in the intensity of pulsation; or D, complete cessation of cardiac impulses.
**Animal died with strong beating of heart graft
As mentioned above, unexpected early rejection may be due to a possible problem with this batch of antibody.

The heart grafts in the Isotype control (12B4) group were rejected rapidly. Further, no difference was observed in the survival time between Isotype control (12B4)+CsA group and CsA monotherapy group. The data in Tables 1 and 2 demonstrate that anti-CD200 therapy has a strong effect in prolonging survival. This was seen both with an antibody having effector function and an antibody lacking effector function.

TABLE 3

Median scores of histological changes of heart allografts at necropsy (study endpoint or at time of rejection)*

| Groups | Vasc | Infar | Lymph | Throm | Hemo |
|---|---|---|---|---|---|
| 1) Untreated (POD8/endpoint) | 3.0 | 3.0 | 3.0 | 4.0 | 3.0 |
| 2) CsA (High dose/long-term, POD16/endpoint) | 2.0 | 1.0 | 2.0 | 3.0 | 2.0 |
| 3) CsA (low dose/short-term) | 3.0 | 2.0 | 2.0 | 4.0 | 2.0 |
| 4) OX90mG2a (POD9/endpoint) | 2.0 | 1.0 | 2.0 | 3.0 | 2.0 |
| 5) OX90mG2a + CsA (High dose/long-term, POD100) | 0.0 | 1.0 | 1.0 | 1.0 | 0.0 |
| 6) OX90mG2a + (High dose/short-term) | 2.0 | 0.0 | 2.0 | 0.0 | 1.0 |
| 7) OX90mG2a + CsA (Low dose/long-term) | 1.0 | 1.0 | 2.0 | 1.0 | 1.0 |
| 8) OX90NE+ CsA (Low dose/long-term) | 2.0 | 1.0 | 2.0 | 1.0 | 2.0 |
| 9) Isotype control (12B4) + CsA (Low dose/long-term) | 2.0 | 2.0 | 2.0 | 3.0 | 2.0 |

*Median scores: 0—normal; 1—minimal change; 2—mild change; 3—moderate change; 4—marked change.
POD = Post Operative Day.

Figure 7A:
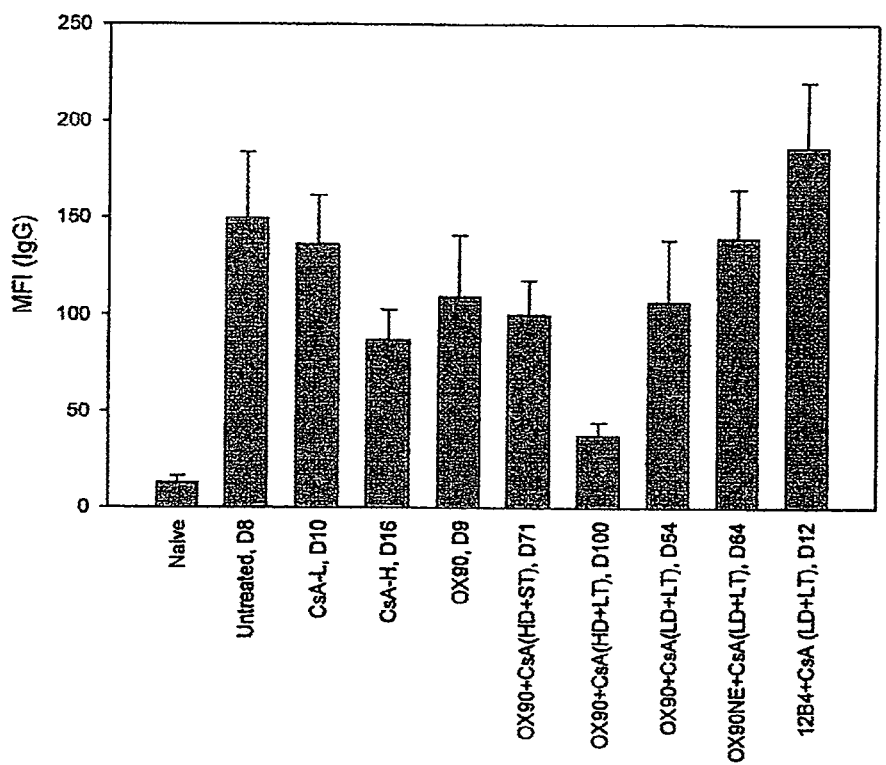
FIGS. 7A-B demonstrate that an anti-CD200 antibody administered in combination with an inhibitor of T cells (cyclosporine A) leads to a signification reduction in antibody production, or an inhibition of a humoral immune response, in a murine heart allograft model.
Figure 7B:
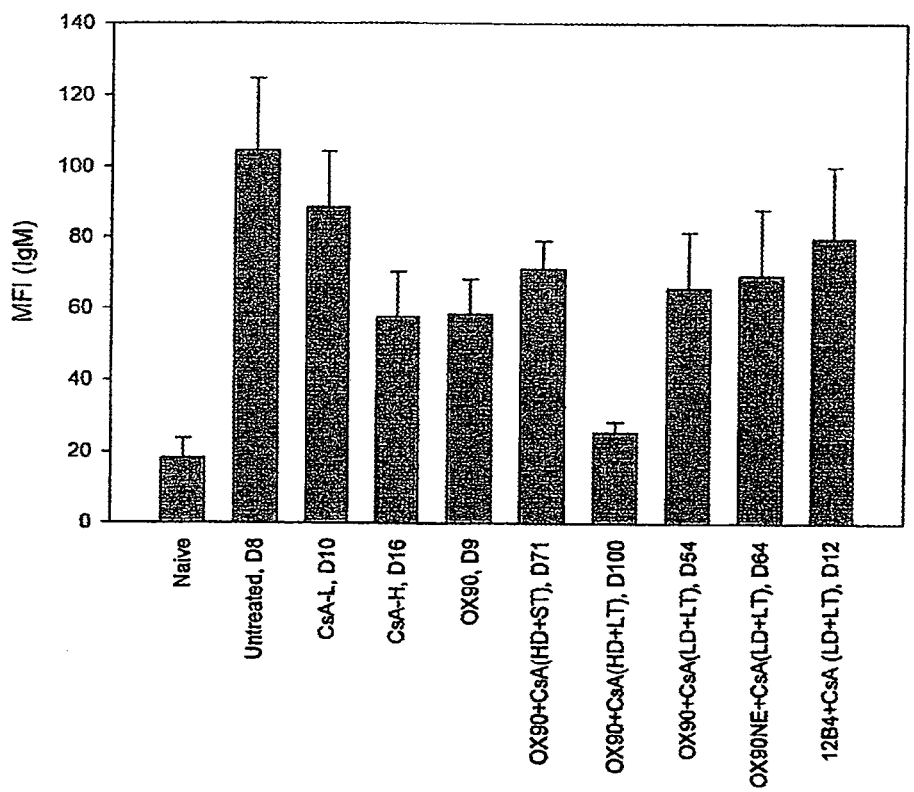
Figure 8:
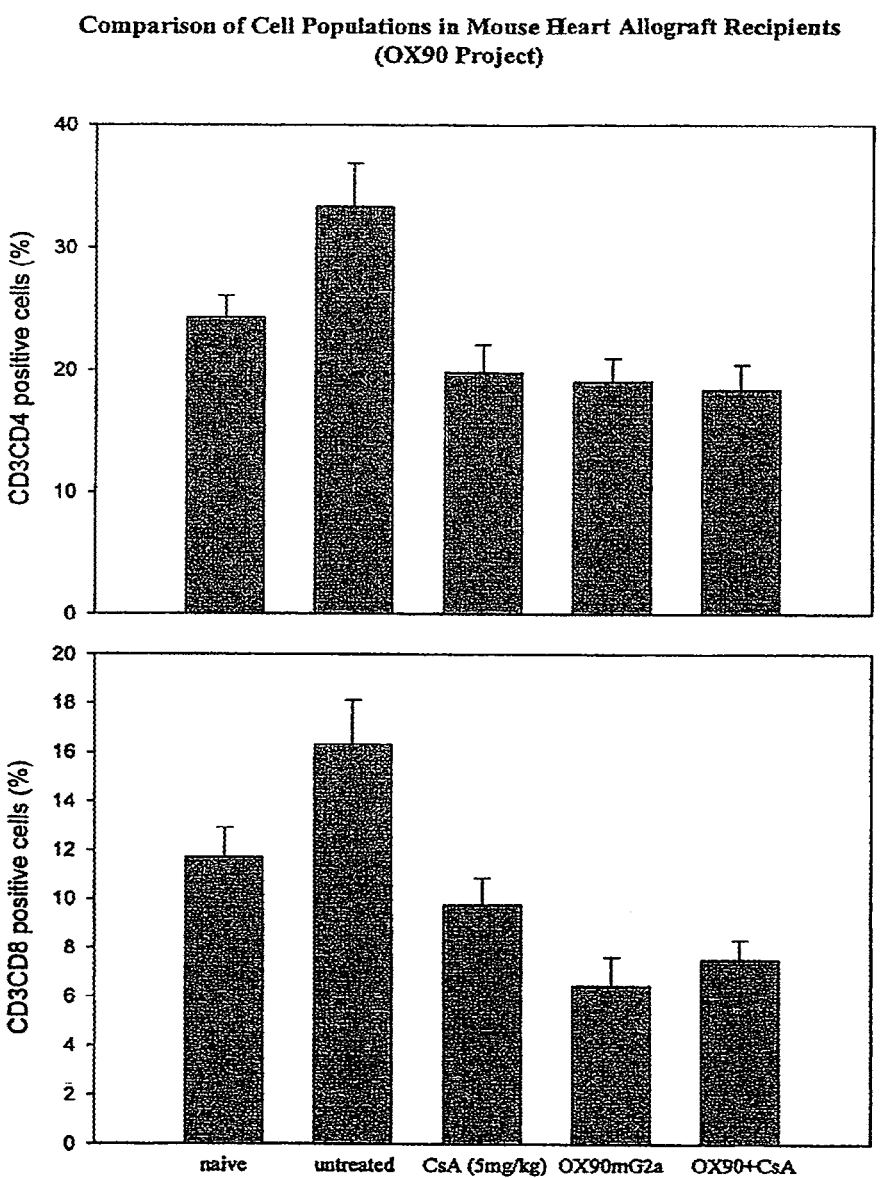
FIG. 8 indicates the levels of splenic CD4+ and CD8+ T cells in mouse heart allograft recipients following various immunomodulatory treatments, including an anti-CD200 antibody and cyclosporine A. Splenic cells from graft recipients were analyzed by flow cytometry.

In addition to survival and graft survival, circulating anti-donor antibody levels and the number of T cell populations in the spleen were measured by flow cytometry. Anti-CD200 mAb in combination with a high dose of CsA inhibits anti-donor antibody production in long-term surviving recipients (FIGS. 7A and 7B). Further, anti-CD200 mAb in combination with a high dose of CsA significantly downregulates splenic CD4+ and CD8+ T cell populations in long-term surviving recipients (FIG. 8).

Figure 9A:
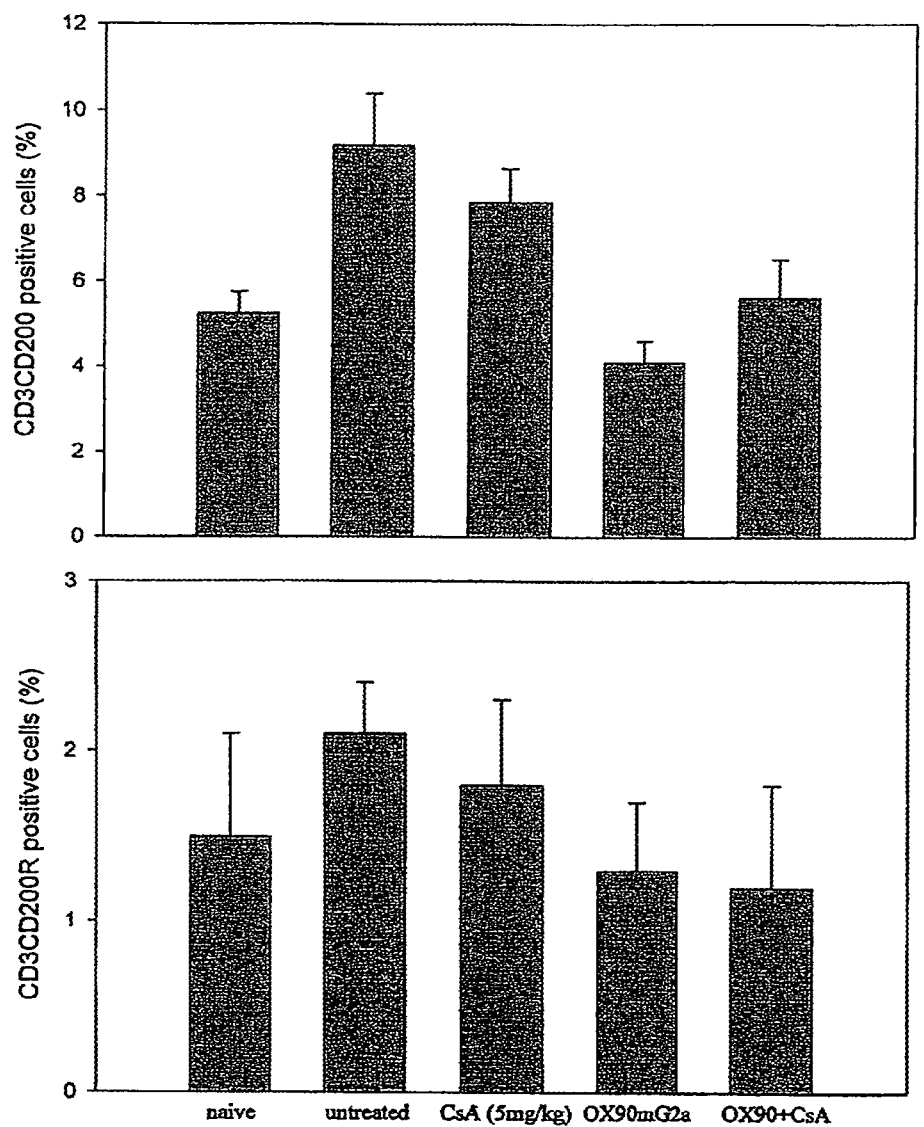
FIGS. 9A-C provide the levels of CD3CD200; CD3CD200R, CD19CD200, CD19CD200R, CD11cCD200, and CD11cCD200R positive cells in mouse heart allograft recipients following treatment with an anti-CD200 antibody and cyclosporine A.
Figure 9B:
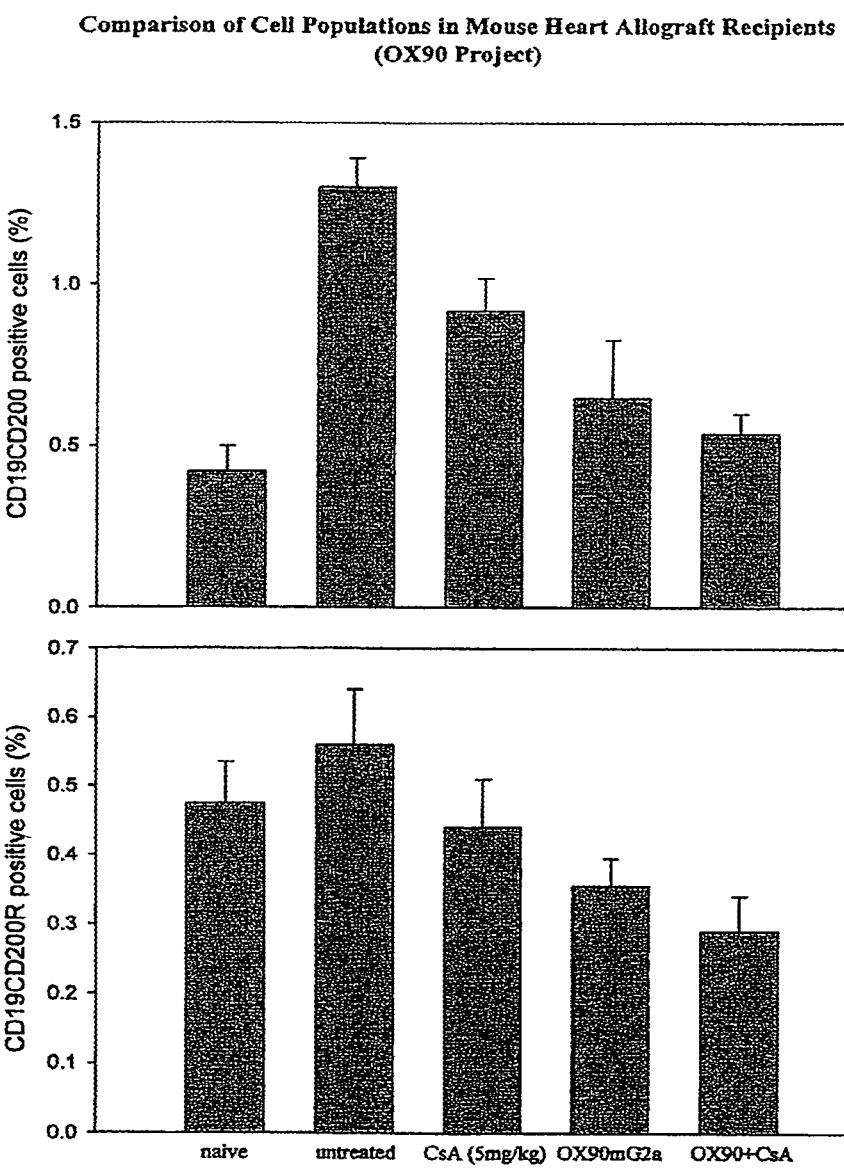
Figure 9C:
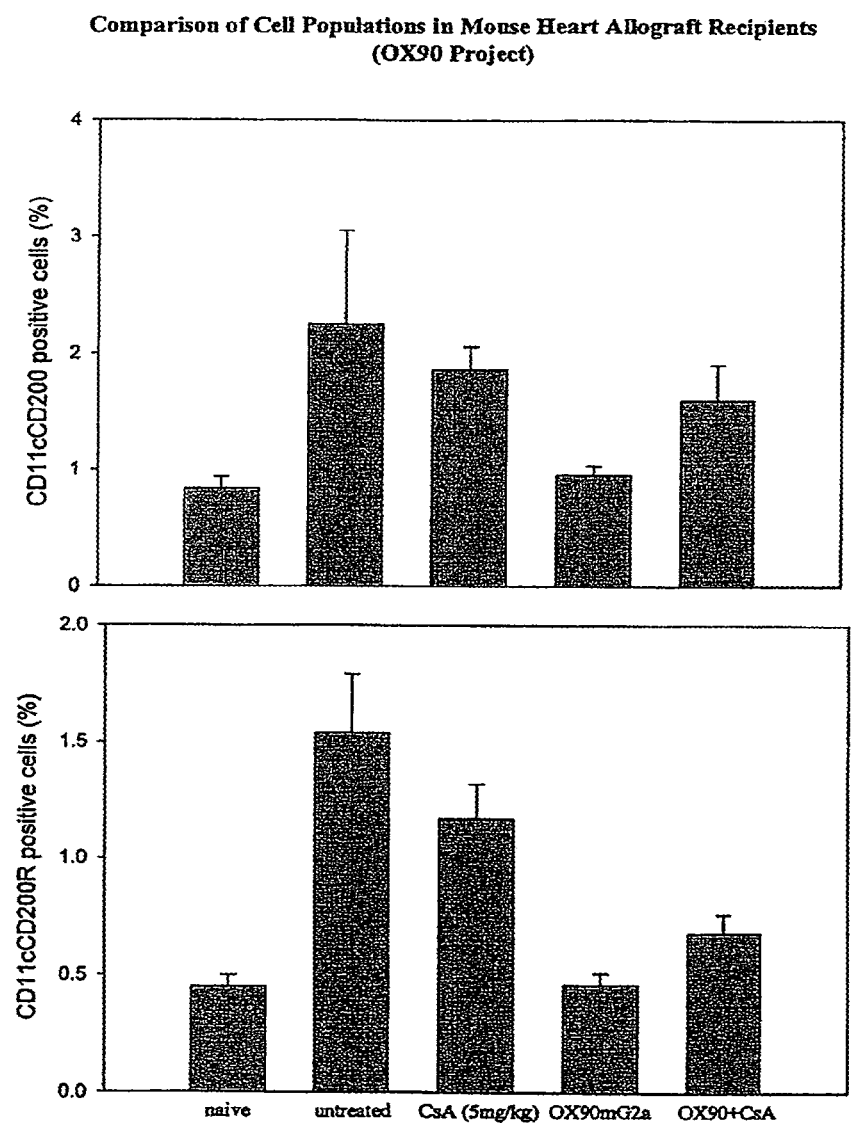

Additionally, the following cell populations were measured by flow cytometry: CD3 CD200; CD3 CD200R; CD19CD200; CD19CD200R; CD11 cCD200; and CD11cCD200R. These results are shown in FIGS. 9A-C.

Intragraft deposition of IgG, IgM, C3 and C5 and other intragraft cellular markers (such as CD4, CD8, and Mac-1) were measured in frozen graft sections. The results are shown in Tables 4-6.

TABLE 4

Intragraft Deposition of Humoral Markers Detected by Immunohistochemistry
Frozen sections of the grafts were collected and stained (for the sacrificed animals only)

| Groups (Treatment) | IgG | IgM | C3 | C5 |
|---|---|---|---|---|
| 1) Untreated | 4+ | 2+ | 3+ | 3+ |
| 2) CsA (High dose/long-term) | 3+ | 2+ | 3+ | 3+ |
| 3) CsA (Low dose/long-term) | 3+ | 2+ | 3+ | 3+ |
| 4) OX90mG2a | 2+ | 2+ | 3+ | 3+ |
| 5) OX90mG2a + CsA (High dose/long-term, POD 100) | 1+ | 1+ | 3+ | 2.5+ |
| 6) OX90mG2a + CsA (High dose/short-term) | 2+ | 2+ | 3+ | 3+ |
| 7) OX90mG2a + CsA (Low dose/long-term) | 2+ | 2+ | 3+ | 3+ |

TABLE 4-continued

Intragraft Deposition of Humoral Markers Detected by
Immunohistochemistry
Frozen sections of the grafts were collected and stained (for the sacrificed
animals only)

| Groups (Treatment) | IgG | IgM | C3 | C5 |
|---|---|---|---|---|
| 8) OX90NE + CsA (Low dose/long-term) | 2+ | 2+ | 3+ | 3+ |
| 9) Isotype control (12B4) + CsA (Low dose/long-term) | 2+ | 2+ | 3+ | 3+ |

Staining intensity grades: 0 is negative, 1+ is equivocal, 2+ is weak, 3+ is moderate, and 4+ is intense.

TABLE 5

Intragraft Cellular Markers Measured by Immunohistochemistry
Frozen sections of the grafts were collected and stained (for the sacrificed
animals only)

| Groups (Treatment) | CD4 | CD8 | Mac |
|---|---|---|---|
| 1) Untreated | 3+ | 2+ | 3+ |
| 2) CsA (High dose/long-term) | 2+ | 2+ | 3+ |
| 3) CsA (Low dose/long-term) | 2+ | 2+ | 3+ |
| 4) OX90mG2a | 2+ | 1+ | 3+ |
| 5) OX90mG2a + CsA (High dose/long-term, POD 100) | 1+ | 1+ | 1+ |
| 6) OX90mG2a + CsA (High dose/short-term) | 2+ | 2+ | 2+ |
| 7) OX90mG2a + CsA (Low dose/long-term) | 2+ | 1+ | 2+ |
| 8) OX90NE + CsA (Low dose/long-term) | 2+ | 2+ | 3+ |
| 9) Isotype control (12B4) + CsA (Low dose/long-term) | 2+ | 2+ | 3+ |

Staining intensity grades: 0 is negative, 1+ is equivocal, 2+ is weak, 3+ is moderate, and 4+ is intense.

TABLE 6

Intragraft CD200 and CD200R Deposition Measured by
Immunohistochemistry
Frozen sections of the grafts were collected and stained (for the sacrificed
animals only).

| Groups (Treatment) | CD200 | CD200R |
|---|---|---|
| 1) Untreated | 3+ | 2+ |
| 2) CsA (High dose/long-term) | 3+ | 2+ |
| 3) CsA (Low dose/long-term) | 3+ | 2+ |
| 4) OX90mG2a | 2+ | 1+ |
| 5) OX90mG2a + CsA (High dose/long-term, POD 100) | 2+ | 1+ |
| 6) OX90mG2a + CsA (High dose/short-term) | 2+ | 1+ |
| 7) OX90mG2a + CsA (Low dose/long-term) | 2+ | 1+ |
| 8) OX90NE + CsA (Low dose/long-term) | 2+ | 1+ |
| 9) Isotype control (12B4) + CsA (Low dose/long-term) | 3+ | 2+ |

Staining intensity grades: 0 is negative, 1+ is equivocal, 2+ is weak, 3+ is moderate, and 4+ is intense.

The data above demonstrate that an anti-CD200 mAb in combination with CsA significantly prolongs heart allograft survival in a mouse cardiac transplantation model. Importantly, anti-CD200 mAb significantly reduces the requirement of CsA in achieving long-term allograft acceptance.

EXAMPLE 3

Effect of Anti-CD200 mAb, OX90NE-AG, in Prevention of Acute Allograft Rejection

The OX90NE antibody described above was originally thought to lack effector function, however, it was later found that OX90NE still retained some effector function and thus further experiments were performed with a different antibody, OX90NE-AG that lacks effector function. The OX90NE-AG antibody is similar to the OX90NE antibody but includes one additional mutation which replaces the Asn 298 residue with Gln. The AG designates that the antibody is aglycosylated (the Asn298 can be glycosylated but the Gln298 cannot be glycosylated); the resulting antibody cannot mediate ADCC or CDC.

Similar to the experiments described above, the present study examined graft survival in a C57BL/6-to-BALB/c fully MHC-mismatched mouse heart transplantation model. Each experimental group consisted of five animals. Treatments were administered as follows:

OX90NE-AG: 100 μg/mouse/day, days 0-14, i.p.
Cyclosporine A (CsA): 15 mg/kg/day, days O-endpoint, s.c.

The results are shown below in Table 7.

TABLE 7

Experimental groups and survival results

| Groups | Individual survival days* |
|---|---|
| CsA + OX90NE-AG variant (Sacrificed on POD16) | 16 (A) × 5 |
| CsA + OX90NE-AG variant (to be sacrificed on POD100) High dose/long-term treatment | >90 (A), >90 (A), >90 (A), >90 (A), >90 (A) |

*The degree of pulsation is scored as: A, beating strongly; B, mild decline in the intensity of pulsation; C, noticeable decline in the intensity of pulsation; or D, complete cessation of cardiac impulses.
MST = Mean Survival Time;
SD = Standard Deviation;
POD = Post Operative Days.

All 10 mice used in this study were treated identically. Five mice were sacrificed after day 16 for the purpose of further analyses such as those shown in Tables 3-6. The other 5 mice remained alive at day 90 and will be sacrificed at day 100, at which point analyses similar to those found in Tables 3-6 will be performed for both groups of mice sacrificed at day 16 and day 100.

It will be understood that various modifications may be made to the embodiments disclosed herein. For example, as those skilled in the art will appreciate, the specific sequences described herein can be altered slightly without necessarily adversely affecting the functionality of the polypeptide, antibody or antibody fragment used in binding OX-2/CD200. For instance, substitutions of single or multiple amino acids in the antibody sequence can frequently be made without destroying the functionality of the antibody or fragment. Thus, it should be understood that polypeptides or antibodies having a degree of identity greater than 70% to the specific antibodies described herein are within the scope of this disclosure. In particularly useful embodiments, antibodies having an identity greater than about 80% to the specific antibodies described herein are contemplated. In other useful embodiments, antibodies having an identity greater than about 90% to the specific antibodies described herein are contemplated. Therefore, the above description should not be construed as limiting, but merely as exemplifications of preferred embodi- References The following references are incorporated herein by reference to more fully describe the state of the art to which the present disclosure pertains. Any inconsistency between these publications below or those incorporated by reference above and the present disclosure shall be resolved in favor of the present disclosure.

1) Agarwal, et al. (2003). Disregulated expression of the Th2 cytokine gene in patients with intraoral squamous cell carcinoma. Immunol Invest 32:17-30.
2) Almasri, N M et al. (1992). Am J Hematol 40: 259-263.
3) Contasta, et al., (2003). Passage from normal mucosa to adenoma and colon cancer: alteration of normal sCD30 mechanisms regulating TH1/TH2 cell functions. Cancer Biother Radiopharm 18:549-557.
4) Gorczynski, et al. (1998). Increased expression of the novel molecule OX-2 is involved in prolongation of murine renal allograft survival. Transplantation 65:1106-1114.
5) Gorczynski, et al. (2001). Evidence of a role for CD200 in regulation of immune rejection of leukaemic tumour cells in C57BL/6 mice. Clin Exp Immunol 126:220-229.
6) Hainsworth, J D (2000). Oncologist 2000; 5(5):376-84.
7) Inagawa, et al. (1998). Mechanisms by which chemotherapeutic agents augment the antitumor effects of tumor necrosis factor: involvement of the pattern shift of cytokines from Th2 to Th1 in tumor lesions. Anticancer Res 18:3957-3964.
8) Ito, et al. (1999). Lung carcinoma: analysis of T helper type 1 and 2 cells and T cytotoxic type 1 and 2 cells by intracellular cytokine detection with flow cytometry. Cancer 85:2359-2367.
9) Kiani, et al. (2003). Normal intrinsic Th1/Th2 balance in patients with chronic phase chronic myeloid leukemia not treated with interferon-alpha or imatinib. Haematologica 88:754-761.
10) Lauerova, et al. (2002). Malignant melanoma associates with Th1/Th2 imbalance that coincides with disease progression and immunotherapy response. Neoplasma 49:159-166.
11) Maggio, et al. (2002). Chemokines, cytokines and their receptors in Hodgkin's lymphoma cell lines and tissues. Ann Oncol 13 Suppl 1:52-56.
12) Nilsson, K (1992). Burn Cell. 5(1):25-41.
13) Podhorecka, et al. (2002). T type 1/type 2 subsets balance in B-cell chronic lymphocytic leukemia—the three-color flow cytometry analysis. Leuk Res 26:657-660.
14) Pu, Q Q and Bezwoda, W (2000). Anticancer Res. 20(4): 2569-78.
15) Smyth, et al. (2003). Renal cell carcinoma induces prostaglandin E2 and T-helper type 2 cytokine production in peripheral blood mononuclear cells. Ann Surg Oncol 10:455-462.
16) Tatsumi, et al. (2002). Disease-associated bias in T helper type 1 (Th1)/Th2 CD4(+) T cell responses against MAGE-6 in HLA-DRB10401(+) patients with renal cell carcinoma or melanoma. J Exp Med 196:619-628.
17) Walls, et al. (1989). Int. J. Cancer 44:846-853.
18) Winter, et al. (2003). Tumour-induced polarization of tumour vaccine-draining lymph node T cells to a type 1 cytokine profile predicts inherent strong immunogenicity of the tumour and correlates with therapeutic efficacy in adoptive transfer studies. Immunology 108:409-419.
19) Cameron, et al. 2005. Myxoma virus M141R expresses a viral CD200 (vOX-2) that is responsible for down-regulation of macrophage and T-cell activation in vivo. J Virol 79:6052.
20) Foster-Cuevas, et al. 2004. Human herpesvirus 8 K14 protein mimics CD200 in down-regulating macrophage activation through CD200 receptor. J Virol 78:7667.
21) Nicholas, J. 2003. Human herpesvirus-8-encoded signalling ligands and receptors. J Biomed Sci 10:475.
22) Shiratori, et al. 2005. Down-regulation of basophil function by human CD200 and human herpesvirus-8 CD200. J Immunol 175:4441.
23) Voigt, et al. 2005. The English strain of rat cytomegalovirus (CMV) contains a novel captured CD200 (vOX2) gene and a spliced CC chemokine upstream from the major immediate-early region: further evidence for a separate evolutionary lineage from that of rat CMV Maastricht. J Gen Virol 86:263.
24) Zhang, et al. 2005. Kaposi's sarcoma-associated herpesvirus/human herpesvirus 8 replication and transcription activator regulates viral and cellular genes via interferon-stimulated response elements. J Virol 79:5640.

The invention claimed is:

1. A method of inhibiting an immune response in a subject having an autoimmune disease or an antibody mediated inflammatory disease, wherein said method comprises administering to a subject in need thereof an effective amount of i) an agent which inhibits interaction between CD200 and CD200R and ii) an immunosuppressive or immunomodulatory drug, wherein said agent is an antibody, or an antigen-binding fragment thereof, which binds to CD200, and wherein said antibody or antigen-binding fragment thereof has reduced or no effector function.

2. The method of claim 1, wherein said immune response is a humoral response.

3. The method of claim 2, wherein said immune response is an antibody mediated response.

4. The method of claim 1, wherein said immunosuppressive drug is cyclosporine A or rapamycin.

5. The method of claim 1, wherein said antibody or antigen-binding fragment thereof is selected from the group consisting of: a human antibody or antigen-binding fragment thereof, a humanized antibody or antigen-binding fragment thereof, a primatized antibody or antigen-binding fragment thereof, a chimeric antibody or antigen-binding fragment thereof, a murine antibody or antigen-binding fragment thereof, and a de-immunized antibody or antigen-binding fragment thereof.

6. The method of claim 1, wherein said antigen-binding fragment is selected from the group consisting of: a single-chain antibody, Fab, Fab', F(ab')$_2$, F(ab')$_3$, Fd, Fv, domain antibody, and any fragment of an anti-CD200 immunoglobulin that confers specific binding to CD200.

7. The method of claim 1, wherein said immunomodulatory or immunosuppressive drug is a calcineurin inhibitor.

8. The method of claim 7, wherein said calcineurin inhibitor is selected from the group consisting of tacrolimus and cyclosporine A.

9. The method of claim 1, wherein said immunomodulatory or immunosuppressive drug is selected from the group consisting of: adriamycin, azathiopurine, busulfan, cyclophosphamide, cyclosporine A, fludarabine, 5-fluorouracil, methotrexate, mycophenolate mofetil, a nonsteroidal anti-inflammatory, sirolimus (rapamycin), and tacrolimus (FK-506).

10. The method of claim 1, wherein said immunomodulatory or immunosuppressive drug is an antibody selected from the group consisting of: muromonab-CD3, alemtuzumab, basiliximab, daclizumab, rituximab, and anti-thymocyte globulin.

11. The method of claim 1, wherein said subject is human.

12. The method of claim 1, wherein said agent is administered i) prior to said drug, ii) subsequently to said drug, or iii) simultaneously with said drug.

13. The method of claim 1, wherein said autoimmune disease is an autoimmune hemolytic anemia.

14. The method of claim 1, wherein said agent is administered systemically.

15. The method of claim 1, wherein said agent is administered locally.

16. The method of claim 1, wherein said immune response is a primary response.

17. The method of claim 1, wherein said immune response is a secondary response.

18. A method of decreasing what constitutes an effective amount of an immunosuppressive or immunomodulatory drug administered to a subject having an autoimmune disease or an antibody mediated inflammatory disease, said method comprising administering to said subject: i) said immunosuppressive or immunomodulatory drug and ii) an agent which inhibits interaction between CD200 and CD200R , wherein less of said drug is required to effect immunosuppression or immunomodulation as compared to administering said drug without said agent, wherein said agent is an antibody, or an antigen-binding fragment thereof, which binds to CD200, and wherein said antibody or antigen-binding fragment thereof has reduced or no effector function.

19. The method of claim 18 wherein said drug is cyclosporine A or rapamycin.

20. The method of claim 18, wherein said antibody or antigen-binding fragment thereof is selected from the group consisting of a human antibody or antigen-binding fragment thereof, a humanized antibody or antigen-binding fragment thereof, a primatized antibody or antigen-binding fragment thereof, a chimeric antibody or antigen-binding fragment thereof, a murine antibody or antigen-binding fragment thereof, and a de-immunized antibody or antigen-binding fragment thereof 21. The method of claim 18, wherein said antigen-binding fragment is selected from the group consisting of single-chain antibody, Fab, Fab', F(ab')$_2$, F(ab')$_3$, Fd, Fv, domain antibody, and any fragment of an anti-CD200 immunoglobulin that confers specific binding to CD200.

22. The method of claim 18, wherein said antibody or antigen-binding fragment thereof exhibits: (x) reduced ADCC, (y) reduced CDC activity, or (z) reduced ADCC activity and reduced CDC activity.

23. The method of claim 18, wherein said antibody or antigen-binding fragment thereof exhibits: (x) no ADCC, (y) no CDC activity, or (z) no ADCC activity and no CDC activity.

24. The method of claim 18, wherein said antibody comprises a variant Fc region from an IgG1, IgG2, IgG3, IgG4, IgM, IgA1, IgA2, IgA, IgD, or IgE antibody.

25. The method of claim 18, wherein said antibody comprises a variant Fc constant region that has ADCC activity or CDC activity equal to or less than the ADCC activity or CDC activity the antibody would have if it had a Fc constant region comprising: (a) a glutamic acid substitution at amino acid position 236, (b) a glutamine substitution at amino acid position 298, and (c) an alanine substitution at amino acid positions 319, 321, and 323, wherein each substitution is relative to the amino acid sequence depicted in SEQ ID NO:28.

26. The method of claim 1, wherein said antibody or antigen-binding fragment thereof exhibits: (x) reduced ADCC, (y) reduced CDC activity, or (z) reduced ADCC activity and reduced CDC activity.

27. The method of claim 1, wherein said antibody or antigen-binding fragment thereof exhibits: (x) no ADCC, (y) no CDC activity, or (z) no ADCC activity and no CDC activity.

28. The method of claim 1, wherein said antibody comprises a variant Fc region from an IgG1, IgG2, IgG3, IgG4, IgM, IgA1, IgA2, IgA, IgD, or IgE antibody.

29. The method of claim 1, wherein said antibody comprises a variant Fc constant region that has ADCC activity or CDC activity equal to or less than the ADCC activity or CDC activity the antibody would have if it had a Fc constant region comprising: (a) a glutamic acid substitution at amino acid position 236, (b) a glutamine substitution at amino acid position 298, and (c) an alanine substitution at amino acid positions 319, 321, and 323, wherein each substitution is relative to the amino acid sequence depicted in SEQ ID NO:28.

* * * * *